(12) United States Patent
Sudau et al.

(10) Patent No.: US 9,822,099 B2
(45) Date of Patent: *Nov. 21, 2017

(54) TRIAZOLE DERIVATIVES

(71) Applicant: BAYER CROPSCIENCE AKTIENGESELLSCHAFT, Monheim am Rhein (DE)

(72) Inventors: Alexander Sudau, Langenfeld (DE); Sebastian Hoffmann, Neuss (DE); Peter Dahmen, Neuss (DE); Ulrike Wachendorff-Neumann, Neuwied (DE); David Bernier, Lyons (FR); Helene Lachaise, Lyons (FR); Stephane Brunet, St Andre de Corcy (FR); Jacky Vidal, Lozanne (FR); Pierre Genix, Lyons (FR); Pierre-Yves Coqueron, Lyons (FR); Julie Geist, Lyons (FR); Jean-Pierre Vors, Saint Foy les Lyons (FR); Philippe Kennel, Biot (FR); Ricarda Miller, Lyons (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,216

(22) PCT Filed: Apr. 9, 2014

(86) PCT No.: PCT/EP2014/057173
§ 371 (c)(1),
(2) Date: Oct. 8, 2015

(87) PCT Pub. No.: WO2014/167009
PCT Pub. Date: Oct. 16, 2014

(65) Prior Publication Data
US 2016/0068516 A1    Mar. 10, 2016

(30) Foreign Application Priority Data
Apr. 12, 2013  (EP) .................................... 13163593

(51) Int. Cl.
| C07D 403/06 | (2006.01) |
| A01N 43/647 | (2006.01) |
| C07D 213/50 | (2006.01) |
| C07D 213/61 | (2006.01) |
| C07D 215/14 | (2006.01) |
| C07D 401/06 | (2006.01) |
| C07D 405/06 | (2006.01) |
| A01N 43/653 | (2006.01) |
| C07D 213/30 | (2006.01) |

(52) U.S. Cl.
CPC ......... *C07D 403/06* (2013.01); *A01N 43/647* (2013.01); *A01N 43/653* (2013.01); *C07D 213/30* (2013.01); *C07D 213/50* (2013.01); *C07D 213/61* (2013.01); *C07D 215/14* (2013.01); *C07D 401/06* (2013.01); *C07D 405/06* (2013.01)

(58) Field of Classification Search
None
See application file for complete search history.

(56) References Cited

U.S. PATENT DOCUMENTS

| 4,486,218 A | 12/1984 | Reiser et al. |
| 4,499,281 A | 2/1985 | Holmwood et al. |
| 4,582,843 A | 4/1986 | Timmler et al. |
| 4,616,026 A | 10/1986 | Richardson et al. |
| 4,772,623 A | 9/1988 | Timmler et al. |
| 4,776,877 A | 10/1988 | Timmler et al. |
| 4,868,196 A | 9/1989 | Holmwood et al. |
| 4,894,382 A | 1/1990 | Elbe et al. |
| 4,898,954 A | 2/1990 | Mohrmann et al. |
| 4,960,453 A | 10/1990 | Holmwood et al. |
| 5,099,040 A | 3/1992 | Rosen et al. |
| 5,141,553 A | 8/1992 | Holmwood et al. |
| 5,216,006 A | 6/1993 | Scherkenbeck et al. |
| 5,252,582 A | 10/1993 | Jautelat et al. |
| 5,288,883 A | 2/1994 | Scherkenbeck et al. |
| 5,405,860 A | 4/1995 | Timmler et al. |
| 9,668,481 B2 * | 6/2017 | Hoffmann ............ A01N 43/653 |
| 2011/0018397 A1 | 7/2011 | Sudau et al. |

(Continued)

FOREIGN PATENT DOCUMENTS

| CN | 1760193 A | 4/2006 |
| CN | 101824002 A | 9/2010 |
| DE | 2431407 A1 | 1/1976 |

(Continued)

OTHER PUBLICATIONS

Baum "The Acylation of Lepidine (1)", Journal of Heterocyclic Chemistry (1966) vol. 3 No. 3 p. 272-274.

(Continued)

*Primary Examiner* — Hasan Ahmed
*Assistant Examiner* — Frank Choi
(74) *Attorney, Agent, or Firm* — McBee Moore Woodward & Vanik IP, LLC; Susan McBee; David Woodward

(57) ABSTRACT

The present invention relates to novel triazole derivatives, to processes for preparing these compounds, to compositions comprising these compounds, and to the use thereof as biologically active compounds, especially for control of harmful microorganisms in crop protection and in the protection of materials and as plant growth regulators.

15 Claims, No Drawings

(56) References Cited

U.S. PATENT DOCUMENTS

| | | |
|---|---|---|
| 2012/0010190 A1 | 1/2012 | Bissantz et al. |
| 2013/0281455 A1 | 10/2013 | Sudau et al. |

FOREIGN PATENT DOCUMENTS

| | | |
|---|---|---|
| DE | 2610022 A1 | 9/1976 |
| DE | 2638470 A1 | 3/1977 |
| DE | 3111238 A1 | 10/1982 |
| DE | 3144670 A1 | 5/1983 |
| DE | 3202604 A1 | 8/1983 |
| DE | 3235935 A1 | 3/1984 |
| DE | 3307217 A1 | 9/1984 |
| DE | 3315681 A1 | 10/1984 |
| DE | 4027608 A1 | 3/1992 |
| DE | 4204816 A1 | 8/1993 |
| EP | 0225739 A2 | 12/1985 |
| EP | 0291797 A2 | 11/1988 |
| EP | 0461502 A2 | 12/1991 |
| EP | 0470463 A2 | 2/1992 |
| FR | 2802772 A1 | 6/2001 |
| WO | 9302086 A1 | 2/1993 |
| WO | 9312121 A1 | 6/1993 |
| WO | 9529901 A1 | 11/1995 |
| WO | 03026663 A1 | 4/2003 |
| WO | 2005027837 A2 | 3/2005 |
| WO | 2005044785 A1 | 5/2005 |
| WO | 2005111003 A1 | 11/2005 |
| WO | 2008003622 A1 | 1/2008 |
| WO | 2008147544 A1 | 12/2008 |
| WO | 2009153554 A1 | 12/2009 |
| WO | 2010029066 A1 | 3/2010 |
| WO | 2010132999 A1 | 11/2010 |
| WO | 11012622 A1 | 2/2011 |
| WO | 2011/024004 A1 | 3/2011 |
| WO | 2011042389 A2 | 4/2011 |
| WO | 2012055942 A1 | 5/2012 |
| WO | 2012080476 A1 | 6/2012 |
| WO | 2012085815 A1 | 6/2012 |
| WO | 2012087784 A1 | 6/2012 |
| WO | 2012087833 A1 | 6/2012 |
| WO | 2012100342 A1 | 8/2012 |
| WO | 2012102297 A1 | 8/2012 |
| WO | 2012175119 A1 | 12/2012 |
| WO | 2012177603 A2 | 12/2012 |
| WO | 2012177608 A1 | 12/2012 |
| WO | 2012177635 A1 | 12/2012 |
| WO | 2012177638 A1 | 12/2012 |
| WO | 2012177725 A1 | 12/2012 |
| WO | 2012177728 A1 | 12/2012 |

OTHER PUBLICATIONS

Bernhardt et al, "Preparation of Solid Salt-Stabilized Functionalized Organozine Compounds and their Application to Cross-Coupling and Carbonyl Addition Reactions", Angewandte Chemie Int. Ed., 2011, vol. 50, pp. 9205-9209.
Wu et al., Chem. Asian J., 2012, vol. 7, No. 1, pp. 40-44.
Walker et al., "Identification of SD-0006, a potent diaryl pyrazole inhibitor of p38 MAP kinase." Bioorganic & Medicinal Chemistry Letters, 2010, pp. 2634-2640.
Roughley et al., "Fatty acid amide hydrolase inhibitors." Bioorganic & Medicinal Chemistry Letters, 22, 2012, pp. 901-906.
Rudd et al., "Development of macrocyclic inhibitors of HCV NS3/4A protease with cyclic constrained P2-O4 linkers." Bioorganic & Medicinal Chemistry Letters, 2012, pp. 7207-7213.
O'Brien et al., "Easily Prepared Air-and Moisture-Stable Pd . . . " Chem. Eur. J., 2006, vol. 12, pp. 4743-4748.
Metzger et al., "Polyfunctional benzylic zinc chlorides by the direct insertion of magnesium . . . " Chem Communication, 2008, pp. 5824-5826.
Yuguchi et al., "Pd(0)-Catalyzed Conjugate Addition of Benzylzinc Chlorides . . . " Journal of Organic Chemistry, 2004, pp. 908-914.
Higashino et al., "Studies on 4-Chloropyrido . . . " Chemical & Pharmaceutical Bulletin, 1970, vol. 18, No. 7:, pp. 1457-1464.
Higashino et al., "Triazolo . . . " Chemical & Pharmaceutical Bulletin, 1980, vol. 28, No. 1: pp. 337-342.
Liese et al., "Vielseitige Synthese von Alkinylcyclopropanen . . . " Chemische Berichte, 1986, vol. 119: pp. 2995-3026.
Comprehensive Heterocyclic Chemistry I, Pergamon Press, 1984; vol. 2, pp. 395-510 & vol. 3, pp. 1-197.
Comprehensive Heterocyclic Chemistry I, Pergamon Press, 1984; vol. 4, pp. 155-376 & vol. 5, pp. 167-498.
Comprehensive Heterocyclic Chemistry II, Pergamon Press, 1996; vol. 5, pp. 37-243 & vol. 6, pp. 1-278.
Comprehensive Heterocyclic Chemistry II, Pergamon Press, 1996; vol. 2, pp. 39-257 & vol. 3, pp. 1-220.
Comprehensive Heterocyclic Chemistry III, Pergamon Press, 2008; vol. 3, pp. 45-388 & vol. 4, pp. 1-364.
Comprehensive Heterocyclic Chemistry III, Pergamon Press, 2008; vol. 7, pp. 101-169; 217-308 & vol. 7, pp. 1-331.
Lu et al., "Monoalkyl and monoanilide yttrium complexes containing tridentate pyridyl-1-azaallyl dianionic ligands", Dalton Transactions, 2011, vol. 40, pp. 2366-2374.
Zhang et al., "The Cis-Trans Isomerization of 1,2,5,6 . . . ", The Journal of Organic Chemistry, Aug. 10, 2001, vol. 66, No. 16, pp. 5277-5282.
Peng et al., "Alcoholysis of Phosphaisocoumarins and Synthesis of 2-(2-Oxoalkyl)penylphosphates." European Journal of Organic Chemistry, 2008, pp. 5277-5282.
Jin et al., "Heterogeneously Catalyzed Efficient Hydration of Alkynes to Ketones by Tin-Tungsten Mixed Oxides" European Journal, 2011, vol. 17, pp. 1261-1267.
Kawase et al., "Trifluoroacetylation of Methylpyridines and Other Methylazines: A Convenient Acess to Trifluoroacetonylazines." Heterocycles, 1998, Vo. 48, No. 10, pp. 2103-2109.
M. Ross Grimmett, Imidazoles 3.02, University of Otago, Dunedin, New Zealand, 1996, Comprehensive Heterocyclic Chemistry II, pp. 1-144.
Jubert et al., "Preparation of New Classes of Aliphatic, Allylic, and Benzylic Zinc and Copper Reagents by the Insertion of Zinc Dust onto Organic Halides, Phosphates, and Sulfonates." J. Org. Chem. 1992, vol. 57: pp. 5425-5431.
Hanessian et al., "Total Synthesis of Pactamycin and Pactamycate: A Detailed Account." Journal of Organic Chemistry, 2012, vol. 77: pp. 9458-9472.
Burger et al., "Nuclear Substituted 2-Amino-1-(2-pyridyl) propanes." Journal of Medicinal Chemistry 1963, vol. 6, pp. 205-207.
Kang et al., "Benzotriazole-Mediated Synthesis of 2,3-Disuubstituted Allylic Alcohols." Journal of Organic Chemistry, 2001, vol. 66: pp. 2149-2153.
Mo et al., "Endolysins of Bacillus anthracins Bacteriophages . . . " Journal of the American Chemical Society, 2012, vol. 134: pp. 15556-15562.
Yoshida et al., "Nucleophilic Substitution Reaction at the Nitrogen of Arylsulfonamides with Phosphide Anion." Journal of the American Chemical Society, 2012, vol. 134: pp. 19358-19361.
Bergstrom et al., "Claisen Type Condensations with Quinaldine and Related Ammono Ketone Ethers." Journal of the American Chemical Society, 1937, vol. 59, pp. 1494-1497.
Fox et al., "Interactions between Hofmeister Anions and the Binding Pocket of a Protein." Journal of the American Chemical Society, 2015, vol. 137: pp. 3859-3866.
Barber et al., "The Preparation of Some Stilbene Derivatives" Part III, Journal of the Chemical Society, 1944, pp. 612-615.
Biscoe et al., "Selective Monoarylation of Acetate Esters and Aryl Methyl Ketones Using Aryl Chlorides." Organic letters, 2009, vol. 11, No. 8, pp. 1773-1775.
Lee et al., "Concise Asymmetric Synthesis of Orthogonally Protected syn- and aniti-1,3-Aminioalcohols." Organic Letters, 2013, vol. 15, No. 3: pp. 554-557.
ETO, Chem. Pharm. Bull, vol. 48, No. 7, pp. 982-990, 2000.

(56) References Cited

OTHER PUBLICATIONS

Dickinson, et al., "Novel Antifungal 2-Aryl-1-(1H-1,2,4-Triazol-1-yl)-2-ol Derivatives with High Activity against Aspergillus Fumigatus", Biorganic & Medicinal Chemistry Letters, vol. 6, No. 16, pp. 2031-2036, 1996.
Cao et al., "Palladium-Catalyzed a-Ketone Arylation under Mild Conditions", Eur. J. Org. Chem. 2011, pp. 1570-1574.
Nguyen et al., "A Fluorescent, Shape-Persistent Dendritic Host with Photoswitchable Guest Encapsulation and Intramolecular Energy Transfer", Journal of the American Chemical Society, 2011, vol. 133, pp. 11194-11204.
Yuguchi et al, "Pd(0)-Catalyzed Conjugate Addition of Benzylzinc Chlorides to a,B-Enones in an Atmosphere of Carbon Monoxide: Preparation of 1,4-Diketones", J. Org. Chem., 2004, vol. 69, pp. 908-914.

\* cited by examiner

TRIAZOLE DERIVATIVES

CROSS REFERENCE TO RELATED APPLICATIONS

This application is a §371 National Stage Application of PCT/EP2014/057173, filed 9 Apr. 2014, which claims priority to EP 13163593.0, filed 12 Apr. 2013.

BACKGROUND

Field of the Invention

The present invention relates to novel triazole derivatives, to processes for preparing these compounds, to compositions comprising these compounds, and to the use thereof as biologically active compounds, especially for control of harmful microorganisms in crop protection and in the protection of materials and as plant growth regulators.

Description of Related Art

It is already known that particular alkyl-substituted triazole derivatives can be used in crop protection as fungicides (cf. CN 1760193 A). It is also known that particular triazole derivatives can be used in several pharmaceutical indications and in crop protection as fungicides (cf. WO-A 2012/177635, WO-A 2012/177638, WO-A 2012/177603, WO-A 2012/177608, WO-A 2012/177725, WO-A 2012/177728).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

SUMMARY

Accordingly, the present invention provides novel triazole derivatives of the formula (I)

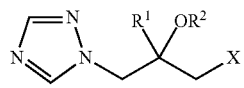

wherein
$R^1$ represents $C_1$-$C_8$-haloalkyl; $C_2$-$C_8$-halooalkenyl; $C_2$-$C_8$-haloalkynyl; $C_3$-$C_7$-halocycloalkyl-$C_1$-$C_4$-alkyl; $C_3$-$C_7$-halocycloalkyl-$C_1$-$C_4$-haloalkyl; $C_3$-$C_7$-cycloalkyl-$C_1$-$C_4$-haloalkyl; substituted or non-substituted $C_3$-$C_7$-cycloalkyl; substituted or non-substituted $C_3$-$C_7$-cycloalkenyl; substituted or non-substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; substituted or non-substituted heterocycloalkyl-$C_1$-$C_8$-alkyl;
and
$R^2$ represents H, $C_1$-$C_8$-alkyl, —Si($R^{3a}$)($R^{3b}$)($R^{3c}$), —P(O)(OH)$_2$, —CH$_2$—O—P(O)(OH)$_2$, substituted or non-substituted —C(O)—$C_1$-$C_8$-alkyl, substituted or non-substituted —C(O)—$C_3$-$C_7$-cycloalkyl, substituted or non-substituted —C(O)NH—$C_1$-$C_8$-alkyl; substituted or non-substituted —C(O)N-di-$C_1$-$C_8$-alkyl; substituted or non-substituted —C(O)O—$C_1$-$C_8$-alkyl;
and
$R^{3a}$, $R^{3b}$, $R^{3c}$ represent independent from each other a substituted or non-substituted $C_1$-$C_8$-alkyl;
and
X represents a substituted or non-substituted unsaturated 6-membered heterocycle containing 1 or 2 nitrogen atom(s) as heteroatom(s) or a benzannulated derivative thereof;
and its salts or N-oxides.

DETAILED DESCRIPTION OF A PREFERRED EMBODIMENT

The salts or N-oxides of the triazole derivatives of formula (I) also have fungicidal properties.

Unless otherwise indicated the term "substituted or non-substituted" in the definitions for $R^1$, $R^2$, $R^{3a}$, $R^{3b}$, $R^{3c}$ and X given in the formulae of the present application and preferred ranges or embodiments thereof preferably includes non-substituted or substituted by halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; $C_1$-$C_8$-alkylthio; $C_1$-$C_8$-halogenalkylthio; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-alkoxy; $C_1$-$C_8$-halogenoalkoxy; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkykarbonyl; $C_1$-$C_8$-halogenoalkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; 2-oxopyrrolidin-1-yl, (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl;

phenyl; 5-membered heteroaryl; 6-membered heteroaryl; benzyloxy; phenyloxy; benzylsulfanyl; benzylamino; phenoxy; phenylsulfanyl; or phenylamino; wherein the benzyl, phenyl, 5-membered heteroaryl, 6-membered heteroaryl, benzyloxy or phenyloxy may be optionally substituted by one or more group(s) selected from the aforementioned list.

Preferably the term "substituted or non-substituted" in the definitions for $R^1$, $R^2$, $R^{3a}$, $R^{3b}$, $R^{3c}$ and X preferably includes non-substituted or substituted by halogen; cyano; $C_1$-$C_8$-alkyl; $C_1$-$C_8$-haloalkyl; $C_1$-$C_8$-alkoxy; $C_1$-$C_8$-halogenalkoxy; ($C_1$-$C_8$-alkoxyimino)-$C_1$-$C_8$-alkyl; $C_3$-$C_7$-cycloalkyl; $C_3$-$C_7$-halogencycloalkyl; $C_2$-$C_8$-alkenyl; or $C_2$-$C_8$-alkynyl.

The formula (I) provides a general definition of the triazole derivatives according to the invention. Preferred radical definitions for the formulae shown above and below are given below. These definitions apply to the end products of the formula (I) and likewise to all intermediates.

$R^1$ preferably represents $C_1$-$C_8$-haloalkyl; substituted or non-substituted $C_3$-$C_7$-cycloalkyl.

$R^1$ more preferably represents $C_1$-$C_4$-haloalkyl; non-substituted or halogen-substituted or $C_1$-$C_3$-alkyl-substituted or $C_3$-$C_7$-cycloalkyl-substituted or $C_1$-$C_8$-alkoxy-substituted $C_3$-$C_7$-cycloalkyl.

$R^1$ most preferably represents $C_1$-$C_4$-haloalkyl; non-substituted or halogen-substituted or $C_1$-$C_3$-alkyl-substituted or $C_1$-$C_8$-alkoxy-substituted cyclopropyl.

In preferred embodiments of the present invention $R^1$ represents a 1-substituted cyclopropyl wherein the substituent is selected from halogen or $C_1$-$C_3$-alkyl or $C_1$-$C_8$-alkoxy.

In another preferred embodiment of the present invention $R^1$ represents a substituted $C_3$-$C_7$-cycloalkyl, preferably a substituted cyclopropyl wherein two substituents at the same or different carbon atom(s) can form together with the $C_3$-$C_7$-cycloalkyl, preferably the cyclopropyl to which they are attached a substituted or non-substituted bicycloalkyl.

In another preferred embodiment of the present invention $R^1$ represents a mono- or multiple fluorinated $C_1$-$C_4$-alkyl.

In another preferred embodiment
$R^1$ preferably represents $C_1$-$C_8$-haloalkyl; substituted or non-substituted $C_3$-$C_7$-cycloalkyl; substituted or non-substituted aryl-$C_1$-$C_4$-alkyl; substituted or non-substituted phenoxy-$C_1$-$C_4$-alkyl; substituted or non-substituted phenyl-$C_3$-$C_7$-cycloalkyl or substituted or non-substituted hetaryl.

In another preferred embodiment
$R^1$ more preferably represents $C_1$-$C_4$-haloalkyl; non-substituted or halogen-substituted $C_3$-$C_7$-cycloalkyl; non-substituted or halogen-substituted aryl-$C_1$-$C_4$-alkyl; non-substituted or halogen-substituted phenoxy-$C_1$-$C_4$-alkyl; non-substituted or halogen-substituted phenyl-$C_3$-$C_7$-cycloalkyl or non-substituted or halogen-substituted hetaryl.

In another preferred embodiment
$R^1$ most preferably represents $C_1$-$C_4$-haloalkyl; non-substituted or halogen-substituted $C_3$-$C_7$-cycloalkyl; non-substituted or halogen-substituted aryl-$C_1$-$C_4$-alkyl; non-substituted or halogen-substituted phenoxy-$C_1$-$C_4$-alkyl; non-substituted or halogen-substituted phenyl-$C_3$-$C_7$-cycloalkyl or non-substituted or halogen-substituted pydridinyl.

X preferably represents a substituted or non-substituted unsaturated 6 membered heterocycle containing 1 or 2 nitrogen atom(s) as heteroatom(s) or a benzannulated derivative thereof, with the proviso that X does not represent 2-pyridinyl.

X more preferably represents a substituted or non-substituted 3-pyridinyl, 4-pyridinyl, 4-pyrimidinyl, 5-pyrimidinyl, pyrazin-2-yl, pyridazin-3-yl, pyridazin-4-yl, quinoline-2-yl or quinoline-3-yl.

X also more preferably represents a substituted or non-substituted 3-pyridinyl, 4-pyridinyl, 4-pyrimidinyl, 5-pyrimidinyl, pyrazin-2-yl, pyridazin-3-yl, pyridazin-4-yl, quinoline-2-yl, quinoline-3-yl or quinoline-4-yl.

X most preferably represents substituted or non-substituted 3-pyridinyl, 4-pyridinyl, quinoline-2-yl or quinoline-3-yl.

In preferred embodiments of the present invention X represents substituted or non-substituted 3-pyridinyl or 4-pyridinyl.

In another preferred embodiments of the present invention X represents substituted 3-pyridinyl or 4-pyridinyl.

In another preferred embodiment of the present invention X represents 3-pyridinyl or 4-pyridinyl substituted by at least one halogen substituent.

In another preferred embodiment of the present invention X represents substituted or non-substituted 2-pyridinyl.

In another preferred embodiment of the present invention X represents 2-pyridinyl substituted by at least one halogen substituent.

For all definitions for X preference is given to such heterocycles which do not contain other heteroatom(s) than nitrogen atom(s).

$R^2$ preferably represents H, $C_1$-$C_8$-alkyl, substituted or non-substituted —C(O)—$C_1$-$C_8$-alkyl.

$R^2$ more preferably represents H.

In such embodiments of the present invention wherein $R^2$ represents —Si($R^{3a}$)($R^{3b}$)($R^{3c}$)

$R^{3a}$, $R^{3b}$, $R^{3c}$ preferably represent independent from each other methyl, ethyl or tert-butyl, $R^{3a}$, $R^{3b}$, $R^{3c}$ more preferably represents methyl.

In another preferred embodiments of the present invention
$R^1$ preferably represents $C_1$-$C_8$-haloalkyl; substituted or non-substituted $C_3$-$C_7$-cycloalkyl; substituted or non-substituted aryl-$C_1$-$C_4$-alkyl; substituted or non-substituted phenoxy-$C_1$-$C_4$-alkyl; substituted or non-substituted phenyl-$C_3$-$C_7$-cycloalkyl or substituted or non-substituted hetaryl, and $R^2$ preferably represents H, $C_1$-$C_8$-alkyl, substituted or non-substituted —C(O)—$C_1$-$C_8$-alkyl, and X also more preferably represents a substituted or non-substituted 2-pyridinyl, 3-pyridinyl, 4-pyridinyl, 4-pyrimidinyl, 5-pyrimidinyl, pyrazin-2-yl, pyridazin-3-yl, pyridazin-4-yl, quinoline-2-yl, quinoline-3-yl or quinoline-4-yl.

In another preferred embodiments of the present invention
$R^1$ preferably represents $C_1$-$C_8$-haloalkyl; substituted or non-substituted $C_3$-$C_7$-cycloalkyl; substituted or non-substituted aryl-$C_1$-$C_4$-alkyl; substituted or non-substituted phenoxy-$C_1$-$C_4$-alkyl; substituted or non-substituted phenyl-$C_3$-$C_7$-cycloalkyl or substituted or non-substituted hetaryl, and $R^2$ preferably represents H, and X also more preferably represents a substituted or non-substituted 2-pyridinyl, 3-pyridinyl, 4-pyridinyl, 4-pyrimidinyl, 5-pyrimidinyl, pyrazin-2-yl, pyridazin-3-yl, pyridazin-4-yl, quinoline-2-yl, quinoline-3-yl or quinoline-4-yl.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the abovementioned preferred definitions.

Particular preference is given to those compounds of the formula (I) in which each of the radicals have the abovementioned more preferred definitions.

Very particular preference is given to those compounds of the formula (I) in which each of the radicals have the above mentioned most preferred definitions.

In the definitions of the symbols given in the above formulae, collective terms were used which are generally representative of the following substituents:

The definition $C_1$-$C_8$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls and octyls, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl and 1-methyl-2-cyclopropylethyl. A preferred range is $C_1$-$C_4$-alkyl, such as methyl, ethyl, n-, isopropyl, n-, iso-, sec-, tert-butyl. The definition $C_1$-$C_3$-alkyl comprises methyl, ethyl, n-, isopropyl.

The definition halogen comprises fluorine, chlorine, bromine and iodine.

Halogen-substituted alkyl—referred to as $C_1$-$C_8$-haloalkyl—represents, for example, $C_1$-$C_8$-alkyl as defined above substituted by one or more halogen substituents which can be the same or different. Preferably $C_1$-$C_8$-haloalkyl represents chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methylethyl, 2-fluoro-1,1-dimethylethyl, 2-fluoro-1-fluoromethyl-1-methylethyl, 2-fluoro-1,1-di(fluoromethyl)-ethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

Mono- or multiple fluorinated $C_1$-$C_4$-alkyl represents, for example, $C_1$-$C_4$-alkyl as defined above substituted by one or more fluorine substituent(s). Preferably mono- or multiple fluorinated $C_1$-$C_4$-alkyl represents fluoromethyl, difluoromethyl, trifluoromethyl, 1-fluoroethyl, 2-fluoroethyl, 2,2-difluoroethyl, 2,2,2-trifluoroethyl, pentafluoroethyl, 1-fluoro-1-methylethyl, 2-fluoro-1,1-dimethylethyl, 2-fluoro-1-fluoromethyl-1-methylethyl, 2-fluoro-1,1-di(fluoromethyl)-ethyl, 1-methyl-3-trifluoromethylbutyl, 3-methyl-1-trifluoromethylbutyl.

The definition $C_2$-$C_8$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, 1-methyl-1-propenyl, 1-ethyl-1-butenyl, 2,4-dimethyl-1-pentenyl, 2,4-dimethyl-2-pentenyl. Halogen-substituted alkenyl—referred to as $C_2$-$C_8$-haloalkenyl—represents, for example, $C_2$-$C_8$-alkenyl as defined above substituted by one or more halogen substituents which can be the same or different.

The definition $C_2$-$C_8$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls. Halogen-substituted alkynyl—referred to as $C_2$-$C_8$-haloalkynyl—represents, for example, $C_2$-$C_8$-alkynyl as defined above substituted by one or more halogen substituents which can be the same or different.

The definition $C_3$-$C_7$-cycloalkyl comprises monocyclic saturated hydrocarbyl groups having 3 to 7 carbon ring members, such as cyclopropyl, cyclobutyl, cyclopentyl, cyclohexyl and cycloheptyl.

The definition halogen-substituted cycloalkyl and halocycloalkyl comprises monocyclic saturated hydrocarbyl groups having 3 to 7 carbon ring members, such as 1-fluorocyclopropyl and 1-chlorocyclopropyl.

The definition bicycloalkyl comprises spirocyclic alkyl wherein two substituents at the same carbon atom of a $C_3$-$C_7$-cycloalkyl can form together with the carbon atom to which they are attached a $C_3$-$C_7$-cycloalkyl, this definition comprises for example the meaning spiro[2.2]pentyl. The definition bicycloalkyl also comprises bicyclic alkyls wherein two substituents at different adjacent or non-adjacent carbon atoms of a $C_3$-$C_7$-cycloalkyl can form together with the carbon atoms to which they are attached a $C_3$-$C_7$-cycloalkyl, this definition comprises for example the meaning bicyclo[2.2.1]heptane-2-yl, bicyclo[2.2.1]heptane-7-yl, bicyclo[4.1.0]heptane-2-yl, bicyclo[4.1.0]heptane-3-yl, bicyclo[4.1.0]heptane-7-yl The definition bicycloalkyl also comprises bicyclic alkyls wherein two substituents at different adjacent or non-adjacent carbon atoms of a $C_3$-$C_7$-cycloalkyl can form an alkylene bridge between the carbon atoms to which they are attached, this definition comprises for example the meaning bicyclo[2.2.1]hept-2-ene-2-yl, bicyclo[2.2.1]hept-2-ene-5-yl, bicyclo[2.2.1]hept-2-ene-7-yl.

The definition aryl comprises unsubstituted or substituted, aromatic, mono-, bi- or tricyclic ring, for example phenyl, naphthyl, anthracenyl (anthryl), phenanthracenyl (phenanthryl).

The definition 6-membered unsaturated heterocycle containing 1 or 2 nitrogene atom(s) as heteroatom(s) comprises for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl.

The definition benzannulated derivative of 6-membered unsaturated heterocycle containing 1 or 2 nitrogene atom(s) as heteroatom(s) comprises for example 2-quinolinyl, 3-quinolinyl, 4-quinolinyl, 1-isoquinolinyl, 3-isoquinolinyl, 4-isoquinolinyl, 2-quinazolinyl, 4-quinazolinyl, cinnolin-3-yl; cinnolin-4-yl; phthalazin-1-yl; phthalazin-4-yl; quinoxalin-2-yl; quinoxalin-3-yl.

The definition hetaryl or heteroaryl comprises unsubstituted or substituted, unsaturated, benzoannulated or not benzoannulated heterocyclic 5- to 10-membered ring containing up to 4 heteroatoms selected from N, O and S. Preferably The definition hetaryl or heteroaryl comprises unsubstituted or substituted, unsaturated heterocyclic 5- to 7-membered ring containing up to 4 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

The definition heterocycloalkyl comprises saturated or partially unsaturated mono-, bi- or tricyclic ring system consisting of C-atoms and containing up to 4 heteroatoms selected from N, O and S: for example aziridinyl, pyrrolidinyl, dihydropyridyl, piperidinyl, piperazinyl, morpholinyl, thiomorpholinyl, tetrahydrofuranyl, tetrahydrothiofuranyl, tetrahydropyranyl, pyranyl, isoxazolidinyl, isoxazolinyl, pyrazolinyl, dihydropyrrolyl, tetrahydropyridinyl, dioxolanyl, dioxanyl, oxathiolanyl, oxathianyl, dithhiolanyl, dithianyl;

Optionally substituted radicals may be mono- or polysubstituted, where in the case of polysubstitution, the substituents may be identical or different.

Unless indicated otherwise, a group or a substituent which is substituted according to the invention preferably can be substituted by one or more group(s) selected from the list consisting of halogen; SH; nitro; hydroxyl; cyano; amino; sulfanyl; pentafluoro-$\lambda^6$-sulfanyl; formyl; formyloxy; formylamino; carbamoyl; N-hydroxycarbamoyl; carbamate; (hydroxyimino)-$C_1$-$C_6$-alkyl; $C_1$-$C_8$-alkyl; $C_1$-$C_8$-halogenalkyl; $C_1$-$C_8$-alkyloxy; $C_1$-$C_8$-halogenalkyloxy; $C_1$-$C_8$-alkylthio; $C_1$-$C_8$-halogenalkylthio; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halocycloalkyl; $C_3$-$C_7$-cycloalkenyl; $C_3$-$C_7$-halocycloalkenyl; $C_4$-$C_{10}$-cycloalkylalkyl; $C_4$-$C_{10}$-halocycloalkylalkyl; $C_6$-$C_{12}$-cycloalkylcycloalkyl; tri($C_1$-$C_8$-alkyl)silyl-$C_3$-$C_7$-cycloalkyl; $C_1$-$C_8$-halogenoalkyl; $C_3$-$C_7$-halogenocycloalkyl; $C_2$-$C_8$-alkenyl; $C_2$-$C_8$-alkynyl; $C_2$-$C_8$-alkenyloxy; $C_2$-$C_8$-halogenalkenyloxy; $C_2$-$C_8$-alkynyloxy; $C_1$-$C_8$-alkylamino; di-$C_1$-$C_8$-alkylamino; $C_1$-$C_8$-halogenalkylamino; di-$C_1$-$C_8$-halogenalkylamino; $C_1$-$C_8$-alkylaminoalkyl; di-$C_1$-$C_8$-alkylaminoalkyl; $C_1$-$C_8$-alkoxy; $C_1$-$C_8$-halogenoalkoxy; $C_1$-$C_8$-cyanoalkoxy; $C_4$-$C_8$-cycloalkylalkoxy; $C_3$-$C_6$-cycloalkoxy; $C_2$-$C_8$-alkoxyalkoxy; $C_1$-$C_8$-alkylcarbonylalkoxy; $C_1$-$C_8$-alkylsulfanyl; $C_1$-$C_8$-halogenoalkylsulfanyl; $C_2$-$C_8$-alkenyloxy; $C_2$-$C_8$-halogenoalkenyloxy; $C_3$-$C_8$-alkynyloxy; $C_3$-$C_8$-halogenoalkynyloxy; $C_1$-$C_8$-alkylcarbonyl; $C_1$-$C_8$-halogenoalkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; 2-oxopyrrolidin-1-yl, (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroaryl; 6-membered heteroaryl; benzyloxy; phenyloxy; benzylsulfanyl; benzylamino; phenoxy; phenylsulfanyl; or phenylamino; wherein the benzyl, phenyl, 5-membered heteroaryl, 6-membered heteroaryl, benzyloxy or phenyloxy may be optionally substituted by one or more group(s) selected from the aforementioned list.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

If appropriate, the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

If appropriate, the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

If appropriate, the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

The compounds of formula (I) wherein X is substituted by a hydroxy, a sulfanyl or an amino substituent may be found in its tautomeric form resulting from the shift of the proton of said hydroxy, sulfanyl or amino group. All tautomeric forms of such compounds of the present invention) wherein X is substituted by a hydroxy, a sulfanyl or an amino substituent are also part of the present invention.

Illustration of the Processes and Intermediates

The present invention furthermore related to processes for preparing compounds of formula (I). The present invention furthermore relates to intermediates such as compounds of formulae (V), (XII), (XV) and the preparation thereof.

The compounds (I) can be obtained by various routes in analogy to prior art processes known (see e.g. EP-A 461 502, DE-A 40 27 608, DE-A 32 35 935 and references therein) and by synthesis routes shown schematically below and in the experimental part of this application. Unless indicated otherwise, the radicals X, $R^1$, $R^2$ and $R^3$ have the meanings given above for the compounds of formula (I). These definitions apply not only to the end products of the formula (I) but likewise to all intermediates.

Process A (Scheme 1):

Scheme 1: Process A - Preparation of Ketones (V).

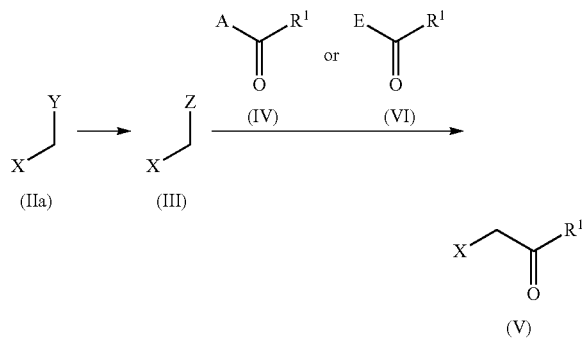

Y = ——H or ——OH
Z = halogen, ——$OSO_2$—$C_1$-$C_8$-alkyl, ——$OSO_2$-aryl,
——OP(O)(O——$C_1$-$C_8$-alkyl)$_2$ or ——OP(O)(O-aryl)$_2$, preferably ——Cl or ——Br
A = halogen, preferably ——Cl
E = ——O——$C_1$-$C_8$-alkyl, preferably ——O-methyl, ——O-ethyl; ——O-aryl; ——S——$C_1$-$C_8$-alkyl; ——S-aryl; ——$NHR^a$; ——$NR^aR^b$; $R^a$: is aryl, $C_1$-$C_8$-alkyl, or $C_3$-$C_7$-cycloalkyl, $R^b$: is $C_1$-$C_8$-alkyl or $C_1$-$C_8$-alkyloxy, preferably ——$NMe_2$,
——NMeOMe; or heterocyclic leaving groups, such as imidazole, triazole and hydroxybenzotriazole.

Compounds (IIa) and/or (III) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

The compounds (IIa) (Scheme 1) can be converted by means of methods described in the literature to the corresponding compounds (III) and subsequently to compounds (V). In a first process, for example, compounds (IIa) are halogenated.

In case Y stands for hydrogen, the compounds (IIa) can be halogenated e.g. with Bromo- or Chlorosuccinimide (see e.g. WO-A 2011/012622, WO-A 2008/003622, WO-A 2005/111003; Synthesis, 18, 2008, 2996 and references cited therein), preferably in the presence of a radical initiator such as Azobisisobutyronitrile or dibenzoyl peroxide and in the presence of an organic solvent, e.g. a chlorinated organic solvent such as tetrachloromethane. Alternatively, compounds (IIa) undergo side-chain halogenation in the presence of bromine or chlorine (see e.g. EP 557967) to obtain compounds (III). Optionally, a radical initiator such as Azobisisobutyronitrile or dibenzoyl peroxide can be used. Alternatively, compounds (IIa) are reacted with a base, e.g. methyl lithium, and subsequently with a halogen source such as Magnesiumbromide to obtain compounds (III) (see e.g. WO-A 2012/087784)

Compounds (IIa) where Y stands for —OH are reacted with halogenating agents, such as $PBr_3$, $PCl_3$ or thionyl chloride, to obtain compounds (III) (see e.g. WO-A 2009/153554, Bioorganic & Medicinal Chemistry Letters, 22, 2012, 901-906, WO-A 2010/132999 and references cited therein). Alternatively, compounds (IIa) can be reacted with sulfonyl halides, such as e.g. Mesylchloride or Tosylchloride, or with phosphonic acid halides, such as e.g. diphenylphosphoryl chloride, to obtain the respective sulfonates and phosphates (see e.g. J. Org. Chem. 1992, 57, 5425-5431 and references cited therein)

The compounds (III) can subsequently be reacted with compounds (IV) or (VI) wherein A and E represent a replaceable group such as halide, —OR, $NHR^a$ or $NR^aR^b$, preferably chloro, —O-methyl, —O— ethyl, —$NMe_2$ or —NMeOMe. To obtain compounds (V), compounds (III) are reacted in a first step with e.g. Zink, Magnesium or isopropylmagnesium chloride, followed by a carbonyl compound (IV) or (VI) preferably under anhydrous conditions and optionally in the presence of a metal catalyst, such as palladium- or nickel-based catalysts. The metal catalyst can be used such as $(Ph_3P)_2PdCl_2$ (e.g. WO-A 2012/087784, EP-A 461 502), PEPPSI-IPr (Chem. Eur. J. 2006, 12, 4743-4748) or prepared in-situ by the mixing of a metals salt (e.g. $Pd(OAc)_2$) and a ligand (such as e.g. $PPh_3$, 2-dicyclohexylphosphino-2',6'-dimethoxybiphenyl (S-Phos)). The Insertion of the metal can be enhanced by the addition of ionic salts, such as LiBr, LiCl, LiI, CuI, $Zn(OPiv)_2$, $MgCl_2$, CuCN (see e.g. Dissertation Albrecht Metzer 2010 (University Munich); Angew. Chem. Int. Ed. 2011, 50, 9205-9209), or by activation of the metal using halogenated alkanes (1,2-dibromoethane) or halogenated alkylsilanes (TMSCl). Alternatively this sequence may be carried out in a one-pot fashion (see e.g. Beller et al., Chem. Asian J., 2011, 7(1) 40-44).

The reaction can be performed at temperatures between room temperature and refluxing temperature of the solvent.

As the solvent, all common solvents inert under the reaction conditions, such as for example ethers (such as e.g. tetrahydrofurane, diethyl ether) can be used and the reaction can be effected in mixtures of two or more of these solvents.

Process B (Scheme 2):

Scheme 2: Process B - Preparation of Ketones (V).

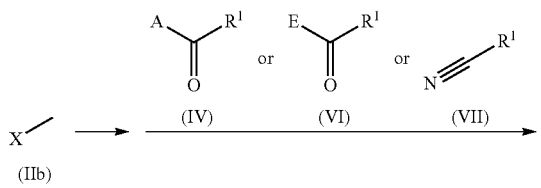

(V)

A = halogen, preferably Cl
E = —O—C$_1$-C$_8$-alkyl, preferably —O-methyl, —O-ethyl; —O-aryl;
—S—C$_1$-C$_8$-alkyl; —S-aryl; —NHR$^a$; —NR$^a$R$^b$; R$^a$: is aryl, C$_1$-C$_8$-alkyl, or C$_3$-C$_7$-cycloalkyl, R$^b$; is C$_1$-C$_8$-alkyl or C$_1$-C$_8$-alkyloxy, preferably —NMe$_2$, —NMeOMe; or heterocyclic leaving groups, such as imidazole, triazole and hydroxybenzotriazole.

Compounds (IIb) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

There are numerous literature methods for the preparation of ketones (see e.g. WO-A 2012/055942, WO-A 2012/100342, WO-A 2012/087784, WO-A 2012/087833, US-A 2012/0010190, Dalton Transaction, 2011, 2366-2374, Journal of the American Chemical Society, 1955, 3858-3860, Journal of the American Chemical Society, 1937, 1494-1497, WO-A 2012/085815, WO-A 2011/042389, WO-A 2003/026663, Heterocycles, 1998, 2103-2109, Bioorganic & Medicinal Chemistry Letters, 2010, 2634-2640).

In general, it is possible to prepare compounds of the formula (V) from corresponding compounds (IIb) and (IV) and/or from corresponding compounds (IIb) and (VI) with suitable groups A and E (see Scheme 2, process B). Compounds (IIb) are optionally reacted sequentially with a base, e.g. n-butyllithium, lithium-diisopropylamide, lithium bis(trimethylsilyl)amide, sodium bis(trimethylsilyl)amide, potassium bis(trimethylsilyl)amide sodium amide, potassium amide, potassium tert-butoxide, methyl lithium, TMP$_2$Zn.2MgCl$_2$.2LiCl (see e.g. Dissertation Albrecht Metzer 2010, University Munich), followed by compounds (IV) or (VI), preferably under anhydrous conditions. Optionally, the reaction of compounds (IIb) and compounds (IV) or (VI) is carried out in the presence of a base in a one-pot fashion. The possible groups for A and E are, for example, halide, —OR, NHR$^a$ or NR$^a$R$^b$, preferably chloro, —O-methyl, —O-ethyl, —NMe$_2$ or —NMeOMe, etc., which can act as appropriate leaving groups to form the desired ketones (V) under suitable reaction conditions (Scheme 2).

In an alternative route compounds (IIb) are reacted with compounds (VII) in the presence of a base, e.g. phenyl lithium or methyl lithium, to obtain compounds (V) (see e.g. Journal of the American Chemical Society, 2011, 11194-11204; Journal of Medicinal Chemistry 1963, 205-207 and references cited therein).

Process C (Scheme 3):

Scheme 3: Process C - Preparation of Ketones (V).

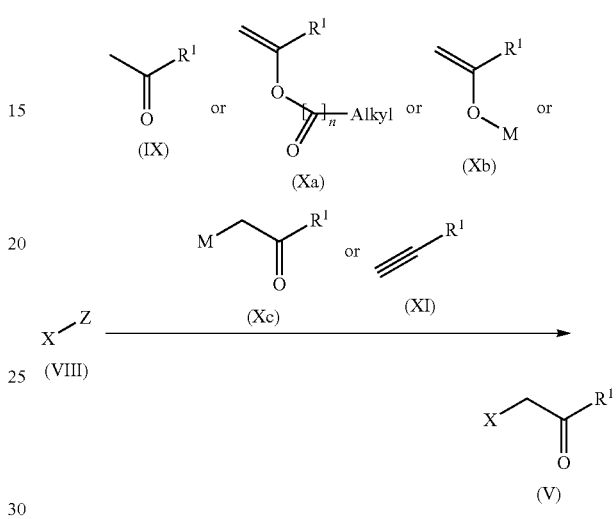

Z = halogen, preferably Cl or Br
n = 0.1
M = Li, MgZ$^M$, ZnZ$^M$, Si(C$_1$-C$_8$-alkyl)$_3$, Sn(C$_1$-C$_8$-alkyl)$_3$
Z$^M$ = halogen, hydroxyl preferably Cl or Br One means of preparing compounds of the formula (V) from corresponding compounds (VIII) with the compounds (IX) or (X) or (XI) is shown in Scheme 3 (Process C). Compounds (X) include compounds (Xa), (Xb) and (Xc)

Compounds (VIII) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

Compounds (IX), (X) and (XI) are either commercially available or producible by processes described in the literature (see, for example, WO-A 2010/029066; Chemische Berichte, 1986, 2995-3026 and references cited therein).

A compound having the general formula (V) can be synthesized analogously to methods described in the literature (see, for example Organic letters, 2009, 1773-1775; European Journal of Organic Chemistry, 2011, 1570-1574), by a coupling reaction of a compound with the corresponding general formula (VIII) with a substrate of the general formula (IX), (X) or (XI) where Z is halogen, preferably chlorine or bromine.

Compounds (VIII) are reacted with compounds of the general structure (IX) or (X) to obtain compounds (V) analogously to methods described in the literature (e.g. Organic letters, 2009, 1773-1775, European Journal of Organic Chemistry, 2011, 1570-1574, Chemical & Pharmaceutical Bulletin, 1970, 1457-1464, Chemical & Pharmaceutical Bulletin, 1980, 337-342, WO-A 2005/044785). Those reactions can be optionally carried out in the presence of a catalyst and a base.

As catalysts for the reaction various metal based catalysts can be used which are either used directly or being in situ prepared from a metal precursor (e.g. $Pd_2dba_3$, $Pd(OAc)_2$) and a ligand (e.g. phosphine based ligands like Xanthphos, 2-(dicyclohexylphosphino)-2'-methylbiphenyl, 2-Diphenylphosphino-2'-(N,N-dimethylamino)biphenyl, tri-t-butylphosphine, Tri-o-tolylphosphine) (see e.g. WO-A 2008/147544, WO-A 2005/027837).

As bases various organic and inorganic bases can be used such as potassium phosphate, base, e.g. sodium amide, sodium hydride or sodium tert-butoxide. Alternatively, silicon containing bases can be used (e.g. NaHMDS, KHMDS, LiHMDS).

Compounds (VIII) are reacted with compounds of the general structure (XI) to obtain compounds (V) analogously to methods described in the literature (e.g. WO-A 2012/080476). The intermediary alkines can be further converted to the corresponding ketones (V) by methods known in the literature (see e.g. Chemistry—A European Journal, 2011, 1261-1267; European Journal of Organic Chemistry, 2008, 5277-5282; Journal of the Chemical Society, 1944, 612-615 and references cited therein).

Process D (Scheme 4):

Scheme 4: Process D - Preparation of Epoxides (IX).

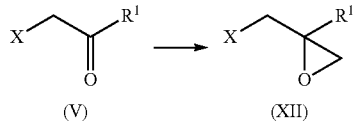

(V)    (XII)

The compounds (V) (Scheme 4) can be converted by means of methods described in the literature to the corresponding compounds (XII) (see e.g. EP-A 461 502, DE-A 33 15 681, EP-A 291 797). Intermediates (V) are preferably reacted with trimethylsulfoxonium- or trimethylsulfonium-salts, preferably trimethylsulfoxonium halides, trimethylsulfonium halides, trimethylsulfoxonium methylsulfates or trimethylsulfonium methylsulfates, preferably in the presence of a base such as sodium hydroxide.

Process E (Scheme 5):

Scheme 5: Process E - Preparation of Epoxides (IX).

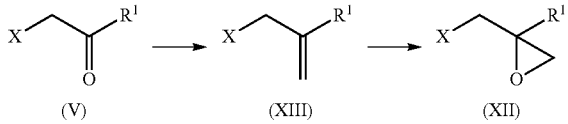

(V)    (XIII)    (XII)

Alternatively, compounds (V) can be first converted to the corresponding olefins (XIII), followed by an epoxidation to obtain epoxides (XII) (see e.g. EP-A 291 797).

Process F (Scheme 6):

Scheme 6: Process F - Preparation of Epoxides (IX).

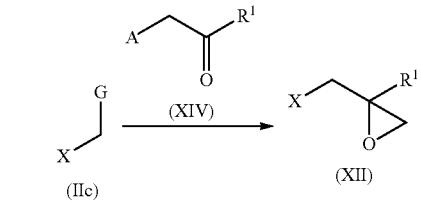

(IIc)    (XII)

G = halogen or hydrogen
A = halogen, $O-SO_2-C_1-C_8$-alkyl or $O-SO_2$-aryl, preferably Cl or Br Alternatively, a compound having the general formula (XII) can be synthesized analogously to methods described in the literature by a coupling reaction of a compound having the corresponding general formula (IIc) with a substrate of the general formula (XIV) (see e.g. DE-A 40 27 608, WO-A 93/02086, WO-A 93/12121, Journal of Organic Chemistry, 2001, 2149-2153 and references cited therein).

Compounds (IIc) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

If G stands for halogen, preferably chloride or bromide, compounds (IIc) are first transformed into Grignard reagents by the reaction with magnesium or with halogen/metal exchange reagents such as isopropylmagnesium halides and subsequently reacted with ketones (XIV) preferably under anhydrous conditions to obtain compounds of the general formula (XV) (see e.g. DE4027608). Alternatively, if G stands for halogen, the halides (IIc) can be converted to the corresponding zinc reagents and subsequently reacted with ketones (XIV) (e.g. ChemComm, 2008, 5824-5826; Journal of Organic Chemistry, 2004, 908-914 and references cited therein).

In an alternative route compounds (IIc) (G=hydrogen) are reacted with compounds (XIV) preferably in the presence of a base. Compounds (IIc) (G=hydrogen) are optionally reacted with a base upfront, e.g. n-butyllithium, lithium-diisopropylamide, lithium bis(trimethylsilyl)amide, sodium bis(trimethylsilyl)amide, potassium bis(trimethylsilyl) amide sodium amide, potassium amide, potassium tert-butoxide, methyl lithium, $TMP_2Zn.2MgCl_2.2LiCl$ (see e.g. Dissertation Albrecht Metzer 2010, University Munich), followed by compounds of the general structure (XIV) preferably under anhydrous conditions. The possible groups for A are, for example, halides which can act as appropriate leaving groups to form the desired compounds (XII) under suitable reaction conditions.

Process G (Scheme 7):

Scheme 7: Process G - Preparation of Alcohol (XI).

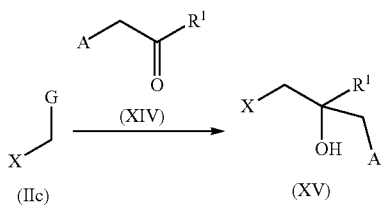

A = halogen, O—SO$_2$—C$_1$-C$_8$-alkyl or O—SO$_2$-aryl, preferably Cl or Br

A compound having the general formula (XV) can be synthesized analogously to methods described in the literature by a coupling reaction of a compound having the corresponding general formula (IIc) with a substrate of the general formula (XIV) (see e.g. DE-A 40 27 608, WO-A 93/02086, WO-A 93/12121, Journal of Organic Chemistry, 2001, 2149-2153).

If G stands for halogen, preferably chloride or bromide, compounds (IIc) are first transformed into Grignard reagents by the reaction with magnesium or with halogen/metal exchange reagents, such as isopropylmagnesium halides, and subsequently reacted with ketones (XIV) preferably under anhydrous conditions to obtain compounds of the general formula (XV) (see e.g. DE4027608). Alternatively, if G stands for halogen, the halides (IIc) can be converted to the corresponding zinc reagents and subsequently reacted with ketones (XIV) (e.g. ChemComm, 2008, 5824-5826; Journal of Organic Chemistry, 2004, 908-914 and references cited therein).

In an alternative route compounds (IIc) (G=hydrogen) are reacted with compounds (XIV) preferably in the presence of a base. Compounds (IIc) (G=hydrogen) are optionally reacted with a base upfront, e.g. n-butyllithium, lithium-diisopropylamide, lithium bis(trimethylsilyl)amide, methyl lithium, followed by compounds of the general structure (XIV) preferably under anhydrous conditions. The possible groups for A are, for example, halides which can act as appropriate leaving groups to form the desired compounds (XV) under suitable reaction conditions.

Process H (Scheme 8):

Scheme 8: Process H - Preparation of compounds (I).

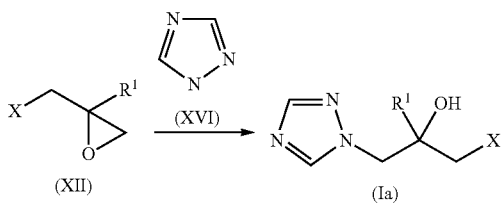

The compounds (XII) obtained according to Process D, E or F can be converted by means of methods described in the literature to the corresponding compounds (Ia) (see e.g. DE-A 40 27 608, EP-A 461 502, DE-A 33 15 681, EP-A 291 797, WO9529901, EP0291797). The starting materials (XII) can be reacted with 1H-1,2,4-triazole (XVI) preferably in the presence of a base, such as potassium carbonate and/or potassium tert-butoxide, and preferably in the presence of an organic solvent, such as DMF, to obtain compounds (Ia).

Process I (Scheme 9):

Scheme 9: Process I - Preparation of compounds (I).

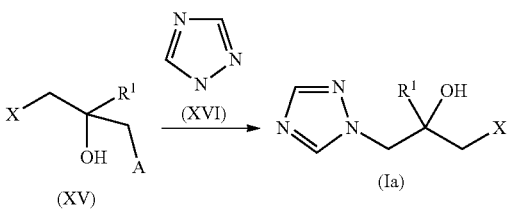

A = halogen, O—SO$_2$—C$_1$-C$_8$-alkyl or O—SO$_2$-aryl, preferably Cl or Br

The compounds (XV) obtained according to Process G can be converted by means of methods described in the literature to the corresponding compounds (Ia) (see e.g. DE-A 40 27 608). The starting materials (XV) can be reacted with 1H-1,2,4-triazole (XVI) preferably in the presence of a base, such as potassium carbonate and/or potassium tert-butoxide, and preferably in the presence of an organic solvent, such as DMF, to obtain compounds (Ia).

Process J (Scheme 10):

Scheme 10: Process J - Preparation of compounds (I).

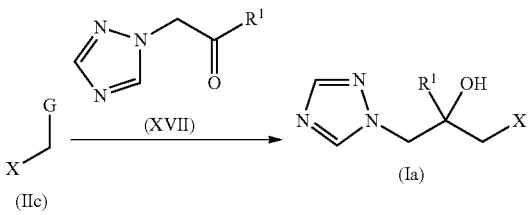

G = halogen or hydrogen

Many triazole ketones of the formula (XVII) are known or can be prepared by literature known methods (e.g. DE-A 24 31 407, DE-A 26 10 022, DE-A 26 38 470, DE-A 42 04 816, EP-A 0 470 463, U.S. Pat. No. 4,486,218, DE-A 31 44 670). The compounds of the formula (XVII) which have not hitherto been described in the literature can be prepared by customary methods. For instance, they are obtained by reacting the corresponding halo-ketones with 1H-1,2,4-triazole in the presence of an acid-binding agent.

In a process according to Scheme 10, for example, ketones (XVII) are reacted with derivatives (IIc), wherein G stands for halogen or hydrogen. If G stands for halogen, compounds (IIc) are first transformed into Grignard reagents by the reaction with magnesium or with transmetallation reagents such as isopropylmagenesium halides and subsequently reacted with ketone (XVII), preferably under anhydrous conditions to obtain compounds (Ia).

In case G stands for hydrogen, compounds (IIc) can be reacted with an organolithium reagent such as methyllithium or n-butyllithium preferably under anhydrous conditions to obtain a lithiated species. Optionally, a base such as lithiumdiisopropylamide or lithium bis(trimethylsilyl)amide, can be used. The obtained intermediates are subsequently reacted with ketones (XVII), preferably under anhydrous conditions to obtain compounds of the general formula (Ia).

Process K (Scheme 11):

Scheme 11: Process K - Preparation of compounds (I).

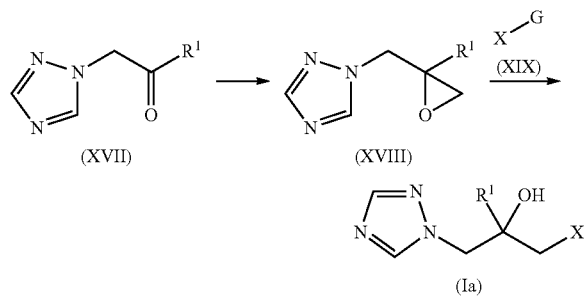

G = halogen or hydrogen

Process L (Scheme 12):

Scheme 12: Process L - Preparation of compounds (I).

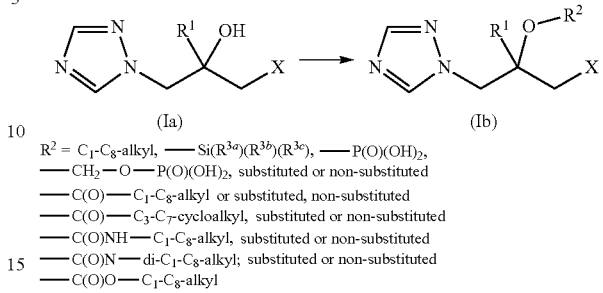

$R^2$ = $C_1$-$C_8$-alkyl, —Si($R^{3a}$)($R^{3b}$)($R^{3c}$), —P(O)(OH)$_2$,
—CH$_2$—O—P(O)(OH)$_2$, substituted or non-substituted
—C(O)—C$_1$-C$_8$-alkyl or substituted, non-substituted
—C(O)—C$_3$-C$_7$-cycloalkyl, substituted or non-substituted
—C(O)NH—C$_1$-C$_8$-alkyl, substituted or non-substituted
—C(O)N—di-C$_1$-C$_8$-alkyl; substituted or non-substituted
—C(O)O—C$_1$-C$_8$-alkyl The compounds (XVII) (Scheme 11) can be converted by means of methods described in the literature to the corresponding compounds (XVIII) (see e.g. DE-A 31 11 238, DE-A 33 07 217). Compounds of the general formula (XVII) are preferably reacted with trimethylsulfoxonium halides, trimethylsulfonium halides, trimethylsulfoxonium methylsulfates or trimethylsulfonium methylsulfates, preferably in the presence of a base, such as sodium hydroxide, to obtain compounds (XVIII).

Compounds (XIX) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

Subsequently, compounds (Ia) can be obtained by the reaction of (XVIII) with (XIX). If G stands for halogen, preferably chloride or bromide, compounds (XIX) are first transformed into Grignard reagents by the reaction with magnesium or with transmetallation reagents such as isopropylmagnesium halides and subsequently reacted with epoxides (XVIII) preferably under anhydrous conditions.

In an alternative route compounds (XIX) (G=hydrogen or halogen) are reacted with compounds (XVIII) preferably in the presence of a base. Compounds (XIX) (G=hydrogen or halogen) are optionally reacted with a base upfront, e.g. n-butyllithium, lithium-di-isopropylamide, lithium bis(trimethylsilyl)amide, methyl lithium, followed by compounds of the general structure (XVIII) preferably under anhydrous conditions to form the desired compounds (Ia).

The compounds (Ia) obtained according to Processes H, I, J or K can be converted by means of methods described in the literature to the corresponding compounds (Ib) (see e.g. DE-A 3202604, JP-A 02101067, EP-A 225 739, CN-A 101824002, FR-A 2802772; WO-A 2012/175119, Bioorganic & Medicinal Chemistry Letters, 7207-7213, 2012; Journal of the American Chemical Society, 19358-19361, 2012, Journal of Organic Chemistry, 9458-9472, 2012; Organic Letters, 554-557, 2013; Journal of the American Chemical Society, 15556, 2012). Compounds of the general structure (Ia) are preferably reacted with alkylhalides, dialkylsulfates, anhydrides, acid chlorides, phosphorylchloride, alkylisocyanate, carbamoyl chlorides, carbono chloridates or imidocarbonates preferably in the presence of a base to obtain compounds (Ib).

General

The processes A to L according to the invention for preparing compounds of the formula (I) are optionally performed using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, n-butyllithium, sec-butyllithium, tert-butyllithium, lithium diisopropylamide, lithium bis(trimethylsilyl)amide, sodium methoxide, ethoxide, n- or i-propoxide, n-, s- or t-butoxide or potassium methoxide, ethoxide, n- or i-propoxide, n-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Useful reaction auxiliaries are, as appropriate, inorganic or organic acids. These preferably include inorganic acids, for example hydrogen fluoride, hydrogen chloride, hydrogen bromide and hydrogen iodide, sulphuric acid, phosphoric acid and nitric acid, and acidic salts such as $NaHSO_4$ and $KHSO_4$, or organic acids, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

The processes A to L according to the invention are optionally performed using one or more diluents. Useful diluents are virtually all inert organic solvents. Unless otherwise indicated for the above described processes A to L, these preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether and methyl tert-butyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylenesulphone and hexamethylphosphoramide and DMPU.

In the processes according to the invention, the reaction temperatures can be varied within a relatively wide range. In general, the temperatures employed are between −78° C. and 250° C., preferably temperatures between −78° C. and 150° C.

The reaction time varies as a function of the scale of the reaction and of the reaction temperature, but is generally between a few minutes and 48 hours.

The processes according to the invention are generally performed under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

After a reaction has ended, the compounds are optionally separated from the reaction mixture by one of the customary separation techniques. If necessary, the compounds are purified by recrystallization or chromatography.

If appropriate, in the processes A to L according to the invention also salts and/or N-oxides of the starting compounds can be used.

The invention further relates to novel intermediates of the compounds of formula (I), which form part of the invention.

Novel intermediates according to the present invention are novel compounds of formula (V)

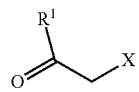

(V)

wherein
X represents a substituted or non-substituted unsaturated 6-membered heterocycle containing 1 or 2 nitrogen atom(s) as heteroatom(s) or a benzannulated derivative thereof; and
$R^1$ represents a substituted or non-substituted 1-halogencyclopropyl, 1-halogen-2-methylpropan-2-yl or 2-halogen-propan-2-yl;
and its salts or N-oxides.

X preferably represents a substituted or non-substituted 2-pyridinyl, 3-pyridinyl, 4-pyridinyl, quinoline-3-yl or quinoline-2-yl.

X more preferably represents a substituted or non-substituted 2-pyridinyl, 3-pyridinyl, 4-pyridinyl or quinoline-2-yl.

X most preferably represents a substituted or non-substituted 3-pyridinyl, 4-pyridinyl, quinoline-3-yl or quinoline-2-yl.

X also most preferably represents a substituted or non-substituted 3-pyridinyl, 4-pyridinyl or quinoline-2-yl.

X also more preferably represents a substituted or non-substituted 2-pyridinyl.

Preferably in 1-halogencyclopropyl, 1-halogen-2-methylpropan-2-yl or 2-halogen-propan-2-yl for $R^1$ halogen is selected from fluorine or chlorine.

Further novel intermediates according to the present invention are novel compounds of formula (V)

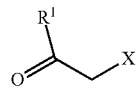

(V)

wherein
X represents a substituted or non-substituted 3-pyridinyl or 4-pyridinyl or a benzannulated derivative thereof; and
$R^1$ represents a substituted or non-substituted 1-$C_1$-$C_8$-alkylcyclopropyl, 2-$C_1$-$C_8$-alkylcyclopropyl, $C_1$-$C_8$-haloalkyl, 1-$C_1$-$C_8$-alkylcyclohexyl, 1-arylcyclopropyl or 2-arylcyclopropyl;
and its salts or N-oxides.

For the compounds of formula (V) preferably
X represents a substituted or non-substituted 3-pyridinyl or 4-pyridinyl or a benzannulated derivative thereof; and
$R^1$ represents a substituted or non-substituted 1-$C_1$-$C_8$-alkylcyclopropyl, 2-$C_1$-$C_8$-alkylcyclopropyl, 1-arylcyclopropyl or 2-arylcyclopropyl.

Further novel intermediates according to the present invention are novel expoxides of formula (XII)

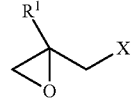

(XII)

wherein

X represents a substituted or non-substituted unsaturated 6-membered heterocycle containing 1 or 2 nitrogen atom(s) as heteroatom(s) or a benzannulated derivative thereof; and $R^1$ represents $C_1$-$C_8$-haloalkyl; $C_2$-$C_8$-halooalkenyl; $C_2$-$C_8$-haloalkynyl; $C_3$-$C_7$-halocycloalkyl-$C_1$-$C_4$-alkyl; $C_3$-$C_7$-halocycloalkyl-$C_1$-$C_4$-haloalkyl; $C_3$-$C_7$-cycloalkyl-$C_1$-$C_4$-haloalkyl; substituted or non-substituted $C_3$-$C_7$-cycloalkyl; substituted or non-substituted $C_3$-$C_7$-cycloalkenyl; substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; substituted or non-substituted heterocycloalkyl-$C_1$-$C_8$-alkyl;

and its salts or N-oxides.

Preferred radical definitions for X and $R^1$ have already been given above for the compounds of formula (I). Such preferred radical definitions shall also apply for the epoxides of formula (XII).

Further novel intermediates according to the present invention are novel alcohols of formula (XV)

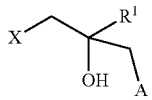

(XV)

wherein

X represents a substituted or non-substituted unsaturated 6-membered heterocycle containing 1 or 2 nitrogen atom(s) as heteroatom(s) or a benzannulated derivative thereof; and $R^1$ represents $C_1$-$C_8$-haloalkyl; $C_2$-$C_8$-halooalkenyl; $C_2$-$C_8$-haloalkynyl; $C_3$-$C_7$-halocycloalkyl-$C_1$-$C_4$-alkyl; $C_3$-$C_7$-halocycloalkyl-$C_1$-$C_4$-haloalkyl; $C_3$-$C_7$-cycloalkyl-$C_1$-$C_4$-haloalkyl; substituted or non-substituted $C_3$-$C_7$-cycloalkyl; substituted or non-substituted $C_3$-$C_7$-cycloalkenyl; substituted or non-substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; substituted or non-substituted heterocycloalkyl-$C_1$-$C_8$-alkyl;

and

A represents chlorine, bromine, iodine, O—$SO_2$—$C_1$-$C_8$-alkyl or O—$SO_2$-aryl, preferably chlorine or bromine;

and its salts or N-oxides.

Preferred radical definitions for X and $R^1$ have already been given above for the compounds of formula (I). Such preferred radical definitions shall also apply for the alcohols of formula (XV).

The compounds of the formula (I) according to the invention can be converted into physiologically acceptable salts, e.g. as acid addition salts or metal salt complexes.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, maleic acid, fumaric acid, tartaric acid, sorbic acid oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, 1,5-naphthalenedisulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

The acid addition salts of the compounds of the formula (I) can be obtained in a simple manner by customary methods for forming salts, for example by dissolving a compound of the formula (I) in a suitable inert solvent and adding the acid, for example hydrochloric acid, and be isolated in a known manner, for example by filtration, and, if required, be purified by washing with an inert organic solvent.

Suitable anions of the salts are those which are preferably derived from the following acids: hydrohalic acids, such as, for example, hydrochloric acid and hydrobromic acid, furthermore phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtration, and, if required, be purified by recrystallization.

Salts of the intermediates can also be prepared according to the processes mentioned above for the salts of compounds of formula (I).

N-oxides of compounds of the formula (I) or intermediates thereof can be obtained in a simple manner by customary processes, for example by N-oxidation with hydrogen peroxide ($H_2O_2$), peracids, for example peroxy sulfuric acid or peroxy carboxylic acids, such as meta-chloroperoxybenzoic acid or peroxymonosulfuric acid (Caro's acid).

Composition/Formulation

The present invention further relates to a crop protection composition for controlling harmful microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyryl-phenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fatty acids and their salts as well as fluoroorganic substances and mixtures thereof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;* diseases caused by rust disease pathogens, for example *Gymnosporangium* species, for example *Gymnosporangium*

*sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite*, *P. triticina*, *P. graminis* or *P. striiformis*; *Uromyces* species, for example *Uromyces appendiculatus*; diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnate*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnate*; *Verticillium* species, caused for example by *Verticillium dahliae*;

cancers, galls and witches' broom caused, for example, by *Nectria* species, for example *Nectria galligena*; wilt diseases caused, for example, by *Monilinia* species, for example *Monilinia laxa*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; *Eutypa* dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plamodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera* glycini), frogeye leaf spot (*Cercospora sojina*), leptosphaerulina leaf spot (*Leptosphaerulina trifolii*), phyllostica leaf spot (*Phyllosticta* sojaecola), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); Solanaceae sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Plant Growth Regulation

In some cases, the inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active compounds according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m², number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:
improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying; further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;
further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;
and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech. J. Food Sci.* Vol. 21, No. 3: 91-96, 2000). Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further comprises a method for treating seed.

The invention further relates to seed which has been treated by one of the methods described in the previous paragraph. The inventive seeds are employed in methods for the protection of seed from harmful microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272, 417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are non-ionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive active ingredients or compositions can also be used in the protection of materials, for protection of industrial materials against attack and destruction by harmful microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids. Examples of nematode or insect resistant plants are described in e.g. U.S. patent application Ser. Nos. 11/765,491, 11/765,494, 10/926,819, 10/782,020, 12/032,479, 10/783,417, 10/782,096, 11/657,964, 12/192, 904, 11/396,808, 12/166,253, 12/166,239, 12/166,124, 12/166,209, 11/762,886, 12/364,335, 11/763,947, 12/252, 453, 12/209,354, 12/491,396, 12/497,221, 12/644,632, 12/646,004, 12/701,058, 12/718,059, 12/721,595, 12/638, 591.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (*Science* 1983, 221, 370-371), the CP4 gene of the bacterium *Agrobacterium* sp. (*Curr. Topics Plant Physiol.* 1992, 7, 139-145), the genes encoding a *Petunia* EPSPS (*Science* 1986, 233, 478-481), a Tomato EPSPS (*J. Biol. Chem.* 1988, 263, 4280-4289), or an *Eleusine* EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 02/036782, WO 03/092360, WO 2005/012515 and WO 2007/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. No. 11/517,991, 10/739,610, 12/139,408, 12/352,532, 11/312,866, 11/315,678, 12/421, 292, 11/400,598, 11/651,752, 11/681,285, 11/605,824, 12/468,205, 11/760,570, 11/762,526, 11/769,327, 11/769, 255, 11/943,801 or 12/362,774. Plants comprising other genes that confer glyphosate tolerance, such as decarboxylase genes, are described in e.g. U.S. patent application Ser. No. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (*Weed Science* 2002, 50, 700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782 and U.S. Patent Application 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1 999 141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (*Nat. Biotechnol.* 2001, 19, 668-72; *Applied Environm. Microbiol.* 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP-A 2 300 618); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Applications 61/126,083 and 61/195,019), or the binary toxin made up of the VIP3 protein and the Cry2Aa or Cry2Ab or Cry2Ae proteins (U.S. patent application Ser. No. 12/214,022 and EP-A 2 300 618).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO 2006/045633, EP-A 1 807 519, or EP-A 2 018 431.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP-A 1 794 306, WO 2006/133827, WO 2007/107326, EP-A 1 999 263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP-A 0 571 427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, WO 2008/017518, WO 2008/080630, WO 2008/080631, WO 2008/090008, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936, WO 2010/012796, WO 2010/003701, 2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP-A 0 663 956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, U.S. Pat. No. 5,908,975 and EP-A 0 728 213, 3) transgenic plants which produce hyaluronan, as for example disclosed in WO 2006/032538, WO 2007/039314, WO 2007/039315, WO 2007/039316, JP-A 2006-304779, and WO 2005/012529.
4) transgenic plants or hybrid plants, such as onions with characteristics such as 'high soluble solids content', 'low pungency' (LP) and/or 'long storage' (LS), as described in U.S. patent application Ser. No. 12/020,360.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549.
b) Plants, such as cotton plants, containing an altered form of rsw2 or rsw3 homologous nucleic acids as described in WO 2004/053219.
c) Plants, such as cotton plants, with increased expression of sucrose phosphate synthase as described in WO 01/17333.
d) Plants, such as cotton plants, with increased expression of sucrose synthase as described in WO 02/45485.

e) Plants, such as cotton plants, wherein the timing of the plasmodesmatal gating at the basis of the fiber cell is altered, e.g. through downregulation of fiber-selective β-1,3-glucanase as described in WO 2005/017157, or as described in WO 2009/143995.
f) Plants, such as cotton plants, having fibers with altered reactivity, e.g. through the expression of N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for nonregulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Application Rates and Timing

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions comprising a compound according to formula (I) can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

EXAMPLES

Preparation Examples

Preparation of Compounds of the Formula (I-5) According to Process H

Preparation of 2-(1-chlorocyclopropyl)-1-(3-chloropyridin-4-yl)-3-(1H-1,2,4-triazol-1-yl)propan-2-ol (I-5)

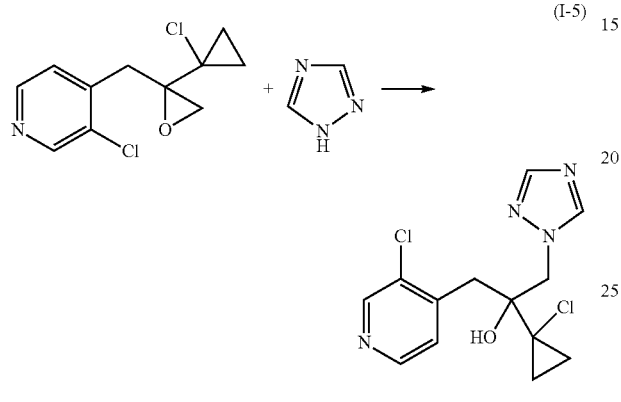

(I-5)

To a solution of 1H-1,2,4-triazole (162 mg, 3 eq, 2.35 mmol) in 2.5 mL dimethylformamide was added potassium carbonate (326 mg, 3 eq, 2.35 mmol) and a solution of 3-chloro-4-{[2-(1-chlorocyclopropyl)oxiran-2-yl]methyl}pyridine (300 mg, 0.78 mmol) in 0.5 mL dimethylformamide Thereafter 5 mg potassium tert-butylate was added and the mixture was stirred for 5 h at 40° C. Thereafter the reaction mixture was evaporated in vacuo and treated with ethyl acetate. After filtration and evaporation of the solvent the crude product was purified by chromatography over silica using a 1:1 mixture of ethyl acetate/cyclohexane as eluent. After evaporation of the solvent 100 mg (40%) of 2-(1-chlorocyclopropyl)-1-(3-chloropyridin-4-yl)-3-(1H-1,2,4-triazol-1-yl)propan-2-ol were obtained as solid.

MS (ESI): 313.0 ([M+1]$^+$)

Preparation of Intermediates of the Formula (XII-3) According to Process D

Preparation of 3-chloro-4-{[2-(1-chlorocyclopropyl)oxiran-2-yl]methyl}pyridine (XII-3)

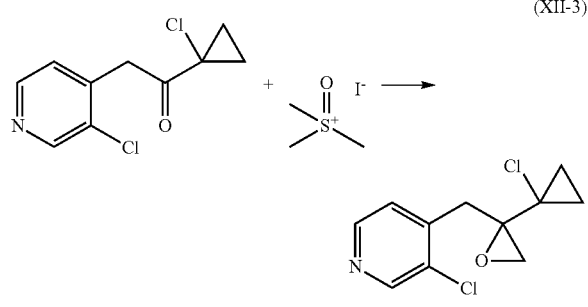

(XII-3)

A mixture of trimethylsulfoxonium chloride (330 mg, 2 eq, 1.5 mmol), sodium hydroxide (793 mg, 12 eq, 45% weight in H$_2$O) and hexadecyltrimethylammoniumbromide (3 mg, 0.01 eq) in 1.4 mL dichloromethane was stirred for 10 min at ambient temperature. Thereafter, 1-(1-chlorocyclopropyl)-2-(3-chloropyridin-4-yl)ethanone (180 mg, 1 eq, 0.74 mmol) was added and the mixture was stirred for 4 h at 45° C. The obtained suspension was diluted with dichloromethane and filtered. The filtrate was evaporated and purified by column chromatography over silica gel (eluent cyclohexane/ethyl acetate gradient). After evaporation of the solvent 70 mg (35%) of 3-chloro-4-{[2-(1-chlorocyclopropyl)oxiran-2-yl]methyl}pyridine were obtained as colourless oil.

MS (ESI): 244.0 ([M+H]$^+$)

Preparation of Intermediates of the Formula (XII-3) According to Process F

Preparation of 3-chloro-4-{[2-(1-chlorocyclopropyl)oxiran-2-yl]methyl}pyridine (XII-3)

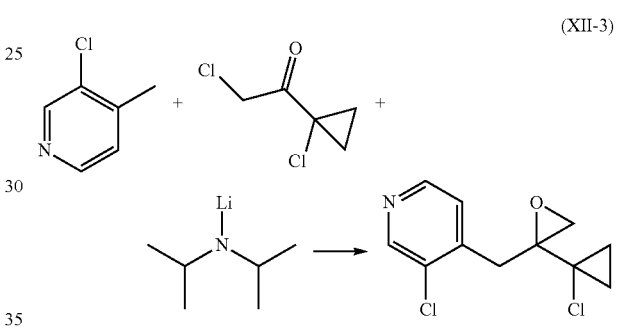

(XII-3)

To a solution of lithium diisopropylamide (30 mL, 2M in THF) at −70° C. is added under argon a solution of 3-chloro-4-methylpyridine (6.38 g, 1 eq, 50 mmol) in 25 mL THF. The mixture is stirred for 5 min at −70° C. and then allowed to reach −30° C. Thereafter the mixture is cooled down to −70° C. and a solution of 2-chloro-1-(1-chlorocyclopropyl)ethanone (9.18 g, 1.2 eq, 60 mmol) in 25 mL THF is added. Then the mixture is allowed to reach ambient temperature and stirred for 1 h. Thereafter the mixture is cooled to 0° C. and saturated aqueous ammonium chloride solution is added. After extraction with ethyl acetate and evaporation of the solvent the crude material is purified via column chromatography over silica gel (eluent cyclohexane/ethyl acetate gradient). After evaporation of the solvent 10 g (73%) of 3-chloro-4-{[2-(1-chlorocyclopropyl)oxiran-2-yl]methyl}pyridine are obtained as colourless oil.

Preparation of Intermediates of the Formula (V-3) According to Process A

Preparation of 1-(1-chlorocyclopropyl)-2-(2-chloropyridin-3-yl)ethanone (V-3)

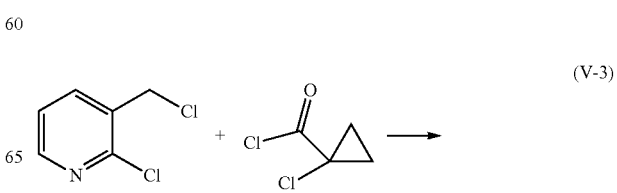

(V-3)

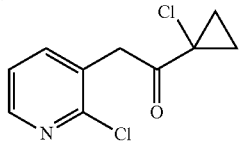
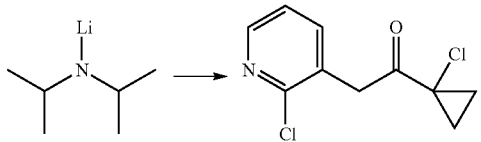

To a suspension of zinc (2.72 g, 1.5 eq) in THF (40 mL) was added dropwise under argon a solution of 2-chloro-3-chloromethylpyridine (2.25 g, 0.5 eq) in THF (15 mL). Dibromoethane (100 μL) was then added to the reaction mixture, followed by a solution of 2-chloro-3-chloromethylpyridine (2.25 g, 0.5 eq) in THF (15 mL). The mixture was stirred at room temperature for 1 h. A suspension of 1-chlorocyclopropyl carbonyl chloride (3.86 g, 1 eq) and dichlorobis(triphenylphosphine)palladium (II) (1.17 g, 0.06 eq) in THF (30 mL) was then added dropwise and the mixture was stirred at 65° C. for 4 h30. The mixture was then stirred at room temperature and heated again to 65° C. for 1 h30. The mixture was filtered and the filtrate was poured over water (300 mL) and ethyl acetate (100 mL) was then added. The suspension was filtered and the 2 layers were separated. The water layer was extracted with ethyl acetate (2*100 mL). The organic phase were combined, dried over magnesium sulfate, filtered and evaporated. The residue was purified by chromatography on silica gel to afford 1-(1-chlorocyclopropyl)-2-(2-chloropyridin-3-yl)ethanone as a yellow oil (3.79 g, 56%).

MS (ESI): 230.0 ([M+H]$^+$)

Preparation of Intermediates of the Formula (V-3) According to Process B

Preparation of 1-(1-chlorocyclopropyl)-2-(2-chloropyridin-3-yl)ethanone (V-3)

To a solution of lithium diisopropylamide (32 mL, 1.3 eq, 65 mmol, 2M in THF) in 40 mL THF at −70° C. is added under argon a solution of 2-chloro-3-methylpyridine (6.38 g, 1 eq, 50 mmol) in 10 mL THF. The mixture is stirred for 15 min at −70° C. and then allowed to reach −30° C. In a separate flask a solution of ethyl 1-chlorocyclopropanecarboxylate (11 g, 1.5 eq, 75 mmol) in 25 mL THF is cooled to −30° C. To this solution the methylpyridine solution is slowly added at −30° C. Thereafter the mixture is allowed to reach ambient temperature and stirred for 1 h. Thereafter the mixture is cooled to 0° C. and saturated aqueous ammonium chloride solution is added. After extraction with ethyl acetate and evaporation of the solvent the crude material is purified via column chromatography over silica gel (eluent cyclohexane/ethyl acetate gradient). After evaporation of the solvent 3.1 g (26%) of 1-(1-chlorocyclopropyl)-2-(2-chloropyridin-3-yl)ethanone are obtained as colourless oil.

The exemplary compounds according to the invention listed in Table 1, 2 and 3 have been synthesized analogous to the above mentioned processes.

The following Table 1 illustrates in a non-limiting manner examples of compounds according to formula (I).

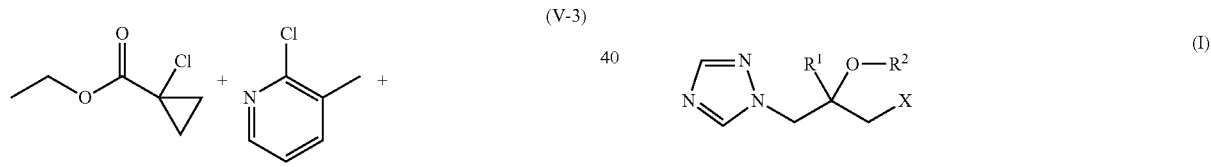

TABLE 1

| Ex N° | R¹ | R² | X | LogP |
|---|---|---|---|---|
| I-1 | 1-chlorocyclopropyl | H | quinolin-2-yl | 1.64[a] |
| I-2 | 1-chlorocyclopropyl | H | 3-chloropyridin-2-yl | 2.28[a] |
| I-3 | 1-chlorocyclopropyl | H | 2-chloropyridin-3-yl | 1.78[a] |
| I-4 | 1-chlorocyclopropyl | H | 6-chloropyridin-3-yl | 1.84[a] |
| I-5 | 1-chlorocyclopropyl | H | 3-chloropyridin-4-yl | 1.75[b]; 1.67[a] |
| I-6 | 1,3-difluoro-2-methylpropan-2-yl | H | 3-chloropyridin-4-yl | 1.54[a] |
| I-7 | 1-fluorocyclopropyl | H | 3-chloropyridin-4-yl | 1.29[a] |
| I-8 | 1-methylcyclopropyl | H | 2-chloropyridin-3-yl | 1.73[a] |
| I-9 | 1-chlorocyclopropyl | H | 6-chloropyrazin-2-yl | 1.72[a] |
| I-10 | 1-chlorocyclopropyl | H | 3-chloro-5-methylpyrazin-2-yl | 2.05[a] |
| I-11 | 1-chlorocyclopropyl | H | pyrazin-2-yl | 1.13[a] |
| I-12 | 2-fluorobenzyl | H | 3-chloropyridin-4-yl | 1.96[a] |
| I-13 | 6-chloropyridin-3-yl | H | 3-chloropyridin-4-yl | 1.26[a] |
| I-14 | 2-chloropyridin-3-yl | H | 3-chloropyridin-4-yl | 1.23[a] |
| I-15 | 3-chlorobenzyl | H | 3-chloropyridin-4-yl | 2.27[a] |
| I-16 | 1-(4-chlorophenoxy)ethyl | H | 2-chloropyridin-3-yl | |
| I-17 | 1-chlorocyclopropyl | H | 4,6-dichloropyridin-2-yl | 2.76[a] |
| I-18 | 1-chlorocyclopropyl | H | 3-fluoropyridin-4-yl | 1.29[a] |
| I-19 | 1-fluorocyclopropyl | H | 3-fluoropyridin-4-yl | 0.91[a] |

TABLE 1-continued

| Ex N° | R¹ | R² | X | LogP |
|---|---|---|---|---|
| I-20 | 2-fluorobenzyl | H | 3-fluoropyridin-4-yl | 1.63[a] |
| I-21 | 1,3-difluoro-2-methylpropan-2-yl | H | 3-fluoropyridin-4-yl | 1.27[a] |
| I-22 | 3-chlorobenzyl | H | 3-fluoropyridin-4-yl | 2.00[a] |
| I-23 | 2-chloropyridin-3-yl | H | 3-fluoropyridin-4-yl | 0.91[a] |
| I-24 | 6-chloropyridin-3-yl | H | 3-fluoropyridin-4-yl | 0.99[a] |
| I-25 | 1-fluorocyclopropyl | H | 2-chloropyridin-3-yl | 1.42[a] |
| I-26 | 1-chlorocyclopropyl | H | 2,6-dichloropyridin-4-yl | 2.54[a] |
| I-27 | 1-chlorocyclopropyl | H | quinolin-4-yl | 1.00[a] |
| I-28 | 1-chlorocyclopropyl | Si(Me)3 | pyrazin-2-yl | 2.75[a] |
| I-29 | 1-chlorocyclopropyl | H | 6-chloropyridin-2-yl | 2.18[a] |
| I-30 | 1-chlorocyclopropyl | H | 3-chloropyrazin-2-yl | 1.86[a] |
| I-31 | 1-chlorocyclopropyl | H | 5,6-dichloropyridin-2-yl | 2.66[a] |
| I-32 | 1-chlorocyclopropyl | H | 6-chloro-4-[(5,6-dichloropyridin-2-yl)methyl]pyridin-2-yl | 3.58[a] |
| I-33 | 1-fluorocyclopropyl | H | 2-chloropyridin-4-yl | 1.44[a] |
| I-34 | 2-chloropyridin-3-yl | H | 2-chloropyridin-4-yl | 1.35[a] |
| I-35 | 2-fluorobenzyl | H | 2-chloropyridin-4-yl | 2.06[a] |
| I-36 | 1,3-difluoro-2-methylpropan-2-yl | H | 2-chloropyridin-4-yl | 1.66[a] |
| I-37 | 3-chlorobenzyl | H | 2-chloropyridin-4-yl | 2.42[a] |
| I-38 | 6-chloropyridin-3-yl | H | 2-chloropyridin-4-yl | 1.38[a] |
| I-39 | 1-chlorocyclopropyl | H | 2-chloropyridin-4-yl | 1.76[a] |
| I-40 | 1-chlorocyclopropyl | H | 2-chloro-5-fluoropyridin-4-yl | 2.06[a] |
| I-41 | 1-fluorocyclopropyl | H | 2-chloro-5-fluoropyridin-4-yl | 1.66[a] |
| I-42 | 6-chloropyridin-3-yl | H | 2-chloro-5-fluoropyridin-4-yl | 1.60[a] |
| I-43 | 2-chloropyridin-3-yl | H | 2-chloro-5-fluoropyridin-4-yl | 1.57[a] |
| I-44 | 1,3-difluoro-2-methylpropan-2-yl | H | 2-chloro-5-fluoropyridin-4-yl | 1.89[a] |
| I-45 | 1-chlorocyclopropyl | H | 3-chloropyridazin-4-yl | 1.31[a] |
| I-46 | 1-chlorocyclopropyl | H | 3,6-dichloropyridazin-4-yl | 1.92[a] |
| I-47 | 1-chlorocyclopropyl | H | 4-chloropyridin-2-yl | 2.02[a] |
| I-48 | 1-chlorocyclopropyl | H | 6-methylpyridin-2-yl | 0.52[a] |
| I-49 | 1-methylcyclopropyl | H | 3-chloropyridin-4-yl | 1.57[a] |
| I-50 | 1-chlorocyclopropyl | H | pyrimidin-4-yl | 1.10[a] |
| I-51 | 1-chlorocyclopropyl | H | 2-fluoropyridin-3-yl | 1.64[a] |
| I-52 | 1-chlorocyclopropyl | H | 4-methylpyridin-2-yl | 0.52[a] |
| I-53 | 1-chlorocyclopropyl | H | 2,6-dichloropyridin-3-yl | 2.55[a] |
| I-54 | 1-chlorocyclopropyl | H | 3-iodopyrazin-2-yl | 2.07[a] |
| I-55 | 1-chlorocyclopropyl | H | 3-chloro-6-(4-chlorophenoxy)pyridazin-4-yl | 3.08[a] |
| I-56 | 1-chlorocyclopropyl | H | 6-(4-chlorophenoxy)pyrazin-2-yl | 2.88[a] |
| I-57 | 1-chlorocyclopropyl | H | 5,6-dichloropyrimidin-4-yl | 2.28[a] |
| I-58 | 1-chlorocyclopropyl | H | 2,5-dichloropyridin-4-yl | 2.53[a] |
| I-59 | 2-chloropyridin-3-yl | H | 2-chloro-3-fluoropyridin-4-yl | 1.54[a] |
| I-60 | 1-chlorocyclopropyl | H | 2-chloro-3-fluoropyridin-4-yl | 2.02[a] |
| I-61 | 1,3-difluoro-2-methylpropan-2-yl | H | 2-chloro-3-fluoropyridin-4-yl | 1.87[a] |
| I-62 | 1-fluorocyclopropyl | H | 3,5-dichloropyridin-4-yl | 1.86[a] |
| I-63 | 6-chloropyridin-3-yl | H | 3,5-dichloropyridin-4-yl | 1.89[a] |
| I-64 | 2-fluorobenzyl | H | 5-chloro-2-fluoropyridin-4-yl | 2.46[a] |
| I-65 | 1-fluorocyclopropyl | H | 5-chloro-2-fluoropyridin-4-yl | 1.77[a] |
| I-66 | 1,5-dimethyl-1H-pyrazol-3-yl | H | 3-chloropyridin-4-yl | 0.84[a] |
| I-67 | 1-chlorocyclopropyl | H | 5-chloropyridin-2-yl | 2.23[a] |
| I-68 | 2-(2-chlorophenyl)ethyl | H | 3-chloropyridin-4-yl | 2.29[a] |
| I-69 | 2-(4-chlorophenyl)ethyl | H | 3-chloropyridin-4-yl | 2.40[a] |
| I-70 | 2-(4-chlorophenoxy)propan-2-yl | H | 3-chloropyridin-4-yl | 2.84[a] |
| I-71 | 1-chlorocyclopropyl | H | 3-bromopyrazin-2-yl | 1.96[a] |
| I-72 | 1-chlorocyclopropyl | H | 3-methoxypyrazin-2-yl | 1.88[a] |
| I-73 | 2-fluorobenzyl | H | 2-chloro-5-fluoropyridin-4-yl | 2.34[a] |
| I-74 | 3-chlorobenzyl | H | 2-chloro-5-fluoropyridin-4-yl | 2.69[a] |
| I-75 | 4-fluorobenzyl | H | 3-chloropyridin-4-yl | 1.93[a] |
| I-76 | 2-fluoropropan-2-yl | H | 3-chloropyridin-4-yl | 1.20[a] |
| I-77 | Cyclobutyl | H | 3-chloropyridin-4-yl | 1.46[a] |
| I-78 | 1-phenylcyclopropyl | H | 3-chloropyridin-4-yl | 2.23[a] |
| I-79 | (4-fluorophenoxy)methyl | H | 3-chloropyridin-4-yl | 1.86[a] |
| I-80 | dibenzo[b,d]furan-2-yl | H | 3-chloropyridin-4-yl | 2.40[a] |
| I-81 | 1-chlorocyclopropyl | H | 3-(trifluoromethyl)pyridin-4-yl | 2.08[a] |
| I-82 | 1-chlorocyclopropyl | H | 2,3-dichloropyridin-4-yl | 2.39[a] |
| I-83 | 1-chlorocyclopropyl | H | 2,5-dichloropyridin-3-yl | 2.53[a] |
| I-84 | 1-chlorocyclopropyl | H | 2-chloro-8-methylquinolin-3-yl | 3.53[a] |
| I-85 | 2-fluorobenzyl | H | 2-chloro-3-fluoropyridin-4-yl | 1.73[a] |
| I-86 | 6-chloropyridin-3-yl | H | 2-chloro-3-fluoropyridin-4-yl | 1.23[a] |
| I-87 | 1-fluorocyclopropyl | H | 2-chloro-3-fluoropyridin-4-yl | 1.23[a] |
| I-88 | 3-chlorobenzyl | H | 2-chloro-3-fluoropyridin-4-yl | 2.02[a] |
| I-89 | 1-chlorocyclopropyl | H | 5-chloro-2-fluoropyridin-4-yl | 2.30[a] |

TABLE 1-continued

| Ex N° | R¹ | R² | X | LogP |
|---|---|---|---|---|
| I-90 | 1-chloro-2-methylpropan-2-yl | H | 3-chloropyridin-4-yl | 1.96[b]; 1.76[a] |
| I-91 | 2-(4-fluorophenoxy)propan-2-yl | H | 3-chloropyridin-4-yl | 2.60[b]; 2.48[a] |
| I-92 | 1-chlorocyclopropyl | H | 2-chloroquinolin-4-yl | 2.69[a] |
| I-93 | 1-methylcyclopropyl | H | 3-chloropyridazin-4-yl | 1.28[a] |
| I-94 (*) | 1-chlorocyclopropyl | H | 2-chloropyridin-3-yl | 1.79[b]; 1.81[a] |
| I-95 (*) | 1-chlorocyclopropyl | H | 2-chloropyridin-3-yl | 1.79[b]; 1.81[a] |
| I-96 | 1-chlorocyclopropyl | H | 3,6-dichloropyridin-2-yl | 2.73[a] |
| I-97 | 1-chlorocyclopropyl | H | 3,5-dichloropyridin-2-yl | 2.88[a] |

(*) Ex I-94 and I-95 are the 2 enantiomers of Ex I-3 Optical rotation: I-94 is the (−) Isomer −8.1° (MeOH) I-95 is the (+) Isomer +9.6° (MeOH)

The following Table 2 illustrates in a non-limiting manner examples of compounds according to formula (V).

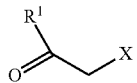

(V)

TABLE 2

| Ex N° | R¹ | X | LogP |
|---|---|---|---|
| V-1 | 1-chlorocyclopropyl | quinolin-2-yl | 3.39[a] |
| V-2 | 1-chlorocyclopropyl | 3-chloropyridin-2-yl | 2.40[a] |
| V-3 | 1-chlorocyclopropyl | 2-chloropyridin-3-yl | 2.21[b]; 2.20[a] |
| V-4 | 1-chlorocyclopropyl | 3-chloropyridin-4-yl | 2.13[a] |
| V-5 | 1-chlorocyclopropyl | 2,6-dichloropyridin-4-yl | 3.25[a] |
| V-6 | 1-chlorocyclopropyl | 6-chloropyridin-3-yl | 2.30[b]; 2.34[a] |
| V-7 | 1-fluorocyclopropyl | 3-chloropyridin-4-yl | 1.76[a] |
| V-8 | 2-fluoropropan-2-yl | 3-chloropyridin-4-yl | 1.97[a] |
| V-9 | 1-methylcyclopropyl | 2-chloropyridin-3-yl | 1.96[a] |
| V-10 | 1-phenylcyclopropyl | 2-chloropyridin-3-yl | 3.00[a] |
| V-11 | 1-methylcyclopropyl | 3-chloropyridin-4-yl | 1.85[a] |
| V-12 | 1-methylcyclohexyl | 3-chloropyridin-4-yl | 3.23[a] |
| V-13 | 1-chlorocyclopropyl | quinolin-3-yl | 1.60[a] |
| V-14 | 1-fluorocyclopropyl | 2-chloropyridin-3-yl | |
| V-15 | 1,3-difluoro-2-(fluoromethyl)propan-2-yl | 2-chloropyridin-3-yl | 1.98[a] |
| V-16 | 1-chlorocyclopropyl | 2-fluoropyridin-3-yl | 2.07[a] |
| V-17 | 1-chlorocyclopropyl | 2,6-dichloropyridin-3-yl | 3.19[a] |
| V-18 | 1-chlorocyclopropyl | 2-chloro-8-methylquinolin-3-yl | 4.14[a] |
| V-19 | 1-chlorocyclopropyl | pyridin-3-yl | 0.23[a] |
| V-20 | 1-chlorocyclopropyl | 2,4-dichloropyridin-3-yl | 2.96[a] |
| V-21 | 1-chlorocyclopropyl | 2,5-dichloropyridin-3-yl | 3.12[a] |

The following Table 3 illustrates in a non-limiting manner examples of compounds according to formula (XII).

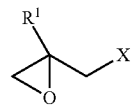

(XII)

TABLE 3

| Ex N° | R¹ | X | LogP |
|---|---|---|---|
| XII-1 | 1-chlorocyclopropyl | quinolin-2-yl | 1.74[a] |
| XII-2 | 1-chlorocyclopropyl | 6-chloropyridin-3-yl | 2.83[b]; 2.84[a] |
| XII-3 | 1-chlorocyclopropyl | 3-chloropyridin-4-yl | 2.71[b]; 2.60[a] |
| XII-4 | 1-chlorocyclopropyl | 3-chloropyridin-2-yl | 2.69[a] |
| XII-5 | 1-chlorocyclopropyl | 2-chloropyridin-3-yl | 2.69[a] |
| XII-6 | 1-chlorocyclopropyl | 3-fluoropyridin-4-yl | 2.13[a] |
| XII-7 | 1-fluorocyclopropyl | 3-fluoropyridin-4-yl | 1.63[a] |
| XII-8 | 1,3-difluoro-2-methylpropan-2-yl | 3-fluoropyridin-4-yl | 1.79[a] |
| XII-9 | 1-fluorocyclopropyl | 2-chloropyridin-4-yl | 2.27[a] |
| XII-10 | 1,3-difluoro-2-methylpropan-2-yl | 2-chloropyridin-4-yl | 2.38[a] |
| XII-11 | 1-chlorocyclopropyl | 2-chloropyridin-4-yl | 2.80[a] |
| XII-12 | 1,3-difluoro-2-methylpropan-2-yl | 2-chloro-5-fluoropyridin-4-yl | 2.69[a] |
| XII-13 | 1-fluorocyclopropyl | 2-chloro-5-fluoropyridin-4-yl | 2.57[a] |
| XII-14 | 1-chlorocyclopropyl | 2-chloro-5-fluoropyridin-4-yl | 3.15[a] |
| XII-15 | 2-chloropropan-2-yl | 3-chloropyridin-4-yl | 2.57[a] |
| XII-16 | 1-chlorocyclopentyl | 3-chloropyridin-4-yl | 3.42[a] |
| XII-17 | 1-chlorocyclohexyl | 3-chloropyridin-4-yl | 3.80[a] |
| XII-18 | 1,3-difluoro-2-methylpropan-2-yl | 3-chloropyridin-4-yl | 2.16[a] |
| XII-19 | 1-fluorocyclopropyl | 3-chloropyridin-4-yl | 2.06[a] |
| XII-20 | 1-chlorocyclopropyl | 5-chloro-2-fluoropyridin-4-yl | 3.41[a] |
| XII-21 | 1-fluorocyclopropyl | 5-chloro-2-fluoropyridin-4-yl | 2.80[a] |
| XII-22 | 1,3-difluoro-2-methylpropan-2-yl | 5-chloro-2-fluoropyridin-4-yl | 2.84[a] |
| XII-23 | 1-fluorocyclopropyl | 2-chloropyridin-3-yl | 2.18[a] |
| XII-24 | 1-chlorocyclopropyl | 2,6-dichloropyridin-4-yl | 3.80[a] |
| XII-25 | 1-chlorocyclopropyl | pyrimidin-4-yl | 1.44[a] |

TABLE 3-continued

| Ex N° | R¹ | X | LogP |
|---|---|---|---|
| XII-26 | 1-chlorocyclopropyl | 2-chloro-3-fluoropyridin-4-yl | 3.11[a] |
| XII-27 | 1,3-difluoro-2-methylpropan-2-yl | 2-chloro-3-fluoropyridin-4-yl | 2.65[a] |
| XII-28 | 1-fluorocyclopropyl | 2-chloro-3-fluoropyridin-4-yl | 2.53[a] |
| XII-29 | 1-chlorocyclopropyl | 5,6-dichloropyrimidin-4-yl | |
| XII-30 | 1-chlorocyclopropyl | 2,6-dichloropyridin-3-yl | 3.71[a] |
| XII-31 | 1-chlorocyclopropyl | 2-fluoropyridin-3-yl | 2.47[a] |
| XII-32 | 1-chlorocyclopropyl | 3,5-dichloropyridin-4-yl | 3.68[a] |
| XII-33 | 1,3-difluoro-2-methylpropan-2-yl | 3,5-dichloropyridin-4-yl | 2.89[a] |
| XII-34 | 1-fluorocyclopropyl | 3,5-dichloropyridin-4-yl | 2.93[a] |
| XII-35 | 1-phenylcyclopropyl | 3-chloropyridin-4-yl | |
| XII-36 | 2-phenylpropan-2-yl | 3-chloropyridin-4-yl | |
| XII-37 | 2-fluoropropan-2-yl | 3-chloropyridin-4-yl | |
| XII-38 | 1-chlorocyclopropyl | 3-(trifluoromethyl)pyridin-4-yl | 3.04[a] |
| XII-39 | 1-chlorocyclopropyl | 2-chloro-8-methylquinolin-3-yl | 4.90[a] |
| XII-40 | 1-chlorocyclopropyl | 2,4-dichloropyridin-3-yl | 3.53[a] |
| XII-41 | 1-chlorocyclopropyl | 2,5-dichloropyridin-3-yl | 3.87[a] |
| XII-42 | 1-chlorocyclopropyl | 2,5-dichloropyridin-4-yl | 3.70[a] |

Measurement of Log P values for Tables 1, 2 and 3 was performed according to EEC directive 79/831 Annex V.A8 by HPLC (High Performance Liquid Chromatography) on reversed phase columns with the following methods:

[a] Measurement of LC-MS was done at pH 2.7 with 0.1% formic acid in water and with acetonitrile (contains 0.1% formic acid) as eluent with a linear gradient from 10% acetonitrile to 95% acetonitrile.

[b] Measurement with LC-MS was done at pH 7.8 with 0.001 molar ammonium hydrogen carbonate solution in water as eluent with a linear gradient from 10% acetonitrile to 95% acetonitrile.

Calibration was done with straight-chain alkan2-ones (with 3 to 16 carbon atoms) with known Log P values (measurement of Log P values using retention times with linear interpolation between successive alkanones) Lambda-max-values were determined using UV-spectra from 200 nm to 400 nm and the peak values of the chromatographic signals.

1H-NMR data and 1H-NMR-peak list 1H-NMR data of selected examples from Tables 1, 2 and 3 are either written in classical form (d-value in ppm, number of H-atoms, multiplet splitting) or as 1H-NMR-peak list.

In the 1H-NMR-peak list to each signal peak are listed the δ-value in ppm and the signal intensity in round brackets. Between the δ-value—signal intensity pairs are semicolons as delimiters.

The peak list of an example has therefore the form:
$\delta_1$ (intensity$_1$); $\delta_2$ (intensity$_2$); . . . ; $\delta_i$(intensity$_i$); . . . ; $\delta_n$(intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

1H-NMR Data for Compounds in Table 1 Written in Classical Form

| Ex-no | NMR |
|---|---|
| I-2 | 1H-NMR (400 MHz, d3-CD3CN): δ = 8.47-8.46 (dd, 1H), 8.43 (s, 1H), 7.99-7.97 (dd, 1H), 7.93 (s, 1H), 7.39-7.37 (dd, 1H), 4.64 (d, 1H), 4.51 (d, 1H), 4.26 (s, 1H), 3.61 (d, 1H), 3.11 (d, 1H), 0.60-0.45 (m, 4H) ppm |
| I-3 | 1H-NMR (400 MHz, d3-CD3CN): δ = 8.32 (s, 1H), 8.31-8.27 (dd, 1H), 7.93-7.90 (m, 2H), 7.32-7.29 (dd, 1H), 4.92 (d, 1H), 4.18 (s, 1H), 4.12 (d, 1H), 3.46 (d, 1H), 3.22 (d, 1H), 0.84-0.74 (m, 2H), 0.51-0.39 (m, 2H) ppm |

| Ex-no | NMR |
|---|---|
| I-4 | 1H-NMR (400 MHz, d3-CD3CN): δ = 8.32-8.31 (m, 2H), 7.94 (s, 1H), 7.76-7.73 (dd, 1H), 7.34-7.32 (dd, 1H), 4.76 (d, 1H), 4.28 (d, 1H), 4.08 (s, 1H), 3.24 (d, 1H), 2.94 (d, 1H), 0.60-0.35 (m, 4H) ppm |
| I-5 | 1H-NMR (400 MHz, d3-CD3CN): δ = 8.55 (s, 1H), 8.40 (d, 1H), 8.32 (s, 1H), 7.93 (s, 1H), 7.50 (d, 1H), 4.89 (d, 1H), 4.23 (s, 1H), 4.14 (d, 1H), 3.45 (d, 1H), 3.22 (d, 1H), 0.86-0.74 (m, 2H), 0.51-0.39 (m, 2H) ppm |
| I-6 | 1H-NMR (400 MHz, DMSO-d6): δ = 8.52 (s, 1H), 8.35-8.31 (m, 2H), 7.86 (s, 1H), 7.57 (d, 1H), 5.48 (s, 1H), 4.60-4.30 (m, 5H), 4.15 (d, 1H), 3.26 (d, 1H), 3.10 (d, 1H), 0.87 (t, 3H) ppm |
| I-7 | 1H-NMR (400 MHz, DMSO-d6): δ = 8.57 (s, 1H), 8.44-8.41 (m, 2H), 7.98 (s, 1H), 7.55 (d, 1H), 5.44 (s, 1H), 4.59 (d, 1H), 4.35 (d, 1H), 3.25 (d, 1H), 3.09 (d, 1H), 0.70-0.50 (m, 2H), 0.45-0.35 (m, 1H), 0.30-0.25 (m, 1H) ppm |

NMR-Peak Lists for Compounds in Table 1

Example I-1: $^1$H-NMR(300.2 MHz, CDCl3):

δ = 8.337(15.7); 8.184(6.3); 8.156(6.8); 7.931(4.7); 7.921(16.0); 7.904(5.8); 7.845(3.9); 7.842(4.1); 7.818(4.8); 7.815(5.0); 7.743(3.0); 7.738(2.9); 7.720(4.2); 7.715(5.0); 7.710(2.5); 7.692(3.2); 7.687(2.8); 7.573(3.7); 7.569(3.6); 7.550(3.4); 7.546(5.6); 7.542(3.4); 7.523(2.5); 7.519(2.3); 7.448(9.5); 7.420(8.9); 7.271(9.7); 7.265(16.4); 4.723(5.3); 4.676(9.2); 4.554(10.2); 4.507(6.0); 3.658(8.5); 3.609(9.8); 3.021(8.0); 2.972(7.0); 2.045(0.8); 1.706(1.7); 1.259(0.6); 0.880(1.8); 0.862(2.5); 0.855(2.4); 0.845(2.6); 0.837(3.0); 0.826(3.1); 0.820(2.8); 0.801(2.9); 0.720(2.0); 0.702(1.9); 0.697(2.8); 0.685(3.1); 0.678(2.4); 0.666(2.6); 0.661(3.4); 0.643(2.6); 0.505(2.3); 0.485(3.5); 0.482(2.6); 0.469(2.3); 0.462(3.2); 0.450(3.2); 0.446(2.1); 0.426(2.3); 0.406(3.2); 0.386(2.7); 0.381(3.4); 0.370(3.1); 0.361(2.4); 0.351(2.3); 0.345(2.7); 0.326(1.6); 0.072(0.4); 0.011(0.4); 0.000(12.2); −0.011(0.5)

Example I-8: $^1$H-NMR(400.0 MHz, CD3CN):

δ = 8.261(1.6); 8.256(1.8); 8.249(1.8); 8.244(1.7); 8.230(4.8); 7.926(0.6); 7.886(0.5); 7.869(5.7); 7.851(1.8); 7.846(1.7); 7.290(1.8); 7.278(1.8); 7.271(1.7); 7.259(1.6); 5.447(3.2); 4.664(3.0); 4.628(3.4); 4.094(3.3); 4.058(2.9); 3.571(5.5); 3.249(2.0); 3.214(3.1); 3.090(3.5); 3.054(2.3); 2.889(6.7); 2.772(5.9); 2.144(9.5); 1.972(0.4); 1.964(1.2); 1.958(1.9); 1.952(8.3); 1.946(14.6); 1.940(18.9); 1.934(12.9); 1.928(6.5); 1.276(1.5); 1.249(16.0); 0.392(0.5); 0.388(0.7); 0.382(0.7); 0.373(1.3); 0.368(0.8); 0.359(0.7); 0.350(0.8); 0.062(0.5); 0.048(0.9); 0.038(1.3); 0.023(1.0); 0.016(2.5); 0.009(1.4); 0.000(4.8); −0.004(2.1); −0.013(1.3); −0.018(0.9); −0.027(0.8); −0.210(1.1); −0.219(1.0); −0.228(1.0); −0.232(1.3); −0.234(1.3); −0.242(0.9); −0.247(0.9); −0.253(0.6)

Example I-9: $^1$H-NMR(400.1 MHz, CDCl3):

δ = 8.551(15.8); 8.527(14.6); 8.269(15.0); 7.945(15.0); 7.261(50.6); 5.299(1.6); 4.760(16.0); 4.694(6.7); 4.658(9.8); 4.513(8.9); 4.477(6.1); 4.149(1.1); 4.131(3.3); 4.113(3.3); 4.095(1.1); 3.445(8.1); 3.409(9.7); 3.082(7.7); 3.047(6.4); 2.170(1.5); 2.044(14.6); 2.005(0.4); 1.566(23.6); 1.277(3.9); 1.259(8.3); 1.241(3.9); 0.731(0.6); 0.726(1.1); 0.720(0.4); 0.713(1.5); 0.708(1.6); 0.696(5.6); 0.692(4.9); 0.681(4.0); 0.673(9.4); 0.661(15.9); 0.649(8.2); 0.645(13.9); 0.639(5.0); 0.626(2.7); 0.613(0.8); 0.000(0.8)

Example I-10: $^1$H-NMR(499.9 MHz, CDCl3):

δ = 8.279(5.2); 8.206(5.3); 7.901(5.5); 7.281(2.2); 5.731(3.6); 4.651(0.4); 4.622(7.2); 4.620(6.9); 4.591(0.5); 3.715(2.6); 3.685(3.0); 3.194(2.5); 3.163(2.2); 2.561(16.0); 2.051(0.6); 1.276(0.5); 1.262(1.3); 1.253(3.0); 0.880(0.5); 0.867(0.4); 0.846(0.7); 0.843(0.7); 0.830(1.9); 0.827(2.2); 0.822(2.0); 0.813(3.2); 0.805(1.8); 0.801(0.9); 0.794(0.7); 0.791(0.7); 0.783(0.4); 0.774(0.4); 0.768(0.6); 0.759(0.3); 0.741(0.7); 0.729(2.5); 0.721(4.2); 0.714(2.5); 0.713(2.5); 0.699(0.6); 0.000(0.4)

Example I-11: $^1$H-NMR(300.2 MHz, CDCl3):

δ = 8.652(3.4); 8.649(3.5); 8.541(2.8); 8.532(3.1); 8.417(2.3); 8.412(2.6); 8.404(1.9); 8.277(2.1); 7.925(2.2); 7.263(30.2); 5.537(3.9); 5.302(6.8); 4.662(0.6); 4.613(1.9); 4.570(2.4); 4.522(0.8); 3.521(2.8); 3.472(3.3); 2.951(2.6); 2.902(2.2); 1.596(16.0); 1.254(0.7); 0.826(0.5); 0.807(0.8); 0.799(0.7); 0.791(0.7); 0.779(1.1); 0.774(1.0); 0.764(0.9); 0.745(1.4); 0.719(1.0); 0.708(1.2); 0.702(0.7); 0.685(1.4); 0.666(0.9); 0.586(0.6); 0.567(1.7); 0.557(1.8); 0.545(1.6); 0.534(2.0); 0.529(2.1); 0.521(1.5); 0.510(1.3); 0.503(0.7); 0.495(1.1); 0.069(3.5); 0.011(0.5); 0.000(16.4); −0.011(0.7)

Example I-12: $^1$H-NMR(400.0 MHz, DMSO):

δ = 8.558(13.6); 8.433(8.5); 8.420(8.9); 8.397(16.0); 8.022(16.0); 7.639(6.6); 7.627(6.4); 7.565(1.3); 7.560(1.9); 7.545(3.1); 7.541(3.4); 7.526(1.8); 7.522(1.8); 7.334(0.8); 7.329(0.9); 7.320(1.1); 7.314(2.1); 7.311(1.6); 7.301(1.8); 7.295(2.4); 7.290(1.4); 7.281(1.4); 7.277(1.2); 7.178(6.6); 7.159(7.2); 7.153(3.4); 7.143(2.3); 7.140(2.2); 7.132(2.1); 7.130(1.7); 5.296(11.1); 4.251(2.6); 4.215(7.1); 4.184(7.0); 4.148(2.6); 3.342(22.6); 2.941(2.3); 2.907(6.5); 2.878(6.8); 2.848(1.5); 2.844(2.6); 2.815(5.7); 2.801(5.4); 2.765(1.1); 2.548(51.6); 2.531(0.3); 2.526(0.5); 2.518(6.8); 2.513(13.7); 2.509(18.0); 2.504(12.7); 2.500(5.9); 0.000(0.8)

Example I-13: $^1$H-NMR(400.0 MHz, DMSO):

δ = 8.432(11.5); 8.351(0.6); 8.338(16.0); 8.327(8.4); 8.323(6.2); 8.317(5.6); 8.128(0.3); 7.856(12.8); 7.737(3.5); 7.730(3.4); 7.716(3.9); 7.709(3.8); 7.364(6.1); 7.348(6.1); 7.343(6.1); 7.335(5.6); 6.139(12.0); 4.854(3.1); 4.818(5.5); 4.744(5.4); 4.708(3.1); 3.519(3.8); 3.484(4.7); 3.333(38.9); 3.241(4.5); 3.205(3.6); 2.544(61.9); 2.527(0.5); 2.513(12.0); 2.509(24.2); 2.504(31.5); 2.500(22.7); 2.495(10.8); 0.000(1.7)

Example I-14: $^1$H-NMR(400.0 MHz, DMSO):

δ = 9.752(0.8); 8.813(1.2); 8.764(0.5); 8.756(0.5); 8.601(0.6); 8.581(0.6); 8.515(1.9); 8.508(0.6); 8.480(13.9); 8.465(0.4); 8.420(0.4); 8.361(0.4); 8.345(1.1); 8.326(16.0); 8.315(9.4); 8.302(8.3); 8.258(5.1); 8.253(5.2); 8.246(5.3); 8.241(4.5); 8.179(0.6); 8.160(0.4); 8.156(0.4); 8.031(1.3); 7.999(1.3); 7.870(0.4); 7.859(0.5); 7.850(0.5); 7.839(0.5); 7.764(0.4); 7.740(0.5); 7.715(14.5); 7.696(4.6); 7.691(4.4); 7.676(5.2); 7.672(4.3); 7.598(0.5); 7.585(0.4); 7.579(0.5); 7.568(0.4); 7.438(0.4); 7.427(0.4); 7.407(0.3); 7.276(7.3); 7.264(7.0); 7.235(5.0); 7.224(5.1); 7.216(4.9); 7.204(4.8); 6.257(14.6); 5.313(5.7); 5.277(6.2); 5.164(1.1); 4.674(6.0); 4.638(5.4); 4.576(0.4); 4.548(0.6); 4.312(0.7); 4.286(0.5); 3.798(5.2); 3.762(6.3); 3.652(0.4); 3.616(0.4); 3.505(6.3); 3.469(5.0); 3.426(0.5); 3.409(0.7); 3.392(0.8); 3.363(2.3); 3.325(764.5); 3.283(0.4); 3.271(0.3); 3.264(0.5); 2.995(1.6); 2.711(0.6); 2.675(2.8); 2.671(3.4); 2.579(0.5); 2.541(119.6); 2.506(467.9); 2.502(564.3); 2.497(386.2); 2.368(0.6); 2.333(2.8); 2.329(3.6); 1.297(0.3); 1.259(0.4); 1.235(0.9); 1.210(1.0); 1.194(1.1); 0.000(13.6); −0.009(0.5)

Example I-15: $^1$H-NMR(400.0 MHz, DMSO):

δ = 8.555(13.4); 8.435(8.1); 8.422(8.5); 8.391(15.7); 8.036(16.0); 7.601(6.5); 7.589(6.3); 7.429(6.7); 7.324(4.6); 7.311(13.7); 7.301(5.4); 7.296(4.6); 7.291(1.9); 7.289(2.2); 7.284(2.3); 7.276(0.7); 7.272(0.8); 5.297(10.4); 4.199(0.7); 4.163(11.4); 4.161(11.1); 4.124(0.7); 3.332(44.9); 2.932(0.5); 2.885(1.7); 2.850(7.9); 2.837(8.2); 2.832(4.5); 2.810(0.7); 2.797(6.7); 2.752(6.4); 2.718(3.1); 2.544(64.2); 2.527(0.7); 2.514(14.5); 2.510(29.4); 2.505(38.7); 2.500(27.5); 2.496(12.9); 0.000(2.0)

Example I-16: $^1$H-NMR(400.0 MHz, CD3CN):

δ = 8.297(0.9); 8.292(0.9); 8.285(0.9); 8.280(0.9); 8.261(1.7); 8.256(1.8); 8.249(1.8); 8.244(1.7); 8.136(5.6); 7.952(1.0); 7.947(1.1); 7.938(3.2); 7.933(1.7); 7.928(2.1); 7.901(5.4); 7.846(2.0); 7.841(3.9); 7.827(1.9); 7.823(1.8); 7.336(0.9); 7.325(0.9); 7.317(0.9); 7.306(0.9); 7.286(2.0); 7.274(5.5); 7.272(6.4); 7.267(3.3); 7.255(4.0); 7.252(4.6); 7.249(6.1); 7.240(0.6); 6.842(0.4); 6.834(3.3); 6.827(6.5); 6.822(1.9); 6.817(1.2); 6.811(4.1); 6.805(5.3); 6.796(0.5); 4.712(1.5); 4.676(1.6); 4.519(2.1); 4.482(3.2); 4.349(3.8); 4.313(2.5); 4.216(0.7); 4.200(2.4); 4.185(2.4); 4.169(0.8); 4.086(1.1); 4.068(3.3); 4.050(5.6); 4.032(1.4); 4.028(1.3); 4.013(1.2); 3.997(0.4); 3.980(1.6); 3.945(1.5); 3.899(5.5); 3.351(0.9); 3.314(1.4); 3.292(2.5); 3.256(3.3); 3.175(1.6); 3.139(1.1); 3.024(3.4); 2.988(2.6); 2.888(16.0); 2.771(13.7); 2.140(9.2); 1.972(14.2); 1.964(2.5); 1.958(4.0); 1.952(16.6); 1.946(28.7); 1.940(37.0); 1.934(25.1); 1.927(12.8); 1.348(11.0); 1.332(11.0); 1.323(5.9); 1.307(5.7); 1.221(3.8); 1.204(7.6); 1.186(3.8); 0.008(0.5); 0.000(11.1); −0.009(0.4)

Example I-17: $^1$H-NMR(300.2 MHz, CDCl3):

δ = 8.723(0.9); 8.271(16.0); 8.173(0.9); 7.937(15.6); 7.916(0.5); 7.627(1.2); 7.293(17.1); 7.290(17.7); 7.265(26.7); 7.247(0.6); 7.237(1.0); 7.229(0.6); 7.217(0.4); 7.178(0.7); 7.169(0.5); 7.149(0.4); 6.778(0.8); 5.380(11.7); 5.367(1.6); 5.301(2.2); 4.947(0.3); 4.611(1.2); 4.562(11.1); 4.552(14.9); 4.524(0.4); 4.504(1.7); 4.399(0.7); 4.373(0.7); 3.375(6.8); 3.327(8.8); 2.922(6.8); 2.874(6.0); 2.637(0.4); 1.681(1.6); 1.633(1.8); 1.395(0.7); 1.386(0.9); 1.381(0.7); 1.372(0.8); 1.367(0.9); 1.358(0.7); 1.342(1.3); 1.300(0.6); 1.254(6.7); 1.234(0.9); 1.224(0.6); 1.135(1.1); 1.065(1.9); 0.880(0.8); 0.855(0.5); 0.826(1.3); 0.809(2.4); 0.791(2.1); 0.786(2.5); 0.782(1.8); 0.775(3.6); 0.770(2.2); 0.766(3.4); 0.744(4.8); 0.722(3.2); 0.712(2.6); 0.707(3.8); 0.689(10.0); 0.674(2.2); 0.669(3.7); 0.655(3.1); 0.636(3.9); 0.614(3.1); 0.611(2.4); 0.606(3.5); 0.597(2.4); 0.591(2.3); 0.572(2.4); 0.555(1.1); 0.011(0.6); 0.000(17.1); −0.011(0.7)

Example I-18: $^1$H-NMR(400.0 MHz, DMSO):

δ = 8.493(8.3); 8.490(8.1); 8.438(16.0); 8.348(5.3); 8.346(5.2); 8.336(5.4); 8.334(5.3); 7.998(15.4); 7.530(3.5); 7.517(4.3); 7.514(4.3); 7.501(3.4); 5.450(14.6); 4.693(5.8); 4.657(7.2); 4.402(7.1); 4.365(5.8); 3.353(54.7); 3.242(4.5); 3.207(5.8); 3.020(5.6); 2.986(4.2); 2.547(24.2); 2.516(5.4); 2.512(10.9); 2.507(14.2); 2.503(10.2); 2.498(4.8); 0.634(0.8); 0.620(1.6); 0.614(1.3); 0.607(2.0); 0.602(2.2); 0.593(2.8); 0.587(3.4); 0.575(3.2); 0.566(3.0); 0.564(3.0); 0.552(1.9); 0.544(3.2); 0.532(2.7); 0.512(1.8); 0.499(3.9); 0.493(4.4); 0.480(4.7); 0.472(3.5); 0.465(3.0); 0.458(2.2); 0.452(1.3); 0.446(1.9); 0.432(0.4); 0.000(2.1)

Example I-19: $^1$H-NMR(400.0 MHz, DMSO):

δ = 8.480(8.2); 8.476(8.0); 8.420(16.0); 8.348(0.4); 8.337(5.1); 8.335(5.0); 8.324(5.2); 8.322(5.0); 7.987(15.6); 7.495(3.4); 7.482(3.9); 7.479(3.9); 7.467(3.2); 5.479(7.8); 5.474(7.5); 4.581(3.5); 4.545(5.2); 4.408(4.8); 4.372(3.3); 3.331(85.2); 3.177(3.2); 3.143(4.2); 2.933(4.0); 2.899(3.1); 2.542(25.5); 2.525(0.8); 2.512(18.7); 2.508(38.0); 2.503(49.7); 2.498(34.9); 2.494(16.2); 0.586(0.3); 0.564(1.0); 0.556(1.7); 0.548(3.9); 0.534(1.5); 0.513(1.5); 0.499(4.1); 0.484(1.2); 0.462(0.5); 0.451(0.5); 0.337(0.6); 0.332(0.4); 0.326(0.6); 0.323(0.6); 0.312(0.8); 0.294(2.7); 0.278(1.3); 0.273(1.8); 0.268(3.0); 0.265(2.8); 0.259(1.6); 0.253(1.1); 0.238(2.5); 0.233(1.8); 0.228(1.3); 0.219(0.7); 0.210(0.6); 0.205(0.5); 0.194(0.5); 0.008(0.7); 0.000(21.2); −0.009(0.7)

Example I-20: $^1$H-NMR(400.0 MHz, DMSO):

δ = 8.470(8.0); 8.466(8.0); 8.392(15.7); 8.346(5.1); 8.334(5.2); 8.023(15.8); 7.586(3.2); 7.573(3.9); 7.570(3.9); 7.557(4.4); 7.537(3.4); 7.534(3.6); 7.519(1.9); 7.515(1.9); 7.331(0.8); 7.326(0.9); 7.317(1.1); 7.311(2.3); 7.298(1.9); 7.293(2.6); 7.287(1.4); 7.278(1.4); 7.274(1.2); 7.175(6.1); 7.157(6.1); 7.149(3.7); 7.141(2.5); 7.138(2.2); 7.128(2.2); 5.285(13.6); 4.218(0.3); 4.182(16.0); 3.352(34.8); 2.827(1.7); 2.784(12.8); 2.774(7.4); 2.739(1.7); 2.720(0.4); 2.550(72.9); 2.533(0.4); 2.519(5.2); 2.515(10.6); 2.510(13.9); 2.506(10.0); 2.502(4.8); 2.376(0.4); 0.000(4.1)

Example I-21: $^1$H-NMR(400.0 MHz, CD3CN):

δ = 8.300(0.4); 8.273(0.3); 8.245(4.9); 8.240(4.7); 8.180(3.3); 8.178(3.2); 8.168(3.4); 8.166(3.3); 8.136(6.2); 8.010(0.4); 7.651(7.2); 7.255(2.0); 7.241(2.6); 7.226(1.9); 5.352(0.4); 4.675(6.3); 4.653(2.4); 4.650(4.0); 4.646(2.6); 4.627(2.2); 4.623(2.1); 4.603(0.8); 4.598(1.0); 4.559(1.6); 4.556(1.5); 4.533(4.1); 4.531(4.6); 4.528(2.8); 4.509(3.4); 4.505(2.3); 4.484(0.9); 4.480(1.0); 4.419(2.2); 4.415(1.9); 4.394(1.7); 4.386(6.6); 4.373(6.8); 4.336(1.1); 4.086(1.0); 4.068(2.9); 4.050(3.0); 4.033(1.0); 3.119(0.9); 3.083(4.3); 3.065(5.8); 3.030(1.2); 2.891(2.3); 2.775(1.9); 2.206(8.0); 1.973(12.8); 1.967(0.8); 1.960(1.4); 1.954(6.3); 1.948(11.3); 1.942(14.9); 1.936(10.2); 1.930(5.2); 1.285(0.5); 1.222(3.5); 1.204(6.8); 1.186(3.4); 1.093(0.6); 1.089(1.1); 1.085(0.6); 1.012(9.0); 1.006(16.0); 0.999(8.6); 0.008(1.0); 0.000(20.8); −0.009(0.8)

-continued

Example I-22: $^1$H-NMR(400.0 MHz, DMSO):

δ = 8.468(7.8); 8.464(7.7); 8.380(15.8); 8.346(4.8); 8.345(4.7); 8.334(4.9); 8.332(4.8); 8.031(16.0); 7.539(3.0); 7.526(3.6); 7.523(3.7); 7.510(2.9); 7.430(6.8); 7.321(3.3); 7.316(3.0); 7.307(15.5); 7.301(6.5); 7.296(4.7); 7.289(1.9); 7.286(2.1); 7.281(1.0); 7.275(0.6); 7.271(0.7); 5.276(14.7); 5.323(4.7); 5.287(5.1); 4.728(4.8); 4.120(7.2); 4.084(2.4); 3.330(93.6); 2.997(0.7); 2.794(2.0); 2.760(7.0); 2.733(14.2); 2.713(0.9); 2.704(2.1); 2.677(0.4); 2.673(0.5); 2.668(0.3); 2.543(117.5); 2.526(1.1); 2.512(23.7); 2.508(47.0); 2.503(61.0); 2.499(43.0); 2.494(19.8); 2.369(0.4); 2.330(0.4); 0.008(0.7); 0.000(18.7); −0.009(0.6)

Example I-23: $^1$H-NMR(400.0 MHz, DMSO):

δ = 8.332(7.0); 8.326(16.0); 8.232(4.1); 8.227(4.3); 8.220(4.5); 8.216(4.4); 8.208(4.2); 8.206(4.0); 8.196(4.2); 8.194(4.1); 7.711(12.6); 7.589(3.7); 7.584(3.8); 7.569(4.3); 7.565(4.0); 7.189(2.7); 7.176(3.4); 7.173(3.5); 7.168(4.8); 7.160(3.0); 7.156(4.7); 7.148(4.1); 7.137(4.0); 6.256(10.7); 5.323(4.7); 5.287(5.1); 4.728(4.8); 4.692(4.3); 3.862(3.8); 3.827(4.1); 3.328(86.5); 3.260(4.0); 3.225(3.5); 2.996(4.4); 2.712(0.4); 2.671(0.4); 2.542(107.0); 2.525(1.0); 2.511(21.3); 2.507(43.5); 2.502(57.2); 2.498(40.5); 2.493(19.0); 2.368(0.4); 2.329(0.4); 0.008(0.7); 0.000(20.3); −0.009(0.6)

Example I-24: $^1$H-NMR(400.0 MHz, DMSO):

δ = 8.333(8.1); 8.329(8.3); 8.320(16.0); 8.307(6.4); 8.301(6.3); 8.242(4.9); 8.240(4.8); 8.230(5.0); 8.228(4.9); 7.829(15.7); 7.758(3.7); 7.752(3.6); 7.737(4.1); 7.731(4.0); 7.370(7.0); 7.349(6.3); 7.249(3.1); 7.236(3.8); 7.233(3.8); 7.221(3.0); 6.117(14.5); 4.851(4.1); 4.815(6.0); 4.704(6.0); 4.668(4.0); 3.447(4.0); 3.413(4.8); 3.343(32.2); 3.155(4.4); 3.120(3.6); 3.001(0.5); 2.715(0.6); 2.545(121.5); 2.529(0.6); 2.515(6.8); 2.510(14.0); 2.506(18.6); 2.501(13.4); 2.497(6.4); 2.371(0.6); 0.000(7.5)

Example I-25: $^1$H-NMR(400.0 MHz, CD3CN):

δ = 8.286(1.2); 8.281(1.2); 8.274(1.3); 8.269(1.3); 8.254(3.3); 7.920(4.2); 7.882(1.3); 7.877(1.2); 7.863(1.3); 7.858(1.2); 7.308(1.3); 7.296(1.3); 7.289(1.3); 7.277(1.2); 4.737(1.2); 4.732(1.2); 4.701(1.4); 4.696(1.4); 4.285(1.5); 4.282(1.4); 4.249(1.3); 4.246(1.2); 4.063(2.2); 3.231(4.6); 2.889(16.0); 2.772(14.1); 2.169(8.4); 1.965(0.6); 1.959(1.1); 1.953(5.2); 1.947(9.2); 1.941(12.0); 1.934(8.1); 1.928(4.1); 0.764(0.3); 0.749(0.4); 0.745(0.6); 0.736(0.4); 0.730(0.4); 0.715(0.6); 0.708(0.3); 0.699(0.4); 0.693(0.4); 0.689(0.5); 0.679(0.4); 0.665(0.5); 0.549(0.4); 0.545(0.4); 0.529(0.5); 0.515(0.6); 0.501(0.7); 0.495(0.5); 0.482(0.7); 0.480(0.6); 0.468(0.5); 0.466(0.5); 0.456(1.2); 0.452(0.8); 0.441(0.7); 0.436(0.4); 0.429(0.6); 0.421(0.5); 0.415(0.5); 0.259(0.4); 0.243(0.4); 0.238(0.4); 0.232(0.7); 0.224(0.4); 0.218(0.5); 0.211(0.4); 0.208(0.5); 0.206(0.4); 0.198(0.6); 0.190(0.3); 0.186(0.3); 0.008(0.4); 0.000(10.4); −0.009(0.4)

Example I-26: $^1$H-NMR(400.1 MHz, CDCl3):

δ = 8.331(0.3); 8.257(16.0); 8.131(1.1); 8.057(0.3); 8.025(14.0); 7.987(1.1); 7.330(37.8); 7.295(0.7); 7.272(8.6); 5.611(3.2); 4.811(6.9); 4.776(7.7); 4.514(12.5); 4.155(8.1); 4.129(0.4); 4.120(7.4); 4.112(0.4); 3.200(5.3); 3.166(7.1); 2.978(7.0); 2.944(5.2); 2.043(0.9); 1.807(0.4); 1.794(0.7); 1.785(1.2); 1.773(0.5); 1.725(1.4); 1.538(0.5); 1.526(1.2); 1.517(1.2); 1.503(0.4); 1.276(0.6); 1.263(1.0); 1.259(1.4); 1.241(0.4); 0.898(0.5); 0.881(1.5); 0.864(0.6); 0.677(5.5); 0.670(1.2); 0.655(10.8); 0.653(10.8); 0.637(1.5); 0.631(8.7); 0.460(2.7); 0.452(0.4); 0.445(3.2); 0.439(3.1); 0.436(2.4); 0.422(4.6); 0.414(2.0); 0.405(0.4); 0.399(2.1); 0.256(2.7); 0.249(0.4); 0.241(2.7); 0.235(3.2); 0.231(2.6); 0.218(4.5); 0.210(2.5); 0.201(0.4); 0.195(2.0); 0.000(5.9)

Example I-27: $^1$H-NMR(300.2 MHz, CDCl3):

δ = 8.882(7.3); 8.867(7.5); 8.249(16.0); 8.224(4.1); 8.221(4.0); 8.154(3.5); 8.151(3.6); 8.125(4.1); 8.123(4.1); 7.961(10.6); 7.760(2.1); 7.755(2.2); 7.737(3.2); 7.732(4.3); 7.727(2.1); 7.709(2.8); 7.704(2.6); 7.637(2.9); 7.632(2.9); 7.614(2.4); 7.609(4.3); 7.604(2.8); 7.586(2.0); 7.581(1.8); 7.532(6.5); 7.517(6.4); 7.265(16.7); 4.917(5.3); 4.870(5.8); 4.299(8.3); 4.109(0.3); 3.963(6.2); 3.919(5.3); 3.860(3.3); 3.857(3.3); 3.813(4.3); 3.810(4.3); 3.523(5.8); 3.476(4.5); 2.045(1.5); 2.006(5.3); 1.738(1.5); 1.283(0.4); 1.259(0.9); 1.235(0.4); 0.853(1.0); 0.833(2.3); 0.827(1.6); 0.817(1.4); 0.807(2.8); 0.797(4.9); 0.791(2.0); 0.772(4.0); 0.763(3.1); 0.754(1.4); 0.743(2.1); 0.739(3.2); 0.720(1.5); 0.491(2.0); 0.471(2.6); 0.465(2.1); 0.457(2.0); 0.445(2.4); 0.436(2.4); 0.431(1.7); 0.410(1.7); 0.301(2.1); 0.280(2.4); 0.277(2.7); 0.264(2.2); 0.257(2.1); 0.244(2.1); 0.241(2.3); 0.220(1.5); 0.011(0.3); 0.000(10.8); −0.011(0.5)

Example I-28: $^1$H-NMR(300.2 MHz, CDCl3):

δ = 8.709(3.2); 8.705(3.3); 8.557(1.8); 8.549(2.7); 8.544(2.2); 8.491(3.3); 8.483(2.6); 8.388(3.5); 7.954(3.7); 7.262(38.2); 5.301(3.0); 4.767(0.9); 4.718(3.4); 4.688(3.4); 4.640(0.9); 3.331(10.0); 2.439(0.4); 1.569(16.0); 1.254(0.5); 0.792(0.5); 0.771(1.3); 0.760(1.8); 0.744(2.7); 0.729(3.7); 0.721(3.3); 0.713(2.1); 0.707(1.9); 0.693(1.0); 0.674(0.5); 0.662(0.3); 0.100(2.9); 0.089(76.3); 0.078(3.8); 0.011(1.0); 0.000(27.6); −0.011(1.2)

Example I-29: $^1$H-NMR(400.1 MHz, DMSO):

δ = 8.410(14.0); 7.970(13.4); 7.842(4.0); 7.822(7.6); 7.803(4.9); 7.452(5.8); 7.434(5.2); 7.433(5.4); 7.428(5.9); 7.408(5.2); 5.759(4.9); 5.472(16.0); 4.673(4.8); 4.637(6.1); 4.401(6.1); 4.365(4.9); 3.319(47.5); 3.309(5.4); 3.275(6.3); 3.060(5.8); 3.026(4.5); 2.530(0.6); 2.525(1.0); 2.517(14.2); 2.512(29.2); 2.508(39.4); 2.503(27.7); 2.499(12.8); 0.635(1.0); 0.627(1.1); 0.622(0.7); 0.614(1.5); 0.611(1.2); 0.607(1.2); 0.600(2.8); 0.595(2.1); 0.586(0.9); 0.561(1.3); 0.540(2.0); 0.535(0.9); 0.520(11.5); 0.511(7.4); 0.490(2.9); 0.481(1.0); 0.472(0.9)

Example I-30: $^1$H-NMR(300.2 MHz, CDCl3):

δ = 8.339(3.5); 8.331(16.0); 8.328(12.6); 8.319(3.0); 8.269(12.1); 7.884(11.9); 7.268(11.2); 5.647(13.3); 5.302(0.4); 4.694(0.7); 4.645(12.8); 4.640(13.4); 4.592(0.8); 3.773(6.3); 3.722(7.5); 3.283(7.0); 3.232(5.5); 1.680(3.2); 1.254(0.4); 0.894(0.5); 0.889(0.7); 0.884(0.7); 0.864(4.3); 0.850(3.9); 0.843(4.5); 0.839(5.0); 0.836(4.6); 0.830(4.4); 0.823(1.6); 0.818(1.5); 0.810(0.9); 0.804(0.9); 0.797(1.1); 0.769(2.4); 0.753(3.0); 0.746(5.3); 0.738(8.1); 0.726(4.1); 0.722(4.3); 0.713(1.5); 0.700(0.4); 0.000(7.3); −0.011(0.4)

| Example I-31: ¹H-NMR(300.2 MHz, CDCl3): |
|---|
| δ = 8.282(9.4); 7.939(8.9); 7.772(5.9); 7.745(6.5); 7.274(9.0); 7.246(5.1); 5.254(8.7); 4.558(16.0); 3.412(4.8); 3.364(5.7); 2.908(4.8); 2.860(4.0); 1.819(0.8); 0.802(0.6); 0.784(1.5); 0.766(1.7); 0.759(1.5); 0.749(2.0); 0.741(1.9); 0.735(1.3); 0.725(1.2); 0.717(1.6); 0.703(1.9); 0.690(1.9); 0.677(0.5); 0.669(3.5); 0.664(5.1); 0.659(3.4); 0.638(2.0); 0.624(1.8); 0.601(2.3); 0.583(1.2); 0.577(1.9); 0.569(2.0); 0.559(1.6); 0.552(1.8); 0.534(1.6); 0.517(0.7); 0.000(2.8) |

| Example I-32: ¹H-NMR(499.9 MHz, CDCl3): |
|---|
| δ = 8.262(9.8); 7.905(9.3); 7.730(5.8); 7.722(0.5); 7.714(6.1); 7.271(4.0); 7.143(6.3); 7.121(6.0); 7.054(5.6); 7.037(5.4); 5.595(7.5); 4.600(2.4); 4.572(4.6); 4.510(6.0); 4.482(3.3); 4.070(16.0); 3.359(4.5); 3.330(5.0); 2.846(4.3); 2.817(3.9); 1.760(1.8); 0.815(1.0); 0.804(1.4); 0.800(1.4); 0.793(1.6); 0.789(1.7); 0.782(1.8); 0.779(1.7); 0.768(1.7); 0.705(1.1); 0.691(1.7); 0.683(1.7); 0.679(1.7); 0.672(1.5); 0.669(2.1); 0.658(1.6); 0.620(1.6); 0.608(2.0); 0.606(1.6); 0.598(1.6); 0.594(1.7); 0.586(1.7); 0.572(1.7); 0.500(1.6); 0.489(1.7); 0.486(1.9); 0.479(1.7); 0.474(1.6); 0.468(1.4); 0.464(1.5); 0.453(1.0); 0.000(3.2) |

| Example I-33: ¹H-NMR(400.0 MHz, DMSO): |
|---|
| δ = 8.407(15.4); 8.314(7.1); 8.302(7.3); 7.994(16.0); 7.443(9.0); 7.379(4.8); 7.376(4.6); 7.366(4.7); 7.363(4.4); 5.497(8.1); 5.493(8.3); 4.519(3.9); 4.483(5.6); 4.335(5.1); 4.299(3.6); 3.334(81.5); 3.065(2.7); 3.062(2.6); 3.032(4.1); 3.029(4.1); 2.997(0.4); 2.918(4.3); 2.886(2.8); 2.713(0.3); 2.543(82.0); 2.526(0.6); 2.521(1.0); 2.512(14.4); 2.508(29.6); 2.504(39.3); 2.499(28.0); 2.494(13.2); 0.605(0.5); 0.600(0.6); 0.586(1.1); 0.575(1.4); 0.571(1.5); 0.566(1.5); 0.555(1.8); 0.548(2.3); 0.533(1.7); 0.525(1.6); 0.520(2.1); 0.516(1.9); 0.504(1.6); 0.495(1.7); 0.482(1.3); 0.473(0.5); 0.468(0.5); 0.465(0.5); 0.360(0.5); 0.354(0.5); 0.339(1.4); 0.323(3.1); 0.313(3.7); 0.298(3.7); 0.287(2.8); 0.272(1.1); 0.260(0.4); 0.255(0.4); 0.251(0.4) |

| Example I-34: ¹H-NMR(400.0 MHz, DMSO): |
|---|
| δ = 8.413(0.8); 8.336(16.0); 8.235(5.2); 8.230(5.4); 8.224(5.5); 8.219(5.1); 8.155(7.4); 8.142(7.5); 7.965(0.7); 7.741(15.7); 7.632(4.8); 7.628(4.6); 7.613(5.4); 7.608(4.8); 7.198(5.6); 7.186(12.8); 7.179(6.4); 7.167(4.7); 7.055(5.4); 7.052(4.7); 7.042(5.1); 7.039(4.3); 6.327(15.9); 5.429(1.7); 5.189(5.7); 5.153(6.4); 4.707(6.2); 4.671(5.4); 3.837(5.3); 3.802(5.7); 3.336(124.8); 3.208(5.3); 3.174(4.8); 3.003(1.3); 2.719(0.6); 2.683(0.5); 2.679(0.6); 2.674(0.4); 2.549(138.9); 2.519(41.1); 2.514(73.2); 2.510(89.1); 2.505(61.0); 2.501(27.7); 2.376(0.5); 2.341(0.4); 2.337(0.5); 2.332(0.4); 1.631(0.6); 1.612(0.6); 1.149(5.8); 0.812(0.7); 0.793(1.5); 0.774(0.6) |

| Example I-35: ¹H-NMR(400.0 MHz, DMSO): |
|---|
| δ = 8.389(15.2); 8.294(6.9); 8.282(7.1); 8.032(16.0); 7.510(1.6); 7.505(1.9); 7.489(3.6); 7.486(3.7); 7.465(10.3); 7.389(5.0); 7.386(4.6); 7.376(4.8); 7.373(4.4); 7.331(0.9); 7.327(0.9); 7.317(1.1); 7.312(2.4); 7.298(2.0); 7.293(2.6); 7.288(1.5); 7.279(1.4); 7.274(1.3); 7.177(4.6); 7.173(3.4); 7.161(5.0); 7.158(5.3); 7.152(2.8); 7.147(3.8); 7.143(3.7); 7.140(2.4); 7.127(2.2); 5.276(15.4); 4.184(2.6); 4.148(7.7); 4.121(7.7); 4.085(2.6); 3.340(126.7); 3.004(1.4); 2.787(0.8); 2.768(1.6); 2.753(10.9); 2.734(6.9); 2.721(6.9); 2.686(1.2); 2.679(0.6); 2.674(0.4); 2.549(115.5); 2.532(1.0); 2.519(22.0); 2.514(44.3); 2.510(57.5); 2.505(41.0); 2.501(19.4); 2.376(0.4); 2.337(0.4) |

| Example I-36: ¹H-NMR(400.0 MHz, DMSO): |
|---|
| δ = 8.357(14.2); 8.216(6.4); 8.203(6.6); 7.918(16.0); 7.393(7.6); 7.341(4.5); 7.338(4.0); 7.328(4.3); 7.325(3.9); 5.428(14.8); 4.580(1.3); 4.557(2.9); 4.537(2.1); 4.496(1.8); 4.492(1.8); 4.472(1.2); 4.468(1.3); 4.462(1.4); 4.438(2.9); 4.418(2.1); 4.400(1.7); 4.396(1.7); 4.375(2.9); 4.354(2.9); 4.318(1.1); 4.312(0.6); 4.274(11.8); 4.257(1.5); 4.253(1.5); 4.234(0.5); 3.340(58.9); 3.326(0.3); 3.043(0.3); 3.007(12.9); 2.971(0.3); 2.549(82.4); 2.535(0.4); 2.533(0.5); 2.528(0.7); 2.519(10.7); 2.515(22.4); 2.510(29.6); 2.505(20.8); 2.501(9.6); 1.629(0.4); 0.904(9.1); 0.898(15.8); 0.892(8.8) |

| Example I-37: ¹H-NMR(400.0 MHz, DMSO): |
|---|
| δ = 8.486(0.7); 8.376(13.5); 8.302(6.4); 8.289(6.4); 8.046(14.8); 7.438(8.0); 7.413(4.1); 7.409(6.5); 7.362(4.8); 7.358(4.4); 7.349(4.6); 7.346(5.2); 7.326(3.2); 7.310(9.2); 7.305(7.8); 7.300(5.6); 7.290(5.3); 7.286(4.0); 7.277(1.5); 7.271(2.0); 7.267(1.4); 5.288(10.3); 4.095(16.0); 3.343(18.0); 3.005(2.9); 2.754(2.4); 2.748(1.2); 2.720(8.5); 2.714(9.0); 2.707(8.2); 2.693(6.7); 2.679(0.6); 2.674(1.2); 2.659(2.3); 2.550(133.0); 2.535(0.6); 2.533(0.6); 2.528(0.6); 2.519(9.0); 2.515(19.0); 2.510(25.4); 2.505(18.1); 2.501(8.6); 2.375(0.6); 2.083(0.6) |

| Example I-38: ¹H-NMR(400.0 MHz, DMSO): |
|---|
| δ = 8.323(6.8); 8.317(6.7); 8.285(15.5); 8.200(6.9); 8.188(7.1); 7.835(16.0); 7.770(4.0); 7.764(3.9); 7.749(4.5); 7.743(4.5); 7.405(7.4); 7.384(6.6); 7.230(8.9); 7.084(4.8); 7.081(4.7); 7.071(4.7); 7.068(4.5); 6.157(14.6); 4.741(4.5); 4.706(6.1); 4.560(6.0); 4.524(4.3); 3.350(14.5); 3.337(3.6); 3.303(6.1); 3.239(5.9); 3.205(3.2); 3.005(0.6); 2.719(0.6); 2.550(116.7); 2.528(0.5); 2.519(5.9); 2.514(12.3); 2.510(16.3); 2.505(11.9); 2.501(5.7); 2.375(0.6); 2.082(0.5) |

| Example I-39: ¹H-NMR(400.0 MHz, DMSO): |
|---|
| δ = 8.430(15.7); 8.328(6.9); 8.315(7.1); 8.009(15.3); 7.459(9.0); 7.411(4.9); 7.408(4.6); 7.399(4.7); 7.396(4.5); 5.530(10.1); 4.640(5.3); 4.604(6.9); 4.394(6.9); 4.358(5.3); 3.340(167.6); 3.203(5.1); 3.169(6.2); 2.911(5.9); 2.877(4.8); 2.719(0.4); 2.679(0.4); 2.550(107.1); 2.533(1.3); 2.519(26.5); 2.515(54.8); 2.510(72.9); 2.506(53.1); 2.501(26.1); 2.376(0.4); 2.341(0.4); 2.337(0.5); 2.332(0.4); 0.533(0.8); 0.527(0.8); 0.517(3.6); 0.500(16.0); 0.488(6.0); 0.477(5.2); 0.463(1.7); 0.460(1.5); 0.449(0.5); 0.440(0.8) |

| Example I-40: ¹H-NMR(400.0 MHz, DMSO): |
|---|
| δ = 8.429(16.0); 8.414(0.5); 8.398(9.9); 8.396(9.9); 7.994(15.3); 7.583(6.9); 7.570(6.8); 5.522(14.2); 4.676(5.5); 4.640(7.0); 4.402(6.9); 4.366(5.5); 3.412(0.4); 3.378(1.5); 3.341(496.9); 3.311(2.0); 3.280(0.6); 3.262(0.5); 3.244(4.5); 3.210(5.9); 3.028(5.5); 2.993(4.2); 2.713(0.3); 2.677(0.6); 2.672(0.8); 2.542(84.4); 2.507(91.6); 2.503(116.3); 2.499(84.9); 2.369(0.4); 2.334(0.6); 2.330(0.7); 0.679(0.8); 0.666(1.6); 0.660(1.5); 0.653(2.1); 0.648(2.2); 0.638(2.6); 0.634(2.5); 0.622(3.6); 0.602(2.8); 0.599(2.8); 0.588(2.1); |

0.579(3.1); 0.567(2.8); 0.548(1.8); 0.535(4.0); 0.529(4.5); 0.517(4.9); 0.508(3.6); 0.502(3.1); 0.494(2.3); 0.489(1.5); 0.482(1.9); 0.468(0.4); 0.000(2.8)
Example I-41: ¹H-NMR(400.0 MHz, DMSO):

δ = 8.422(16.0); 8.384(10.5); 8.382(10.6); 7.992(15.6); 7.572(7.1); 7.560(7.0); 5.553(8.8); 5.549(8.6); 4.575(4.1); 4.539(6.3); 4.417(5.8); 4.380(3.8); 3.330(142.1); 3.190(4.0); 3.156(5.0); 2.996(0.4); 2.930(4.7); 2.896(3.7); 2.676(0.4); 2.672(0.5); 2.667(0.4); 2.542(72.7); 2.507(64.3); 2.503(80.6); 2.498(59.6); 2.368(0.3); 2.334(0.4); 2.329(0.5); 2.325(0.4); 0.617(0.4); 0.585(5.8); 0.556(0.8); 0.534(5.9); 0.506(0.6); 0.495(0.5); 0.375(0.7); 0.366(0.8); 0.338(4.2); 0.313(4.1); 0.309(4.1); 0.304(3.6); 0.277(3.7); 0.253(0.7); 0.241(0.5); 0.000(10.9)
Example I-42: ¹H-NMR(400.0 MHz, DMSO):

δ = 8.628(1.9); 8.470(0.4); 8.384(0.4); 8.371(0.5); 8.336(6.7); 8.331(7.0); 8.318(16.0); 8.234(9.8); 8.139(0.8); 8.135(0.8); 8.109(1.9); 8.070(0.3); 7.839(14.4); 7.774(3.6); 7.767(3.6); 7.753(4.0); 7.746(3.9); 7.714(0.3); 7.679(0.4); 7.491(1.6); 7.483(0.9); 7.396(7.2); 7.375(6.7); 7.359(6.3); 7.346(6.2); 7.016(0.7); 7.004(0.8); 6.166(14.2); 5.601(0.5); 5.589(0.8); 5.577(0.4); 4.828(3.9); 4.792(6.4); 4.702(6.3); 4.666(3.8); 4.611(0.4); 4.103(0.7); 4.096(0.7); 3.899(0.5); 3.866(0.7); 3.727(0.6); 3.693(0.4); 3.439(4.3); 3.405(5.3); 3.337(290.2); 3.294(0.7); 3.278(0.8); 3.155(4.8); 3.121(3.8); 2.996(1.3); 2.731(0.5); 2.712(0.8); 2.676(0.5); 2.672(0.6); 2.543(167.4); 2.507(72.9); 2.503(93.3); 2.499(69.8); 2.369(0.8); 2.330(0.6); 1.109(1.6); 0.000(9.9)
Example I-43: ¹H-NMR(400.0 MHz, DMSO):

δ = 17.301(0.6); 15.999(0.6); 15.266(0.5); 15.247(0.5); 9.719(1.6); 8.983(1.0); 8.916(0.6); 8.595(0.7); 8.530(0.8); 8.494(0.6); 8.464(0.6); 8.443(0.9); 8.428(0.6); 8.365(0.9); 8.355(0.8); 8.351(0.9); 8.329(16.0); 8.300(1.2); 8.259(5.8); 8.254(6.3); 8.247(6.1); 8.243(6.1); 8.235(10.5); 8.212(0.6); 8.200(0.6); 8.186(0.6); 8.053(0.7); 8.039(0.6); 8.023(0.5); 7.830(0.6); 7.777(0.7); 7.774(0.7); 7.755(0.8); 7.724(15.1); 7.629(4.7); 7.624(4.6); 7.609(5.8); 7.605(5.0); 7.544(0.7); 7.493(1.1); 7.480(8.1); 7.459(0.9); 7.438(0.6); 7.428(0.6); 7.360(0.6); 7.305(6.9); 7.292(6.7); 7.236(0.6); 7.213(4.8); 7.202(5.2); 7.194(4.7); 7.182(4.2); 6.719(0.5); 6.319(15.2); 5.295(5.7); 5.259(6.1); 4.729(6.2); 4.693(5.4); 4.609(0.8); 4.490(0.5); 4.476(0.6); 4.467(0.7); 4.455(0.5); 4.109(0.6); 4.087(0.6); 3.968(0.5); 3.928(0.6); 3.866(0.6); 3.839(5.1); 3.804(5.5); 3.771(0.5); 3.759(0.5); 3.743(0.5); 3.719(0.5); 3.681(0.5); 3.672(0.6); 3.659(0.6); 3.634(0.8); 3.616(0.8); 3.602(0.8); 3.595(0.7); 3.591(0.7); 3.556(1.0); 3.549(0.9); 3.534(0.9); 3.520(1.3); 3.516(1.3); 3.499(1.2); 3.483(1.6); 3.462(1.8); 3.448(1.8); 3.438(2.0); 3.430(2.1); 3.406(3.4); 3.333(4113.1); 3.280(8.7); 3.244(6.5); 3.208(1.0); 3.193(0.8); 3.173(0.7); 3.161(0.9); 3.149(0.8); 3.135(0.6); 3.129(0.7); 3.082(0.5); 2.995(1.9); 2.729(1.0); 2.675(6.4); 2.671(7.8); 2.667(5.9); 2.603(0.8); 2.574(1.2); 2.541(45.0); 2.506(1030.8); 2.502(1286.1); 2.498(932.7); 2.392(1.4); 2.369(1.1); 2.357(0.9); 2.333(6.5); 2.329(8.4); 2.324(6.3); 2.298(0.9); 2.290(1.0); 2.262(0.5); 2.255(0.6); 2.230(0.6); 2.091(0.6); 2.074(1.2); 1.953(0.6); 1.299(0.8); 1.258(1.1); 1.235(2.2); 1.108(2.7); 0.000(47.8); −2.805(0.6); −3.081(0.5); −3.161(0.5); −3.344(0.7); −3.572(0.5)
Example I-44: ¹H-NMR(400.0 MHz, DMSO):

δ = 8.366(11.1); 8.261(7.8); 7.841(11.3); 7.456(5.3); 7.443(5.0); 5.499(11.6); 4.626(1.7); 4.613(1.7); 4.602(2.5); 4.589(2.5); 4.538(2.2); 4.509(2.5); 4.495(1.8); 4.483(3.0); 4.472(4.1); 4.450(1.5); 4.419(2.1); 4.394(1.4); 4.381(2.0); 4.344(6.7); 4.329(2.4); 4.319(6.5); 4.300(0.4); 4.282(1.9); 3.403(0.6); 3.330(575.1); 3.274(0.5); 3.248(0.4); 3.046(13.3); 2.995(0.6); 2.710(0.4); 2.671(0.5); 2.541(64.2); 2.506(198.9); 2.502(235.3); 2.368(0.4); 2.328(1.5); 1.243(0.4); 1.236(0.5); 0.912(16.0); 0.000(9.1)
Example I-45: ¹H-NMR(300.2 MHz, CDCl3):

δ = 9.080(5.4); 9.064(5.6); 8.283(8.8); 8.003(7.7); 7.696(4.8); 7.679(4.7); 7.264(28.6); 5.302(16.0); 5.007(4.1); 4.960(4.5); 4.568(5.5); 4.565(5.8); 4.110(0.3); 3.969(4.7); 3.922(4.3); 3.618(2.5); 3.613(2.6); 3.571(3.1); 3.567(3.2); 3.173(4.5); 3.127(3.7); 2.047(1.5); 1.594(17.0); 1.284(0.4); 1.260(1.0); 1.246(0.4); 1.236(0.5); 0.913(0.8); 0.894(1.7); 0.887(1.2); 0.876(1.0); 0.868(2.1); 0.858(3.5); 0.850(1.5); 0.832(3.0); 0.823(2.3); 0.815(1.1); 0.804(1.5); 0.800(2.4); 0.781(1.2); 0.547(1.6); 0.527(2.0); 0.521(1.6); 0.513(1.5); 0.501(1.8); 0.492(1.8); 0.487(1.3); 0.466(1.3); 0.361(1.6); 0.338(2.1); 0.325(1.7); 0.317(1.5); 0.304(1.6); 0.301(1.7); 0.280(1.1); 0.069(0.6); 0.011(0.8); 0.000(21.5); −0.011(1.0)
Example I-46: ¹H-NMR(300.2 MHz, CDCl3):

δ = 8.282(4.3); 8.128(0.4); 8.020(3.8); 7.993(0.4); 7.730(4.5); 7.262(27.3); 5.610(1.2); 5.301(7.0); 4.991(1.9); 4.944(2.1); 4.676(2.6); 4.673(2.8); 4.158(0.4); 4.134(1.3); 4.110(1.3); 4.087(0.5); 3.992(2.2); 3.945(2.1); 3.552(1.2); 3.548(1.3); 3.506(1.6); 3.501(1.7); 3.177(2.2); 3.131(1.7); 2.046(5.9); 1.800(0.4); 1.788(0.4); 1.564(16.0); 1.546(0.4); 1.530(0.5); 1.518(0.4); 1.284(1.6); 1.260(3.3); 1.236(1.6); 0.891(0.9); 0.884(0.6); 0.870(1.0); 0.865(1.2); 0.855(1.3); 0.846(1.5); 0.836(1.2); 0.828(1.4); 0.812(1.3); 0.793(0.5); 0.562(0.7); 0.541(0.9); 0.535(0.7); 0.528(0.7); 0.515(0.9); 0.507(0.9); 0.501(0.6); 0.481(0.6); 0.371(0.8); 0.351(0.8); 0.348(1.0); 0.335(0.8); 0.326(0.7); 0.315(0.7); 0.311(0.8); 0.290(0.5); 0.011(0.6); 0.000(20.1); −0.011(1.0)
Example I-47: ¹H-NMR(400.1 MHz, DMSO):

δ = 8.493(7.6); 8.479(7.8); 8.402(16.0); 7.959(15.1); 7.582(7.4); 7.577(8.2); 7.483(5.0); 7.478(4.7); 7.469(5.0); 7.464(4.6); 5.871(15.9); 4.641(5.4); 4.605(7.2); 4.417(7.1); 4.381(5.4); 3.334(6.0); 3.321(28.8); 3.299(7.7); 3.070(6.6); 3.035(5.3); 2.530(0.6); 2.517(11.5); 2.513(23.6); 2.508(32.5); 2.504(24.0); 2.499(12.4); 0.654(0.5); 0.643(1.1); 0.632(2.4); 0.615(2.7); 0.611(3.4); 0.607(2.8); 0.595(1.7); 0.585(4.0); 0.581(4.8); 0.564(7.2); 0.552(4.0); 0.544(4.9); 0.534(3.4); 0.523(4.0); 0.520(3.5); 0.502(2.7); 0.490(1.1); 0.487(1.0); 0.475(0.4)
Example I-48: ¹H-NMR(400.1 MHz, DMSO):

δ = 8.439(0.7); 8.418(16.0); 7.994(0.7); 7.944(15.1); 7.720(4.0); 7.700(8.4); 7.681(4.7); 7.237(5.1); 7.218(4.8); 7.202(5.3); 7.182(4.8); 6.745(12.5); 5.647(1.4); 4.580(4.7); 4.544(8.2); 4.456(7.0); 4.420(4.1); 3.376(1.7); 3.325(239.0); 3.314(8.2); 3.278(7.1); 2.878(5.7); 2.842(4.9); 2.677(0.4); 2.563(0.4); 2.558(0.5); 2.530(1.3); 2.517(23.4); 2.512(47.9); 2.508(64.9); 2.503(45.8); 2.499(21.4); 2.461(0.4); 2.439(40.2); 2.339(0.3); 2.335(0.4); 1.779(0.4); 1.771(0.4); 1.593(0.4); 1.585(0.4); 0.674(0.9); 0.661(1.8); 0.655(1.4); 0.648(1.7); 0.642(2.3); 0.634(2.8); 0.628(2.8); 0.616(3.2); 0.609(2.8); 0.600(2.7); 0.596(1.7); 0.583(3.1);

0.570(2.1); 0.543(2.5); 0.530(2.9); 0.527(2.1); 0.517(1.8); 0.513(2.6); 0.503(2.2); 0.486(1.4); 0.458(2.4); 0.444(2.2); 0.439(2.4); 0.432(2.4); 0.425(2.0); 0.418(1.7); 0.413(1.8); 0.399(1.1)

Example I-49: $^1$H-NMR(400.0 MHz, CD3CN):

δ = 8.524(4.3); 8.369(2.6); 8.357(2.6); 8.228(4.5); 7.871(4.6); 7.460(2.6); 7.448(2.5); 4.635(2.9); 4.599(3.3); 4.115(3.2); 4.079(2.8); 4.068(0.6); 4.050(0.6); 3.595(3.7); 3.239(1.9); 3.205(3.3); 3.110(3.6); 3.075(2.1); 2.161(28.2); 2.155(30.3); 1.972(2.7); 1.965(1.9); 1.959(3.9); 1.953(17.9); 1.947(32.0); 1.940(42.2); 1.934(28.9); 1.928(14.8); 1.247(16.0); 1.222(0.7); 1.204(1.4); 1.186(0.7); 0.426(0.5); 0.418(0.7); 0.413(0.7); 0.403(1.3); 0.396(0.8); 0.389(0.7); 0.380(0.7); 0.080(0.6); 0.067(0.9); 0.056(1.2); 0.042(0.8); 0.033(1.1); 0.024(1.5); 0.016(1.2); 0.008(2.3); 0.000(51.6); −0.009(2.8); −0.020(0.9); −0.196(1.0); −0.206(1.0); −0.212(1.1); −0.219(1.3); −0.221(1.3); −0.229(0.9); −0.233(0.9); −0.242(0.7)

Example I-50: $^1$H-NMR(600.1 MHz, DMSO):

δ = 9.185(3.3); 9.183(3.1); 9.104(9.2); 9.102(8.8); 9.096(0.4); 8.865(3.0); 8.856(3.1); 8.727(8.4); 8.718(8.6); 8.413(15.9); 7.967(15.1); 7.781(1.9); 7.779(1.9); 7.772(1.9); 7.770(1.8); 7.558(5.4); 7.556(5.2); 7.549(5.3); 7.547(5.1); 6.689(1.6); 6.686(3.1); 6.682(1.6); 5.678(16.0); 5.529(0.4); 5.417(0.8); 5.408(1.7); 5.399(0.9); 4.657(6.1); 4.633(7.6); 4.452(7.5); 4.428(6.1); 4.313(2.5); 4.310(2.8); 4.304(2.7); 4.301(2.4); 3.327(85.6); 3.314(7.5); 3.291(7.6); 3.052(7.3); 3.029(6.2); 2.615(0.4); 2.542(0.8); 2.521(0.6); 2.521(0.8); 2.518(0.8); 2.506(52.7); 2.503(72.1); 2.500(52.9); 2.390(0.3); 2.387(0.5); 2.384(0.3); 1.261(1.5); 1.250(4.1); 1.249(4.2); 1.238(1.8); 0.886(1.8); 0.875(4.1); 0.873(4.2); 0.863(1.6); 0.651(2.0); 0.647(1.7); 0.643(2.7); 0.637(1.0); 0.633(2.3); 0.630(2.7); 0.626(2.3); 0.603(0.4); 0.560(1.8); 0.554(2.8); 0.543(8.0); 0.537(3.4); 0.532(15.9); 0.521(2.1); 0.514(0.9); 0.503(0.6); 0.000(6.5)

Example I-51: $^1$H-NMR(400.0 MHz, DMSO):

δ = 8.427(15.7); 8.127(3.6); 8.115(3.6); 7.988(15.7); 7.968(2.3); 7.963(3.4); 7.957(2.0); 7.944(2.0); 7.939(1.8); 7.315(2.3); 7.310(2.4); 7.303(2.4); 7.297(3.6); 7.292(3.3); 7.284(2.5); 7.280(2.1); 5.358(16.0); 4.687(5.7); 4.651(7.1); 4.375(6.9); 4.339(5.7); 3.327(53.0); 3.192(5.0); 3.157(6.5); 2.973(6.1); 2.938(4.6); 2.676(0.4); 2.672(0.5); 2.667(0.4); 2.525(1.4); 2.511(29.2); 2.507(57.6); 2.503(74.4); 2.498(53.1); 2.494(25.3); 2.334(0.4); 2.329(0.5); 2.325(0.4); 0.581(1.7); 0.571(2.2); 0.562(2.7); 0.552(5.4); 0.534(5.2); 0.531(5.2); 0.518(1.7); 0.496(1.9); 0.484(3.6); 0.476(4.2); 0.464(6.1); 0.456(3.2); 0.448(2.6); 0.443(2.7); 0.435(0.9); 0.430(1.7); 0.416(0.4); 0.000(2.9)

Example I-52: $^1$H-NMR(499.9 MHz, CDCl3):

δ = 8.278(5.4); 8.246(2.8); 8.236(2.8); 7.900(5.3); 7.108(3.8); 7.018(2.1); 7.008(2.1); 4.617(2.5); 4.589(3.8); 4.484(3.7); 4.456(2.5); 3.361(2.9); 3.331(3.3); 2.810(2.8); 2.781(2.5); 2.358(16.0); 0.846(0.7); 0.835(1.0); 0.832(1.0); 0.825(1.1); 0.820(1.2); 0.814(1.3); 0.810(1.2); 0.799(1.1); 0.697(0.8); 0.683(1.2); 0.675(1.2); 0.672(1.1); 0.664(1.2); 0.661(1.4); 0.650(1.1); 0.579(1.0); 0.567(1.4); 0.557(1.1); 0.553(1.2); 0.546(1.3); 0.532(0.9); 0.475(1.1); 0.463(1.2); 0.460(1.3); 0.454(1.2); 0.449(1.1); 0.442(1.1); 0.439(1.1); 0.427(0.8); 0.000(2.3)

Example I-53: $^1$H-NMR(300.2 MHz, CDCl3):

δ = 8.276(16.0); 7.988(14.0); 7.871(8.8); 7.844(9.6); 7.284(10.7); 7.266(20.5); 7.258(10.5); 5.010(7.1); 4.963(7.8); 4.392(9.6); 4.387(9.7); 4.134(0.4); 4.110(0.5); 3.950(4.3); 3.903(7.5); 3.661(4.7); 3.656(4.6); 3.614(5.5); 3.608(5.4); 3.071(8.2); 3.023(7.1); 2.046(2.0); 2.011(0.7); 1.630(2.2); 1.284(0.8); 1.260(2.2); 1.255(2.1); 1.236(0.7); 0.947(1.7); 0.927(2.8); 0.921(2.4); 0.910(2.4); 0.902(3.4); 0.891(3.5); 0.885(2.8); 0.866(3.4); 0.854(2.8); 0.834(2.3); 0.830(3.4); 0.818(3.5); 0.811(2.3); 0.799(3.0); 0.795(3.8); 0.776(2.4); 0.521(2.6); 0.501(3.5); 0.496(2.8); 0.486(2.6); 0.476(3.3); 0.466(3.2); 0.461(2.4); 0.440(2.4); 0.338(2.8); 0.317(3.3); 0.315(3.5); 0.302(3.0); 0.294(2.7); 0.281(3.0); 0.278(3.1); 0.258(2.0); 0.070(0.7); 0.011(0.4); 0.000(10.8); −0.011(0.6)

Example I-54: $^1$H-NMR(300.2 MHz, CDCl3):

δ = 8.292(2.3); 8.283(9.6); 8.279(7.8); 8.265(7.4); 7.886(7.6); 7.264(19.9); 5.816(8.7); 4.633(14.8); 3.747(3.8); 3.695(4.8); 3.362(4.4); 3.311(3.3); 2.047(0.6); 2.010(2.5); 1.604(16.0); 1.260(0.4); 1.254(0.4); 0.942(1.3); 0.933(0.9); 0.926(0.7); 0.914(1.1); 0.907(1.4); 0.899(2.7); 0.880(0.8); 0.859(0.8); 0.849(1.5); 0.845(1.9); 0.839(2.0); 0.834(1.7); 0.814(0.4); 0.805(1.5); 0.784(1.9); 0.766(1.6); 0.756(4.6); 0.750(5.2); 0.740(2.4); 0.736(2.3); 0.708(0.5); 0.011(0.4); 0.000(12.6); −0.011(0.6)

Example I-55: $^1$H-NMR(300.2 MHz, CDCl3):

δ = 8.289(3.9); 8.280(3.5); 8.020(3.6); 8.015(3.5); 7.630(3.4); 7.414(0.6); 7.403(6.2); 7.396(2.7); 7.391(4.1); 7.381(2.4); 7.373(8.2); 7.363(1.0); 7.263(16.2); 7.198(0.5); 7.187(4.4); 7.179(1.4); 7.165(4.8); 7.157(4.5); 7.146(0.6); 7.142(1.1); 7.135(3.0); 7.124(0.4); 5.301(2.3); 5.020(1.5); 4.973(1.6); 4.947(1.3); 4.900(1.5); 4.590(2.1); 4.585(2.2); 4.546(2.3); 4.203(1.5); 4.156(1.4); 3.996(1.7); 3.949(1.6); 3.613(1.0); 3.608(1.0); 3.566(1.2); 3.561(1.6); 3.385(0.7); 3.340(1.3); 3.230(1.6); 3.184(1.7); 3.142(1.6); 3.096(1.5); 1.597(16.0); 1.255(0.3); 0.978(0.3); 0.959(0.6); 0.953(0.5); 0.941(0.5); 0.933(0.7); 0.922(0.7); 0.916(0.6); 0.897(0.7); 0.890(0.6); 0.882(0.3); 0.866(0.9); 0.855(1.0); 0.847(0.7); 0.834(1.2); 0.831(1.2); 0.820(0.6); 0.810(1.0); 0.800(1.1); 0.791(0.4); 0.780(0.5); 0.775(0.8); 0.756(0.4); 0.564(0.6); 0.557(0.5); 0.544(0.8); 0.538(0.9); 0.530(0.9); 0.522(0.7); 0.519(0.8); 0.509(1.0); 0.503(0.9); 0.497(0.5); 0.483(0.5); 0.476(0.5); 0.389(0.5); 0.377(0.6); 0.365(0.7); 0.353(1.2); 0.344(0.7); 0.341(0.8); 0.333(1.0); 0.317(0.7); 0.308(0.4); 0.296(0.4); 0.000(10.4); −0.011(0.5)

Example I-56: $^1$H-NMR(300.2 MHz, CDCl3):

δ = 8.345(5.5); 8.311(5.8); 8.148(6.5); 7.904(6.3); 7.415(0.6); 7.404(5.9); 7.397(2.0); 7.382(2.1); 7.374(7.1); 7.364(0.8); 7.263(27.1); 7.068(0.7); 7.057(7.1); 7.050(2.1); 7.035(1.9); 7.027(5.9); 7.016(0.6); 5.301(1.7); 4.635(5.0); 4.633(5.1); 4.571(1.4); 4.523(3.3); 4.459(4.2); 4.411(1.8); 4.158(0.4); 4.134(1.2); 4.110(1.2); 4.087(0.4); 3.360(2.8); 3.311(3.3); 2.767(2.7); 2.719(2.3); 2.046(5.6); 1.588(16.0); 1.284(1.6); 1.260(3.2); 1.236(1.5); 0.723(0.9); 0.714(0.5); 0.705(1.2); 0.698(1.4); 0.686(1.7); 0.680(2.0); 0.674(1.7); 0.660(2.1); 0.650(1.9); 0.632(0.9); 0.594(1.1); 0.577(1.6); 0.569(0.7); 0.555(2.0); 0.552(1.9); 0.548(1.7); 0.539(1.3); 0.531(1.5); 0.519(1.6); 0.513(0.8); 0.502(0.6); 0.494(1.0); 0.477(0.3); 0.011(0.6); 0.000(17.7); −0.011(0.7)

-continued

Example I-57: $^1$H-NMR(400.0 MHz, DMSO):

δ = 8.936(14.6); 8.409(13.9); 7.964(13.2); 5.523(16.0); 4.752(4.5); 4.716(6.8); 4.591(6.6); 4.555(4.4); 3.551(4.6); 3.517(7.5); 3.426(7.5); 3.391(4.6); 3.324(50.7); 2.676(0.4); 2.671(0.6); 2.667(0.4); 2.622(0.4); 2.542(2.3); 2.511(35.9); 2.507(68.9); 2.502(87.6); 2.498(61.7); 2.493(29.0); 2.333(0.4); 2.329(0.6); 2.324(0.4); 0.981(1.1); 0.967(1.5); 0.961(1.6); 0.956(2.0); 0.948(1.7); 0.940(2.0); 0.936(1.8); 0.922(1.6); 0.780(1.1); 0.765(1.2); 0.759(2.1); 0.755(1.9); 0.744(2.4); 0.735(2.1); 0.721(1.8); 0.635(0.8); 0.621(3.6); 0.617(4.0); 0.602(4.0); 0.597(4.3); 0.591(3.3); 0.577(2.6); 0.571(2.1); 0.556(0.4); 0.000(36.7); −0.009(1.3)

Example I-58: $^1$H-NMR(300.2 MHz, CDCl3):

δ = 8.377(16.0); 8.269(15.1); 7.998(13.1); 7.543(15.6); 7.265(21.6); 4.963(6.7); 4.916(7.3); 4.465(9.5); 4.461(9.1); 3.962(7.7); 3.915(7.1); 3.645(5.0); 3.639(4.7); 3.599(5.8); 3.594(5.5); 3.073(7.4); 3.027(6.4); 1.620(12.6); 0.976(1.6); 0.957(2.7); 0.950(2.3); 0.939(2.5); 0.931(3.1); 0.920(3.3); 0.914(2.6); 0.895(3.0); 0.871(2.3); 0.852(2.2); 0.847(3.0); 0.835(3.3); 0.828(2.2); 0.816(2.8); 0.812(3.4); 0.793(2.3); 0.538(2.4); 0.517(3.4); 0.512(2.7); 0.502(2.4); 0.492(3.1); 0.482(3.1); 0.477(2.2); 0.456(2.3); 0.370(2.7); 0.349(3.1); 0.346(3.3); 0.333(2.9); 0.326(2.5); 0.312(2.8); 0.310(2.9); 0.289(1.8); 0.010(0.6); 0.000(16.2); −0.011(0.8)

Example I-59: $^1$H-NMR(400.0 MHz, DMSO):

δ = 9.725(0.4); 8.923(0.5); 8.423(0.4); 8.414(1.4); 8.409(1.7); 8.402(1.5); 8.398(1.6); 8.360(0.3); 8.326(15.1); 8.316(1.5); 8.258(4.6); 8.254(5.3); 8.247(5.0); 8.242(5.1); 8.222(1.4); 8.218(1.4); 8.203(1.5); 8.198(1.6); 8.186(0.4); 8.058(8.5); 8.045(8.7); 8.024(0.5); 7.901(2.4); 7.890(2.5); 7.718(15.2); 7.600(4.2); 7.596(4.6); 7.581(4.7); 7.576(4.8); 7.550(1.4); 7.538(1.5); 7.530(1.4); 7.519(1.4); 7.243(2.0); 7.231(1.9); 7.196(4.8); 7.183(6.5); 7.177(5.8); 7.169(8.0); 7.157(3.9); 6.312(16.0); 6.170(0.3); 6.142(3.8); 5.304(6.1); 5.268(6.5); 4.843(1.6); 4.815(1.7); 4.754(6.3); 4.717(5.6); 4.287(1.1); 4.280(1.1); 4.259(1.0); 4.252(1.1); 3.881(5.2); 3.846(5.5); 3.813(1.4); 3.329(723.3); 3.293(5.5); 2.995(1.2); 2.960(1.0); 2.916(0.8); 2.711(0.9); 2.671(2.5); 2.542(218.0); 2.506(311.5); 2.502(415.4); 2.498(329.3); 2.367(1.2); 2.329(2.7); 2.293(0.3); 1.258(0.4); 1.235(1.8); 0.146(0.5); 0.000(109.5); −0.150(0.6)

Example I-60: $^1$H-NMR(400.0 MHz, DMSO):

δ = 8.441(16.0); 8.191(8.0); 8.179(8.3); 8.001(15.1); 7.552(3.8); 7.540(7.1); 7.527(3.6); 5.517(12.9); 4.688(5.6); 4.652(7.3); 4.452(7.2); 4.416(5.5); 3.360(41.0); 3.303(4.5); 3.268(5.7); 3.052(5.5); 3.017(4.2); 3.005(0.3); 2.720(0.4); 2.550(72.9); 2.529(0.6); 2.515(8.8); 2.511(11.8); 2.506(9.1); 2.376(0.4); 0.652(0.6); 0.639(1.6); 0.632(1.2); 0.621(2.4); 0.612(3.3); 0.606(2.6); 0.594(7.1); 0.580(1.6); 0.574(3.4); 0.562(2.7); 0.547(1.6); 0.535(7.6); 0.516(6.2); 0.507(3.2); 0.495(2.3); 0.487(1.9); 0.000(2.7)

Example I-61: $^1$H-NMR(400.0 MHz, DMSO):

δ = 8.823(0.9); 8.355(12.0); 8.157(0.5); 8.145(0.5); 8.051(6.4); 8.039(6.7); 7.941(0.8); 7.837(12.1); 7.463(1.3); 7.457(3.0); 7.445(5.6); 7.432(2.9); 6.737(0.8); 5.490(11.0); 4.626(1.7); 4.609(1.7); 4.602(2.5); 4.586(2.6); 4.534(2.1); 4.508(2.7); 4.490(1.8); 4.482(3.0); 4.467(2.9); 4.451(1.6); 4.415(2.2); 4.391(1.3); 4.369(1.3); 4.357(2.2); 4.332(9.3); 4.323(8.1); 4.286(1.2); 3.344(62.3); 3.154(1.4); 3.118(6.3); 3.102(5.5); 3.066(1.2); 2.545(58.9); 2.510(17.9); 2.506(23.4); 2.502(18.0); 1.234(0.3); 1.001(1.5); 0.919(16.0); 0.751(0.4); 0.000(4.2)

Example I-62: $^1$H-NMR(400.0 MHz, DMSO):

δ = 8.574(16.0); 8.430(7.7); 8.398(0.3); 7.989(7.6); 5.215(4.8); 4.686(2.0); 4.649(2.8); 4.474(2.7); 4.438(1.9); 3.487(3.0); 3.453(4.5); 3.349(389.1); 3.309(4.1); 2.996(0.4); 2.713(0.5); 2.673(0.7); 2.545(26.1); 2.543(41.4); 2.508(48.7); 2.504(63.9); 2.500(48.7); 2.369(0.4); 2.331(0.6); 1.235(0.5); 0.851(0.5); 0.836(0.6); 0.822(0.8); 0.803(1.1); 0.780(0.8); 0.772(0.7); 0.754(0.7); 0.740(0.6); 0.659(0.8); 0.639(0.8); 0.633(0.9); 0.625(0.9); 0.608(2.4); 0.586(1.2); 0.573(1.3); 0.556(0.9); 0.541(0.6); 0.526(0.5); 0.307(0.8); 0.299(1.1); 0.281(1.0); 0.275(0.8); 0.266(0.8); 0.239(0.4); 0.000(0.4)

Example I-63: $^1$H-NMR(400.0 MHz, DMSO):

δ = 8.721(1.1); 8.597(1.0); 8.527(1.4); 8.503(16.0); 8.438(7.5); 8.413(0.9); 8.397(1.3); 8.332(1.8); 8.320(1.7); 8.285(1.6); 8.101(1.4); 7.970(11.4); 7.786(1.4); 7.761(0.8); 7.726(0.9); 7.643(1.3); 7.543(2.3); 7.522(3.1); 7.516(2.9); 7.448(4.8); 7.428(3.0); 6.626(0.9); 6.412(5.8); 5.165(0.9); 4.299(3.1); 4.283(5.0); 4.267(3.0); 3.355(4984.0); 3.310(5.4); 3.278(3.7); 3.263(5.2); 3.224(0.8); 3.002(2.1); 2.718(2.3); 2.680(6.8); 2.550(214.4); 2.510(791.2); 2.507(670.6); 2.376(2.0); 2.337(5.5); 1.242(4.8); 0.006(2.0)

Example I-64: $^1$H-NMR(400.0 MHz, DMSO):

δ = 9.346(0.7); 8.534(0.6); 8.404(16.0); 8.354(1.6); 8.310(0.8); 8.301(1.3); 8.273(12.4); 8.114(1.6); 8.013(16.0); 7.752(0.6); 7.559(1.7); 7.554(2.3); 7.535(4.2); 7.520(2.1); 7.516(2.0); 7.408(8.4); 7.404(8.5); 7.333(1.0); 7.329(1.1); 7.314(2.8); 7.296(3.3); 7.281(1.9); 7.277(1.7); 7.262(0.3); 7.203(0.5); 7.177(6.8); 7.159(7.1); 7.151(4.5); 7.143(3.3); 7.130(2.5); 7.043(0.6); 6.864(0.4); 6.861(0.4); 6.847(0.4); 6.547(0.7); 6.543(0.8); 5.584(0.6); 5.365(14.9); 4.265(1.5); 4.229(9.9); 4.219(9.7); 4.184(1.5); 4.041(0.4); 4.028(0.4); 3.788(0.7); 3.780(0.7); 3.686(0.7); 3.506(0.8); 3.480(0.8); 3.383(0.8); 3.343(91.6); 3.001(0.5); 2.962(2.4); 2.927(8.1); 2.903(8.2); 2.868(3.4); 2.834(8.8); 2.828(8.6); 2.792(1.0); 2.716(0.5); 2.546(98.6); 2.511(31.5); 2.507(41.6); 2.502(31.3); 2.372(0.5); 1.233(0.4); 0.008(0.4); 0.000(9.9)

Example I-65: $^1$H-NMR(400.0 MHz, DMSO):

δ = 8.448(0.6); 8.417(16.0); 8.400(0.3); 8.334(0.3); 8.313(11.8); 7.985(16.0); 7.329(8.2); 7.325(8.2); 5.525(8.8); 5.521(8.9); 4.614(4.1); 4.578(5.6); 4.393(5.1); 4.357(7.5); 3.336(107.5); 3.303(4.1); 3.269(5.8); 3.139(5.0); 3.105(3.4); 2.713(0.4); 2.543(83.0); 2.508(40.8); 2.504(53.1); 2.500(38.8); 2.369(0.4); 2.330(0.3); 1.235(0.5); 0.699(0.5); 0.686(0.6); 0.681(0.7); 0.670(1.3); 0.656(1.3); 0.651(1.5); 0.638(1.5); 0.631(0.9); 0.619(2.2); 0.601(2.7); 0.588(2.4); 0.568(1.4); 0.555(1.6); 0.551(1.6); 0.537(1.4); 0.521(0.7); 0.507(0.8); 0.483(0.9); 0.469(0.9); 0.465(0.9); 0.455(1.8); 0.442(1.9); 0.429(1.7); 0.416(1.4); 0.399(0.9); 0.347(1.0); 0.334(1.2); 0.330(1.3); 0.321(1.9); 0.304(1.9); 0.295(1.2); 0.290(1.4); 0.281(0.9); 0.263(0.6); 0.008(0.6); 0.000(13.0); −0.008(0.5)

-continued

Example I-66: $^1$H-NMR(400.0 MHz, DMSO):

δ = 8.452(4.8); 8.293(2.8); 8.281(3.0); 8.236(5.3); 7.920(5.3); 7.315(2.3); 7.302(2.2); 5.777(3.9); 5.587(4.5); 4.477(5.9); 3.662(16.0); 3.652(0.8); 3.370(0.6); 3.338(185.7); 3.310(0.4); 3.234(1.3); 3.199(2.1); 3.118(2.3); 3.082(1.4); 2.671(0.3); 2.542(36.3); 2.525(1.1); 2.511(20.4); 2.507(41.2); 2.502(54.1); 2.498(39.3); 2.493(19.3); 2.329(0.4); 2.160(12.2); 2.126(0.3); 0.000(4.0)

Example I-67: $^1$H-NMR(400.0 MHz, DMSO):

δ = 8.557(7.3); 8.551(7.4); 8.398(16.0); 7.961(15.2); 7.920(4.4); 7.913(4.4); 7.899(4.9); 7.892(4.8); 7.482(7.6); 7.461(7.0); 5.673(15.6); 4.637(5.6); 4.601(7.5); 4.405(7.3); 4.369(5.6); 4.039(0.4); 4.021(0.4); 3.330(63.7); 3.297(7.4); 3.033(7.1); 2.998(5.8); 2.673(0.4); 2.508(41.4); 2.503(54.0); 2.499(40.0); 2.330(0.3); 1.990(1.5); 1.910(0.6); 1.193(0.4); 1.175(0.8); 1.158(0.4); 0.616(0.6); 0.609(1.0); 0.598(1.6); 0.594(2.1); 0.576(3.8); 0.562(0.9); 0.552(3.1); 0.545(4.3); 0.531(8.6); 0.510(8.8); 0.504(5.9); 0.488(2.0); 0.480(1.2); 0.467(0.8); 0.008(1.1); 0.000(28.5); −0.008(1.4)

Example I-68: $^1$H-NMR(400.0 MHz, DMSO):

δ = 8.581(15.4); 8.493(16.0); 8.452(8.1); 8.440(9.6); 8.426(1.7); 8.024(15.6); 7.997(0.7); 7.657(7.5); 7.645(7.2); 7.379(1.5); 7.367(6.5); 7.349(6.2); 7.284(0.7); 7.276(1.6); 7.265(10.6); 7.258(8.1); 7.251(6.9); 7.232(1.9); 7.230(1.9); 7.218(3.5); 7.211(2.8); 7.202(2.5); 7.199(3.3); 7.192(2.5); 7.183(1.6); 7.176(1.4); 5.327(1.3); 5.285(13.7); 4.462(4.7); 4.426(6.7); 4.293(6.7); 4.257(4.7); 3.356(59.0); 3.135(4.4); 3.100(6.9); 3.053(5.2); 3.001(6.8); 2.966(4.4); 2.926(0.4); 2.904(0.9); 2.891(1.1); 2.870(2.4); 2.858(2.6); 2.839(2.3); 2.826(3.4); 2.814(2.2); 2.795(2.5); 2.783(2.3); 2.762(1.1); 2.750(0.9); 2.548(98.1); 2.513(17.2); 2.509(21.7); 2.504(16.0); 2.374(0.5); 1.641(1.0); 1.629(1.3); 1.608(2.3); 1.595(2.3); 1.577(1.7); 1.564(1.5); 1.507(1.6); 1.494(1.8); 1.475(2.3); 1.463(2.2); 1.441(1.3); 1.429(1.0); 0.000(3.0)

Example I-69: $^1$H-NMR(400.0 MHz, CD3CN):

δ = 8.538(14.7); 8.394(8.8); 8.382(9.0); 8.203(14.9); 8.160(0.4); 7.907(14.8); 7.483(7.8); 7.471(7.5); 7.282(1.4); 7.276(11.1); 7.271(4.6); 7.260(5.0); 7.255(16.0); 7.161(14.1); 7.140(9.7); 4.440(7.0); 4.404(9.5); 4.221(9.2); 4.185(6.7); 4.085(0.4); 4.068(1.3); 4.050(1.4); 4.032(0.5); 3.565(8.6); 3.109(5.5); 3.075(10.4); 3.004(10.1); 2.970(5.3); 2.844(1.1); 2.831(1.3); 2.811(2.6); 2.798(2.8); 2.770(2.8); 2.767(2.3); 2.749(2.2); 2.736(2.4); 2.718(2.9); 2.705(2.8); 2.685(1.3); 2.672(1.2); 2.150(20.4); 2.107(0.4); 1.972(6.2); 1.964(2.0); 1.958(4.5); 1.952(23.0); 1.946(41.5); 1.940(55.3); 1.934(37.9); 1.928(19.4); 1.769(0.3); 1.701(1.3); 1.688(1.5); 1.666(3.1); 1.657(1.7); 1.653(3.0); 1.636(3.0); 1.622(2.9); 1.616(3.2); 1.603(3.2); 1.586(3.0); 1.582(1.9); 1.573(3.0); 1.551(1.5); 1.538(1.2); 1.221(1.6); 1.204(3.2); 1.186(1.6); 0.146(0.6); 0.022(0.3); 0.020(0.4); 0.0192(0.4); 0.0185(0.5); 0.018(0.5); 0.017(0.5); 0.008(5.6); 0.000(138.8); −0.009(5.5); −0.150(0.6)

Example I-70: $^1$H-NMR(400.0 MHz, DMSO):

δ = 20.014(0.6); 8.732(0.4); 8.627(0.5); 8.575(2.4); 8.519(7.2); 8.466(0.5); 8.443(7.7); 8.434(1.8); 8.422(1.7); 8.387(0.7); 8.345(4.0); 8.333(4.3); 7.863(7.8); 7.641(3.5); 7.629(3.4); 7.379(1.5); 7.367(1.7); 7.356(6.1); 7.334(7.5); 7.041(6.8); 7.019(6.2); 5.471(6.8); 5.325(0.8); 4.601(2.3); 4.564(3.1); 4.374(3.1); 4.338(2.5); 3.361(2793.1); 3.267(6.8); 3.255(6.0); 3.219(2.1); 3.163(1.6); 3.053(5.6); 2.996(1.2); 2.714(1.0); 2.673(2.9); 2.543(145.3); 2.509(300.0); 2.504(388.0); 2.500(283.9); 2.370(0.7); 2.331(2.5); 2.196(0.8); 2.029(0.9); 2.010(1.5); 1.991(1.6); 1.627(1.1); 1.501(2.2); 1.438(1.2); 1.417(1.3); 1.391(1.4); 1.360(2.3); 1.330(1.8); 1.236(7.5); 1.199(16.0); 1.171(1.1); 1.129(15.6); 1.067(1.0); 0.854(2.0); 0.837(1.0); 0.000(19.6)

Example I-71: $^1$H-NMR(300.2 MHz, CDCl3):

δ = 8.349(4.5); 8.341(6.1); 8.303(5.1); 8.295(3.7); 8.268(8.6); 7.886(8.4); 7.266(12.8); 5.696(9.5); 5.612(0.9); 5.302(0.5); 4.642(15.5); 3.782(4.0); 3.730(5.0); 3.336(4.5); 3.285(3.6); 1.789(0.3); 1.634(16.0); 1.531(0.4); 1.254(0.8); 0.918(1.2); 0.909(1.0); 0.890(1.4); 0.884(2.0); 0.879(2.7); 0.875(2.4); 0.846(3.5); 0.840(3.1); 0.834(2.1); 0.808(1.6); 0.780(2.3); 0.768(1.6); 0.747(7.0); 0.737(3.8); 0.730(1.7); 0.708(0.6); 0.070(1.0); 0.011(0.3); 0.000(8.3)

Example I-72: $^1$H-NMR(300.2 MHz, CDCl3):

δ = 8.261(3.1); 8.113(0.7); 8.027(2.0); 8.018(2.4); 7.986(0.8); 7.924(2.8); 7.915(2.4); 7.860(3.3); 7.268(4.6); 6.110(2.8); 5.302(0.9); 4.814(0.7); 4.784(1.1); 4.731(0.7); 4.680(0.3); 4.634(0.4); 4.586(3.6); 4.576(3.8); 4.528(0.4); 4.006(16.0); 3.932(0.4); 3.563(1.9); 3.511(2.3); 3.081(2.1); 3.029(1.7); 2.047(1.3); 1.697(1.9); 1.284(0.7); 1.254(2.7); 1.236(0.7); 1.224(0.5); 1.208(0.4); 1.147(0.4); 0.877(0.3); 0.849(2.7); 0.839(3.9); 0.811(0.5); 0.801(0.6); 0.786(0.4); 0.746(0.7); 0.708(1.7); 0.704(2.0); 0.670(1.7); 0.666(1.8); 0.641(0.7); 0.633(0.5); 0.628(0.5); 0.070(0.4); 0.000(2.9)

Example I-73: $^1$H-NMR(400.0 MHz, DMSO):

δ = 8.699(1.3); 8.542(1.1); 8.508(0.8); 8.408(1.2); 8.404(1.2); 8.393(12.8); 8.353(1.2); 8.340(10.2); 8.303(1.3); 8.124(1.2); 8.084(1.5); 8.076(0.9); 8.009(12.7); 7.974(0.5); 7.632(5.5); 7.620(5.5); 7.537(2.3); 7.521(3.8); 7.502(2.0); 7.412(0.7); 7.399(0.7); 7.376(0.3); 7.357(0.6); 7.345(0.8); 7.322(1.8); 7.307(3.3); 7.288(3.6); 7.274(2.3); 7.270(2.3); 7.259(2.0); 7.245(2.2); 7.225(0.9); 7.220(1.0); 7.206(1.3); 7.187(1.6); 7.169(6.7); 7.150(7.5); 7.141(5.4); 7.119(3.7); 7.111(2.7); 7.092(1.6); 7.046(0.6); 7.027(0.8); 7.010(0.5); 6.970(0.8); 6.957(0.8); 6.851(0.4); 6.832(0.5); 6.726(0.9); 6.617(0.6); 6.018(0.4); 5.903(0.7); 5.849(0.5); 5.814(1.0); 5.616(1.0); 5.568(0.5); 5.551(0.9); 5.340(11.8); 5.319(0.4); 5.306(0.5); 5.205(0.5); 5.191(0.8); 5.176(0.4); 5.064(0.4); 5.018(0.4); 4.761(0.4); 4.738(0.4); 4.408(0.3); 4.313(0.4); 4.198(16.0); 4.149(0.6); 4.126(0.5); 4.001(1.8); 3.986(1.7); 3.971(0.7); 3.749(0.4); 3.740(0.4); 3.721(0.4); 3.704(1.2); 3.683(0.6); 3.543(2.7); 3.415(0.3); 3.377(2.0); 3.338(374.1); 3.282(0.7); 3.256(0.3); 3.018(0.4); 2.997(2.6); 2.926(0.4); 2.820(1.7); 2.795(12.5); 2.768(6.6); 2.733(1.6); 2.713(0.9); 2.691(0.5); 2.673(0.8); 2.543(165.1); 2.508(94.1); 2.504(118.8); 2.500(90.6); 2.369(0.9); 2.331(0.8); 2.289(0.5); 2.255(0.4); 0.000(5.6)

Example I-74: $^1$H-NMR(400.0 MHz, DMSO):

δ = 8.609(0.8); 8.474(0.8); 8.462(0.5); 8.417(0.4); 8.399(0.4); 8.383(12.7); 8.344(9.3); 8.309(0.9); 8.132(0.7); 8.115(1.0); 8.056(0.5); 8.027(12.9); 7.600(5.7); 7.588(5.4); 7.430(6.8); 7.394(0.7); 7.372(0.9); 7.360(0.7); 7.352(0.7); 7.333(0.8); 7.319(3.5); 7.306(16.0); 7.296(6.1); 7.288(3.7); 7.274(1.9); 7.243(1.1); 7.225(0.8);

-continued 7.207(0.8); 7.200(0.5); 7.177(0.7); 7.163(0.8); 7.140(0.6); 7.076(0.3); 6.971(0.7); 6.965(0.7); 6.950(0.6); 6.771(0.4); 5.871(0.5); 5.467(0.6); 5.414(0.5); 5.339(10.4); 4.210(2.8); 4.196(0.3); 4.175(6.0); 4.144(0.4); 4.122(5.9); 4.087(2.9); 3.979(0.5); 3.969(0.6); 3.665(0.4); 3.635(0.9); 3.544(0.5); 3.405(0.5); 3.337(383.2); 3.299(1.3); 3.258(0.6); 3.224(0.5); 2.996(3.2); 2.813(2.1); 2.779(6.1); 2.753(6.5); 2.736(12.2); 2.719(2.5); 2.701(0.5); 2.677(0.8); 2.672(0.9); 2.668(0.7); 2.646(0.3); 2.570(0.5); 2.543(177.7); 2.526(3.4); 2.508(92.8); 2.503(118.9); 2.499(87.7); 2.369(0.9); 2.334(0.7); 2.330(0.9); 2.326(0.7); 2.314(0.4); 1.235(0.3); 0.000(6.1)
Example I-75: $^1$H-NMR(400.0 MHz, DMSO):

δ = 8.557(15.2); 8.439(8.3); 8.427(8.7); 8.387(15.2); 8.327(0.6); 8.314(0.6); 8.300(1.2); 8.102(1.2); 8.036(16.0); 7.608(6.9); 7.596(6.7); 7.412(4.8); 7.398(6.0); 7.391(6.5); 7.376(5.4); 7.135(6.0); 7.113(10.4); 7.091(5.2); 7.041(0.7); 7.018(0.9); 7.002(0.6); 6.995(0.3); 6.760(0.5); 6.747(0.5); 5.594(0.5); 5.251(14.4); 4.185(0.6); 4.148(14.5); 4.111(0.6); 3.485(0.5); 3.450(0.9); 3.422(0.6); 3.359(24.5); 3.257(0.4); 2.887(2.4); 2.853(7.9); 2.830(7.9); 2.809(2.8); 2.795(2.6); 2.775(6.9); 2.742(6.7); 2.721(0.5); 2.708(2.5); 2.551(50.7); 2.534(0.5); 2.516(12.2); 2.512(16.4); 2.508(12.5); 0.000(6.2)
Example I-76: $^1$H-NMR(400.0 MHz, DMSO):

δ = 8.581(0.5); 8.575(0.6); 8.550(0.4); 8.539(11.4); 8.525(0.4); 8.384(12.5); 8.373(6.8); 8.360(6.9); 8.136(0.6); 7.896(12.6); 7.596(5.7); 7.583(5.5); 5.597(10.8); 4.447(3.9); 4.411(5.1); 4.197(3.5); 4.162(2.7); 4.160(2.7); 3.365(0.3); 3.337(118.7); 3.102(16.0); 2.997(0.4); 2.672(0.3); 2.543(71.1); 2.526(1.1); 2.512(21.2); 2.508(41.3); 2.503(53.2); 2.499(38.1); 2.495(18.4); 2.330(0.3); 1.570(0.6); 1.513(0.6); 1.454(0.9); 1.424(12.5); 1.397(1.1); 1.367(12.5); 1.223(0.6); 1.177(12.5); 1.120(12.4); 0.000(6.8)
Example I-77: $^1$H-NMR(400.0 MHz, DMSO):

δ = 8.564(1.4); 8.531(14.7); 8.465(1.7); 8.430(15.8); 8.415(0.4); 8.401(8.6); 8.388(8.9); 8.295(0.9); 8.283(0.9); 8.060(1.7); 7.982(16.0); 7.613(7.2); 7.601(7.0); 6.675(0.7); 6.662(0.7); 5.290(0.7); 5.062(14.8); 4.172(3.9); 4.137(8.3); 4.085(8.3); 4.050(3.9); 3.947(0.4); 3.735(0.3); 3.723(0.3); 3.376(1.0); 3.368(0.6); 3.339(213.1); 3.305(0.6); 2.963(5.3); 2.929(7.0); 2.901(0.3); 2.729(6.6); 2.713(0.5); 2.695(5.1); 2.677(0.5); 2.673(0.6); 2.668(0.4); 2.543(97.3); 2.526(1.5); 2.512(35.7); 2.508(72.1); 2.504(94.2); 2.499(68.4); 2.495(33.4); 2.432(0.6); 2.410(1.8); 2.388(2.7); 2.368(2.3); 2.353(0.5); 2.345(0.6); 2.335(0.5); 2.330(0.7); 2.326(0.5); 1.956(0.3); 1.934(2.0); 1.911(3.0); 1.887(2.6); 1.863(1.7); 1.851(0.9); 1.828(1.9); 1.804(3.0); 1.779(2.6); 1.756(0.9); 1.694(0.5); 1.671(1.1); 1.647(2.1); 1.625(2.3); 1.605(2.4); 1.587(2.0); 1.577(2.0); 1.556(1.3); 1.540(0.7); 1.530(1.2); 1.525(1.3); 1.501(2.3); 1.476(1.9); 1.460(0.7); 1.438(0.6); 1.406(1.6); 1.401(1.6); 1.393(1.4); 1.386(1.4); 1.234(0.5); 0.008(0.7); 0.000(17.6); −0.009(0.7)
Example I-78: $^1$H-NMR(400.0 MHz, DMSO):

δ = 17.141(0.9); 8.469(3.4); 8.397(3.8); 8.316(4.3); 8.167(2.2); 8.154(1.9); 8.077(4.1); 7.679(0.9); 7.193(16.0); 6.430(1.6); 6.418(1.7); 5.277(1.6); 3.708(1.1); 3.677(1.4); 3.670(1.3); 3.576(1.0); 3.542(1.6); 3.455(2.4); 3.413(2.3); 3.400(2.6); 3.385(2.6); 3.370(6.4); 3.334(3525.6); 3.294(4.3); 3.263(1.5); 3.249(1.1); 3.221(1.1); 3.206(1.3); 3.189(0.9); 2.711(1.2); 2.671(10.8); 2.591(1.9); 2.579(1.9); 2.573(1.6); 2.542(240.5); 2.507(1420.4); 2.502(1769.6); 2.498(1247.5); 2.400(1.2); 2.368(1.6); 2.334(8.7); 2.329(11.1); 2.325(8.1); 2.290(1.4); 2.278(0.9); 1.299(1.2); 1.259(1.5); 1.235(4.8); 1.112(1.2); 0.865(1.1); 0.854(1.4); 0.840(1.2); 0.146(1.2); 0.008(11.6); 0.000(290.5); −0.009(10.4); −0.150(1.5)
Example I-79: $^1$H-NMR(400.0 MHz, DMSO):

δ = 19.997(0.4); 8.546(12.2); 8.538(1.1); 8.522(0.9); 8.417(15.0); 8.407(7.4); 8.380(0.6); 8.354(0.4); 8.317(1.5); 8.303(0.3); 8.291(0.3); 8.035(0.8); 7.969(12.8); 7.513(5.8); 7.501(5.9); 7.131(4.8); 7.109(9.0); 7.093(2.5); 7.087(5.7); 7.076(1.1); 7.062(0.5); 6.933(0.5); 6.911(0.7); 6.882(6.0); 6.871(6.2); 6.865(3.5); 6.859(5.2); 6.848(4.9); 6.816(0.4); 6.739(0.4); 5.581(10.8); 5.520(0.3); 4.908(0.6); 4.526(3.4); 4.490(5.5); 4.394(5.5); 4.358(3.5); 3.816(0.4); 3.800(0.5); 3.750(0.4); 3.593(16.0); 3.463(0.4); 3.456(0.4); 3.427(0.4); 3.384(0.5); 3.334(1146.6); 3.293(2.5); 3.271(1.3); 3.232(0.7); 3.195(3.8); 3.161(5.5); 3.124(0.5); 3.100(0.5); 3.071(0.6); 3.047(5.4); 3.013(3.5); 2.996(1.7); 2.968(0.4); 2.712(1.2); 2.676(2.7); 2.671(3.4); 2.542(299.5); 2.511(225.9); 2.507(450.3); 2.502(586.9); 2.498(425.5); 2.441(1.0); 2.368(1.6); 2.333(2.9); 2.329(3.8); 2.325(2.8); 2.291(0.8); 1.298(0.5); 1.258(0.7); 1.235(2.3); 0.855(0.3); 0.146(0.6); 0.008(4.4); 0.000(112.6); −0.008 (4.0); −0.149(0.6)
Example I-80: $^1$H-NMR(400.0 MHz, CD3CN):

δ = 12.038(0.5); 12.028(0.5); 8.391(1.5); 8.381(8.9); 8.367(0.3); 8.357(0.3); 8.332(0.5); 8.325(0.5); 8.269(0.7); 8.258(0.7); 8.227(0.6); 8.203(0.6); 8.180(1.5); 8.173(5.9); 8.168(1.7); 8.160(6.0); 8.118(0.5); 8.062(11.6); 8.057(8.2); 8.054(4.7); 8.028(0.9); 8.005(3.8); 7.986(11.9); 7.985(8.2); 7.963(0.7); 7.950(1.2); 7.930(1.5); 7.792(9.0); 7.609(3.1); 7.598(1.2); 7.589(4.8); 7.581(0.8); 7.525(2.1); 7.522(2.3); 7.500(16.0); 7.497(14.3); 7.486(2.1); 7.483(2.0); 7.416(0.5); 7.412(0.5); 7.398(2.9); 7.396(3.1); 7.379(4.4); 7.361(2.0); 7.359(1.9); 7.148(0.7); 7.132(4.9); 7.119(4.6); 4.839(4.1); 4.803(6.5); 4.699(6.7); 4.685(1.2); 4.664(5.9); 4.650(0.9); 4.288(0.4); 4.086(0.9); 4.068(2.6); 4.051(2.7); 4.033(0.9); 3.509(3.5); 3.474(6.7); 3.400(6.4); 3.365(3.4); 2.952(0.7); 2.890(3.8); 2.775(3.3); 2.191(9.4); 1.973(11.9); 1.965(1.2); 1.959(2.8); 1.954(13.7); 1.947(24.4); 1.941(32.2); 1.935(21.9); 1.929(11.2); 1.221(3.1); 1.203(6.1); 1.186(3.0); 0.146(0.5); 0.008(5.1); 0.000(101.6); −0.009(4.2); −0.150(0.5)
Example I-81: $^1$H-NMR(300.2 MHz, CDCl3):

δ = 8.902(11.3); 8.745(6.9); 8.728(7.4); 8.241(16.0); 7.989(15.0); 7.846(6.3); 7.829(6.2); 7.265(28.4); 4.843(7.1); 4.796(7.8); 4.591(8.2); 4.158(0.5); 4.134(1.7); 4.111(1.7); 4.087(0.6); 3.749(12.4); 3.702(12.7); 3.117(6.5); 3.068(5.7); 2.173(0.6); 2.047(7.5); 1.830(0.3); 1.705(1.5); 1.458(3.7); 1.284(2.0); 1.260(4.1); 1.236(2.0); 1.061(2.0); 1.042(2.8); 1.036(2.7); 1.025(2.8); 1.017(3.3); 1.006(3.3); 1.000(3.0); 0.980(3.1); 0.898(2.4); 0.878(2.5); 0.874(3.3); 0.862(3.4); 0.855(2.6); 0.843(3.1); 0.839(3.8); 0.820(2.7); 0.539(2.6); 0.519(3.6); 0.514(3.1); 0.504(2.6); 0.493(3.4); 0.483(3.3); 0.479(2.6); 0.458(2.7); 0.378(3.0); 0.355(3.8); 0.342(3.2); 0.334(2.8); 0.319(3.5); 0.298(2.0); 0.011(0.7); 0.000(21.2); −0.011(1.1)
Example I-82: $^1$H-NMR(400.1 MHz, DMSO):

δ = 8.417(15.8); 8.307(8.8); 8.294(9.2); 7.989(15.5); 7.618(8.5); 7.606(8.2); 5.378(16.0); 4.714(5.6); 4.678(6.7); 4.364(6.6); 4.327(5.5); 4.046(0.5); 4.028(0.5); 3.383(1.9); 3.366(0.8); 3.349(10.0); 3.336(10.1);

3.316(113.0); 3.301(2.5); 3.265(0.6); 2.677(0.3); 2.530(1.0); 2.517(20.4); 2.512(40.9); 2.508(54.7); 2.503(38.7); 2.499(18.2); 2.458(0.4); 2.335(0.3); 2.079(0.6); 1.995(2.1); 1.200(0.6); 1.182(1.1); 1.164(0.6); 0.879(1.1); 0.865(1.6); 0.856(2.5); 0.845(1.8); 0.839(2.3); 0.834(1.9); 0.820(1.8); 0.750(1.2); 0.735(1.1); 0.728(3.2); 0.712(2.1); 0.705(2.4); 0.691(1.9); 0.591(5.9); 0.570(6.9); 0.547(2.8); 0.545(2.9)

Example I-83: $^1$H-NMR(499.9 MHz, CDCl3):

δ = 8.289(4.4); 8.284(4.7); 8.269(7.7); 7.985(6.7); 7.895(4.4); 7.890(4.4); 7.265(5.9); 5.005(3.6); 4.977(3.9); 4.424(4.9); 4.421(4.8); 3.957(4.0); 3.929(3.9); 3.662(2.6); 3.659(2.5); 3.633(2.8); 3.630(2.7); 3.056(3.9); 3.027(3.6); 1.643(16.0); 0.948(1.0); 0.936(1.4); 0.933(1.3); 0.926(1.3); 0.921(1.6); 0.914(1.6); 0.911(1.4); 0.899(1.5); 0.850(1.2); 0.839(1.3); 0.836(1.5); 0.829(1.6); 0.825(1.3); 0.817(1.5); 0.815(1.7); 0.803(1.2); 0.522(1.2); 0.510(1.7); 0.507(1.5); 0.501(1.4); 0.495(1.6); 0.488(1.6); 0.486(1.3); 0.473(1.2); 0.353(1.3); 0.340(1.7); 0.339(1.7); 0.331(1.5); 0.326(1.4); 0.318(1.7); 0.317(1.6); 0.304(1.1); 0.000(0.8)

Example I-84: $^1$H-NMR(499.9 MHz, CDCl3):

δ = 8.285(6.1); 8.272(6.5); 7.943(5.6); 7.662(1.9); 7.645(2.2); 7.565(1.7); 7.551(2.2); 7.462(2.2); 7.446(2.5); 7.431(1.5); 7.258(6.9); 5.087(2.9); 5.059(3.1); 4.308(3.9); 4.306(4.0); 3.965(3.3); 3.936(3.1); 3.896(2.0); 3.893(2.0); 3.867(2.1); 3.864(2.2); 3.226(3.0); 3.197(2.7); 2.767(16.0); 1.589(6.0); 1.000(0.8); 0.988(1.1); 0.985(1.1); 0.978(1.1); 0.973(1.2); 0.966(1.2); 0.963(1.1); 0.951(1.1); 0.882(0.4); 0.865(0.9); 0.853(1.0); 0.850(1.2); 0.843(1.2); 0.839(1.0); 0.831(1.2); 0.829(1.3); 0.817(0.9); 0.525(1.0); 0.513(1.3); 0.510(1.2); 0.504(1.1); 0.498(1.3); 0.491(1.2); 0.489(1.1); 0.476(0.9); 0.364(1.0); 0.350(1.4); 0.342(1.2); 0.337(1.1); 0.329(1.3); 0.328(1.3); 0.316(0.8); 0.000(5.2)

Example I-85: $^1$H-NMR(400.0 MHz, DMSO):

δ = 8.428(16.0); 8.129(4.2); 8.116(4.2); 7.420(2.2); 7.408(3.8); 7.395(2.0); 7.344(1.5); 7.324(3.1); 7.304(2.8); 7.282(2.0); 7.268(1.1); 7.173(2.0); 7.146(3.2); 7.143(3.2); 7.124(4.4); 7.104(1.6); 5.370(2.3); 4.160(1.6); 4.125(4.3); 4.091(4.3); 4.056(1.6); 3.335(69.1); 2.997(0.5); 2.932(0.5); 2.878(2.3); 2.844(3.1); 2.825(2.1); 2.814(0.8); 2.790(3.3); 2.702(3.3); 2.666(5.2); 2.631(2.3); 2.543(76.4); 2.503(63.4); 2.368(0.4); 2.330(0.4); 1.234(0.4); 0.000(13.9)

Example I-86: $^1$H-NMR(400.0 MHz, DMSO):

δ = 8.327(4.0); 8.322(3.8); 8.194(16.0); 8.089(4.2); 8.077(4.1); 7.775(2.1); 7.769(2.0); 7.754(2.3); 7.748(2.1); 7.425(3.8); 7.404(3.4); 7.175(2.0); 7.163(3.6); 7.150(1.8); 6.302(4.5); 4.727(2.3); 4.691(3.2); 4.531(3.2); 4.495(2.3); 3.435(2.3); 3.400(2.8); 3.338(60.3); 3.156(2.7); 3.122(2.2); 2.997(0.3); 2.713(0.3); 2.543(74.6); 2.507(36.6); 2.504(42.5); 2.369(0.4); 1.234(0.4); 0.000(10.4)

Example I-87: $^1$H-NMR(400.0 MHz, DMSO):

δ = 8.379(16.0); 8.199(4.3); 8.187(4.4); 7.470(2.0); 7.458(3.7); 7.445(1.9); 5.654(3.8); 5.651(3.8); 4.493(1.8); 4.455(2.4); 4.235(2.7); 4.199(2.0); 3.334(112.6); 3.217(1.9); 3.183(2.5); 2.996(0.3); 2.979(2.4); 2.945(1.8); 2.672(0.4); 2.542(49.5); 2.507(43.6); 2.503(56.2); 2.499(42.7); 2.330(0.4); 1.235(0.3); 0.612(0.4); 0.597(0.6); 0.579(0.9); 0.565(0.8); 0.547(0.7); 0.533(0.9); 0.528(0.9); 0.519(1.0); 0.505(0.8); 0.488(0.8); 0.473(1.0); 0.454(0.7); 0.439(0.4); 0.425(0.4); 0.340(0.4); 0.322(0.5); 0.312(0.9); 0.297(1.1); 0.284(0.8); 0.280(0.8); 0.271(0.7); 0.254(0.4); 0.142(0.5); 0.124(0.7); 0.116(0.9); 0.099(1.1); 0.089(0.7); 0.084(0.7); 0.074(0.6); 0.008(0.6); 0.000(13.0)

Example I-88: $^1$H-NMR(400.0 MHz, DMSO):

δ = 8.402(16.0); 8.132(3.9); 8.120(4.1); 7.390(1.8); 7.377(3.3); 7.365(1.7); 7.318(0.8); 7.294(4.9); 7.281(6.4); 7.267(0.8); 7.261(0.7); 7.224(0.3); 7.203(2.2); 7.192(1.2); 7.186(1.5); 5.390(2.0); 4.151(1.8); 4.115(3.1); 4.033(3.1); 3.998(1.9); 3.335(104.7); 2.996(0.5); 2.828(1.7); 2.793(2.4); 2.773(1.4); 2.739(3.3); 2.712(0.6); 2.701(3.2); 2.666(1.9); 2.658(2.5); 2.624(1.7); 2.567(0.4); 2.543(75.5); 2.507(49.2); 2.503(65.0); 2.499(48.8); 2.368(0.4); 2.330(0.4); 1.234(0.5); 0.000(16.7); −0.008(0.8)

Example I-89: $^1$H-NMR(300.2 MHz, CDCl3):

δ = 8.273(16.0); 8.234(0.3); 8.213(12.0); 7.995(14.3); 7.270(13.1); 7.186(8.7); 7.178(8.9); 4.967(7.4); 4.920(8.1); 4.468(9.7); 4.463(10.1); 3.960(8.6); 3.913(7.9); 3.682(4.4); 3.636(5.2); 3.106(8.2); 3.060(7.1); 2.010(1.4); 1.704(6.8); 1.255(0.4); 0.986(1.9); 0.967(3.0); 0.961(2.6); 0.949(2.7); 0.941(3.5); 0.930(3.5); 0.924(3.0); 0.905(3.5); 0.873(2.6); 0.853(2.3); 0.849(3.4); 0.837(3.5); 0.830(2.5); 0.818(2.9); 0.813(4.0); 0.794(2.6); 0.542(2.8); 0.521(3.7); 0.516(3.1); 0.506(2.7); 0.496(3.5); 0.486(3.3); 0.481(2.5); 0.461(2.6); 0.378(3.1); 0.357(3.2); 0.354(3.7); 0.341(3.2); 0.334(2.8); 0.320(3.0); 0.317(3.3); 0.297(2.1); 0.071(1.4); 0.000(5.7)

Example I-90: $^1$H-NMR(400.0 MHz, CD3CN):

δ = 8.442(4.5); 8.259(2.6); 8.246(2.6); 8.008(4.2); 7.672(4.3); 7.517(2.4); 7.504(2.3); 4.324(2.0); 4.287(3.4); 4.184(3.3); 4.147(2.0); 4.068(0.7); 4.050(0.7); 4.009(0.6); 3.992(0.8); 3.988(1.7); 3.971(1.8); 3.967(1.2); 3.950(1.0); 3.921(1.0); 3.906(1.1); 3.899(1.7); 3.885(1.7); 3.878(0.7); 3.864(0.6); 3.194(2.2); 3.158(3.4); 3.026(2.7); 2.989(1.8); 2.157(3.6); 1.972(3.2); 1.965(0.3); 1.959(0.7); 1.953(3.6); 1.947(6.4); 1.940(8.7); 1.934(6.0); 1.928(3.4); 1.915(0.8); 1.909(0.7); 1.898(1.0); 1.895(0.8); 1.884(0.9); 1.878(0.9); 1.863(0.8); 1.677(0.8); 1.660(0.9); 1.655(0.9); 1.645(0.7); 1.639(0.8); 1.628(0.7); 1.624(0.7); 1.607(0.6); 1.221(0.9); 1.203(16.0); 1.186(0.9); 1.047(14.5); 0.008(0.6); 0.000(17.2); −0.009(0.6)

Example I-91: $^1$H-NMR(400.0 MHz, CD3CN):

δ = 8.483(5.5); 8.310(3.3); 8.297(3.4); 8.153(5.4); 7.739(5.4); 7.507(3.0); 7.494(2.9); 7.063(0.7); 7.055(0.5); 7.047(0.8); 7.039(4.7); 7.034(2.0); 7.028(5.1); 7.019(6.7); 7.015(6.3); 7.005(1.1); 7.000(0.5); 6.992(0.5); 4.697(2.8); 4.660(3.4); 4.366(5.4); 4.311(3.7); 4.274(3.1); 3.379(1.4); 3.343(4.0); 3.308(4.0); 3.273(1.4); 2.500(5.1); 2.138(66.4); 2.120(0.9); 2.113(0.9); 2.107(1.1); 2.101(0.8); 2.095(0.4); 1.964(4.9); 1.958(11.8); 1.952(64.0); 1.946(115.7); 1.940(154.7); 1.934(106.4); 1.927(55.2); 1.781(0.4); 1.774(0.7); 1.768(0.9); 1.762(0.6); 1.756(0.3); 1.422(1.7); 1.291(1.5); 1.233(15.5); 1.190(16.0); 0.146(1.3); 0.008(10.2); 0.000(285.3); −0.009(10.9); −0.150(1.3)

-continued

Example I-92: ¹H-NMR(400.1 MHz, CDCl3):

δ = 8.250(16.0); 8.205(4.4); 8.204(4.4); 8.184(4.7); 8.182(4.6); 8.050(4.4); 8.048(4.5); 8.029(5.1); 8.027(5.1); 7.964(13.7); 7.758(2.6); 7.755(2.7); 7.741(3.7); 7.737(5.2); 7.734(2.5); 7.719(3.0); 7.716(2.9); 7.626(3.4); 7.623(3.4); 7.609(3.0); 7.606(5.3); 7.602(3.3); 7.588(2.5); 7.585(2.4); 7.530(15.6); 7.275(5.4); 4.909(6.4); 4.873(6.9); 4.424(10.6); 4.125(0.4); 4.107(0.4); 3.990(7.4); 3.955(6.9); 3.777(4.1); 3.776(4.0); 3.742(5.1); 3.740(5.1); 3.489(6.8); 3.453(5.4); 2.038(1.8); 1.866(2.2); 1.302(0.3); 1.284(0.4); 1.272(1.1); 1.263(1.5); 1.255(1.6); 1.237(0.6); 0.897(0.7); 0.880(2.2); 0.862(0.9); 0.828(1.2); 0.813(2.7); 0.808(1.9); 0.801(1.6); 0.794(3.3); 0.786(5.5); 0.781(2.2); 0.768(4.5); 0.760(3.4); 0.754(3.1); 0.745(2.3); 0.742(3.5); 0.728(1.6); 0.486(2.3); 0.471(2.9); 0.467(2.4); 0.460(2.4); 0.451(2.7); 0.444(2.7); 0.440(2.1); 0.425(2.0); 0.292(2.4); 0.276(2.8); 0.274(3.1); 0.265(2.5); 0.259(2.5); 0.249(2.5); 0.247(2.7); 0.232(1.8); 0.077(0.4); 0.000(2.0)

Example I-93: ¹H-NMR(300.2 MHz, CDCl3):

δ = 9.040(3.3); 9.024(3.4); 8.160(5.2); 7.967(4.8); 7.705(2.9); 7.689(2.8); 7.266(9.8); 5.303(2.5); 4.647(2.4); 4.600(2.8); 4.189(3.4); 4.185(3.4); 3.971(2.8); 3.925(2.5); 3.317(1.4); 3.313(1.3); 3.270(1.9); 3.266(1.9); 3.058(2.8); 3.011(2.0); 2.047(0.4); 1.639(4.0); 1.233(16.0); 0.521(0.7); 0.516(0.7); 0.496(1.3); 0.475(0.8); 0.471(0.8); 0.452(0.3); 0.106(0.8); 0.087(2.0); 0.081(3.3); 0.070(1.6); 0.063(3.5); 0.058(2.1); 0.039(0.9); 0.000(6.9); −0.011(0.3); −0.111(0.4); −0.131(0.8); −0.137(1.0); −0.153(1.2); −0.157(1.3); −0.173(0.8); −0.181 (0.6)

Example I-94: 1H-NMR(400.0 MHz, CD3CN):

δ = 8.324(16.0); 8.293(5.0); 8.289(5.3); 8.282(5.3); 8.277(5.4); 7.929(15.1); 7.921(6.3); 7.907(5.8); 7.902(5.7); 7.323(6.0); 7.311(5.9); 7.304(5.8); 7.292(5.5); 4.935(9.1); 4.899(10.0); 4.193(14.4); 4.142(11.0); 4.106(10.1); 3.478(6.4); 3.442(8.5); 3.230(10.7); 3.194(8.1); 2.157(27.2); 2.108(0.4); 1.965(1.7); 1.959(4.1); 1.953(23.4); 1.947(42.8); 1.940(58.1); 1.934(40.9); 1.928(21.7); 1.769(0.4); 0.849(1.8); 0.834(3.5); 0.830(2.6); 0.822(2.4); 0.815(4.0); 0.807(4.3); 0.802(3.2); 0.798(5.6); 0.788(4.5); 0.783(2.6); 0.780(4.2); 0.772(4.0); 0.765(2.2); 0.757(2.8); 0.753(4.5); 0.739(2.5); 0.514(2.8); 0.499(4.6); 0.495(3.1); 0.488(2.5); 0.480(4.2); 0.473(4.4); 0.469(2.5); 0.456(5.2); 0.454(5.0); 0.441(3.3); 0.438(4.6); 0.429(4.0); 0.423(2.7); 0.414(2.9); 0.411(3.9); 0.396(2.0); 0.146(0.6); 0.008(4.2); 0.000(127.5); −0.009(7.0); −0.150(0.6)

Example I-95: 1H-NMR(400.0 MHz, CD3CN):

δ = 8.324(16.0); 8.294(5.1); 8.289(5.5); 8.282(5.5); 8.277(5.6); 7.929(15.8); 7.922(6.4); 7.907(5.8); 7.902(5.7); 7.323(6.0); 7.311(6.0); 7.304(5.9); 7.292(5.5); 4.936(9.5); 4.900(10.4); 4.189(13.1); 4.142(10.3); 4.106(9.5); 3.478(6.3); 3.443(8.4); 3.230(10.6); 3.194(8.0); 2.147(2.3); 2.120(0.5); 2.114(0.6); 2.108(0.7); 2.101(0.5); 1.964(3.1); 1.958(7.2); 1.952(41.8); 1.946(76.7); 1.940(104.5); 1.934(73.9); 1.928(39.5); 1.775(0.5); 1.769(0.6); 1.762(0.4); 0.849(1.9); 0.835(3.7); 0.830(2.7); 0.822(2.5); 0.815(4.2); 0.807(4.6); 0.803(3.4); 0.798(3.9); 0.788(4.7); 0.784(2.7); 0.780(4.5); 0.772(4.3); 0.766(2.3); 0.758(2.9); 0.754(4.8); 0.739(2.7); 0.514(2.8); 0.499(4.6); 0.495(3.1); 0.488(2.5); 0.480(4.2); 0.473(4.4); 0.468(2.5); 0.456(5.2); 0.454(4.7); 0.441(3.3); 0.438(4.6); 0.429(4.0); 0.423(2.7); 0.414(2.9); 0.411(3.9); 0.396(2.0); 0.146(1.2); 0.008(8.9); 0.000(263.7); −0.009(14.6); −0.150(1.2)

Example I-96: 1H-NMR(400.1 MHz, CDCl3):

δ = 8.286(16.0); 7.914(15.2); 7.696(10.2); 7.675(11.0); 7.262(27.6); 7.207(8.7); 7.186(7.9); 5.721(14.7); 4.662(2.2); 4.626(11.5); 4.610(13.7); 4.574(2.8); 3.751(8.4); 3.713(9.4); 3.060(7.9); 3.022(7.1); 1.595(11.7); 1.305(0.5); 1.287(0.7); 1.265(2.6); 0.909(0.6); 0.898(2.3); 0.893(2.5); 0.882(5.5); 0.872(4.6); 0.866(8.2); 0.852(6.5); 0.849(5.5); 0.838(4.1); 0.825(1.9); 0.822(1.5); 0.809(0.7); 0.788(0.7); 0.782(0.5); 0.761(0.5); 0.745(1.7); 0.740(1.0); 0.728(4.1); 0.717(9.0); 0.704(4.9); 0.699(5.6); 0.690(3.3); 0.678(1.2); 0.672(1.7); 0.657(0.4); 0.008(0.7); 0.000(20.3); −0.009(0.7)

Example I-97: 1H-NMR(400.1 MHz, CDCl3):

δ = 8.311(12.2); 8.306(12.2); 8.276(15.7); 7.905(16.0); 7.784(12.8); 7.779(12.4); 7.264(23.8); 6.141(9.0); 4.637(3.5); 4.601(13.4); 4.578(14.8); 4.542(3.9); 4.130(0.6); 4.112(0.6); 3.759(10.1); 3.720(11.2); 3.050(10.3); 3.012(9.3); 2.042(2.6); 2.003(11.3); 1.276(0.8); 1.258(1.9); 1.240(0.8); 0.871(1.5); 0.865(1.9); 0.859(2.0); 0.850(3.9); 0.845(2.7); 0.833(3.7); 0.823(4.9); 0.800(3.4); 0.791(3.6); 0.787(4.4); 0.775(4.7); 0.760(2.8); 0.755(4.6); 0.748(4.7); 0.742(2.8); 0.734(1.6); 0.726(4.2); 0.716(4.3); 0.712(3.8); 0.703(3.8); 0.686(5.4); 0.676(4.0); 0.664(3.1); 0.661(4.1); 0.650(2.3); 0.644(2.1); 0.639(1.7); 0.616(0.3); 0.070(2.2); 0.008(0.3); 0.000(10.4); −0.009(0.4)

1H-NMR Data for Compounds in Table 2 Written in Classical Form

| Ex-no | NMR |
| --- | --- |
| V-2 | 1H-NMR (400 MHz, d3-CD3CN): δ = 8.44-843 (dd, 1H), 7.79-7.77 (dd, 1H), 7.29-7.26 (dd, 1H), 4.41 (s, 2H), 1.72-1.68 (m, 2H), 1.49-1.46 (m, 2H) ppm |
| V-3 | 1H-NMR (400 MHz, d3-CD3CN): δ = 8.30-8.28 (dd, 1H), 7.65-7.63 (dd, 1H), 7.33-7.30 (dd, 1H), 4.27 (s, 2H), 1.72-1.64 (m, 2H), 1.49-1.46 (m, 2H) ppm |
| V-4 | 1H-NMR (400 MHz, d3-CD3CN): δ = 8.55 (s, 1H), 8.43 (d, 1H), 7.25 (d, 1H), 4.30 (s, 2H), 1.71-1.64 (m, 2H), 1.50-1.47 (m, 2H) ppm |
| V-6 | 1H-NMR (400 MHz, d3-CD3CN): δ = 8.17 (d, 1H), 7.58-7.56 (dd, 1H), 7.35 (d, 1H), 4.17 (s, 2H), 1.69-1.61 (m, 2H), 1.47-1.43 (m, 2H) ppm |
| V-7 | 1H-NMR (400 MHz, d3-CD3CN): δ = 8.56 (s, 1H), 8.44 (d, 1H), 7.28 (d, 1H), 4.27 (d, 2H), 1.54-1.36 (m, 4H) ppm |
| V-8 | 1H-NMR (400 MHz, d3-CD3CN): δ = 8.56 (s, 1H), 8.44 (d, 1H), 7.26 (d, 1H), 4.20 (d, 2H), 1.53 (d, 6H, J = 22 Hz) ppm |

-continued

| Ex-no | NMR |
|---|---|
| V-9 | 1H-NMR (400 MHz, d3-CD3CN): δ = 8.27-8.26 (dd, 1H), 7.60-7.58 (dd, 1H), 7.30-7.27 (m, 1H), 3.91 (s, 2H), 1.40 (s, 3H), 1.29 (m, 2H), 0.84-0.81 (m, 2H) ppm |
| V-10 | 1H-NMR (400 MHz, d3-CD3CN): δ = 8.24-8.22 (dd, 1H), 7.52-7.50 (m, 3H), 7.43-7.40 (m, 3H), 7.26-7.23 (m, 1H), 3.72 (s, 2H), 1.60-1.58 (m, 2H), 1.27-1.24 (m, 2H) ppm |
| V-11 | 1H-NMR (400 MHz, d3-CD3CN): δ = 8.52 (s, 1H), 8.39 (d, 1H), 7.19 (d, 1H), 3.94 (s, 2H), 1.40 (s, 3H), 1.30-1.27 (m, 2H), 0.85-0.82 (m, 2H) ppm |
| V-12 | 1H-NMR (400 MHz, d3-CD3CN): δ = 8.53 (s, 1H), 8.40 (d, 1H), 7.20 (d, 1H), 4.05 (s, 2H), 2.04-1.99 (m, 2H), 1.60-1.50 (m, 2H), 1.50-1.36 (m, 6H), 1.21 (s, 3H) ppm |

NMR-Peak Lists for Compounds in Table 2

Example V-1: 1H-NMR(499.9 MHz, CDCl3):

δ = 14.874(1.3); 8.194(0.7); 8.177(0.8); 8.072(0.6); 8.055(0.7); 7.820(0.6); 7.803(0.7); 7.739(0.4); 7.724(0.6); 7.722(0.6); 7.707(0.4); 7.705(0.4); 7.701(0.3); 7.608(1.4); 7.599(7.1); 7.591(1.5); 7.581(7.2); 7.563(0.5); 7.548(0.7); 7.533(0.4); 7.496(3.5); 7.486(6.1); 7.481(7.2); 7.471(6.2); 7.467(4.9); 7.325(6.6); 7.308(5.1); 7.262(2.7); 7.233(3.6); 7.217(6.0); 7.203(2.8); 6.775(6.1); 6.756(5.8); 6.138(16.0); 4.833(3.7); 4.568(0.5); 4.224(1.3); 4.212(2.3); 4.200(1.1); 4.182(0.7); 4.169(1.0); 4.156(0.5); 3.575(1.3); 3.563(2.3); 3.560(1.5); 3.551(1.3); 3.546(0.7); 3.441(1.2); 3.428(2.2); 3.415(1.1); 1.908(0.4); 1.905(0.4); 1.899(0.5); 1.891(0.8); 1.887(0.7); 1.879(1.1); 1.873(1.0); 1.866(1.4); 1.862(1.4); 1.853(1.4); 1.849(1.3); 1.841(0.9); 1.836(0.9); 1.823(0.4); 1.766(0.6); 1.759(0.6); 1.751(0.6); 1.739(1.0); 1.729(1.3); 1.719(3.2); 1.712(3.6); 1.706(6.1); 1.696(14.1); 1.690(14.0); 1.681(5.5); 1.662(0.6); 1.648(1.0); 1.640(1.2); 1.634(1.3); 1.624(0.5); 1.514(0.8); 1.505(2.1); 1.498(2.4); 1.490(1.0); 1.419(1.0); 1.410(2.4); 1.403(2.1); 1.393(1.0); 1.369(1.3); 1.361(3.2); 1.355(2.8); 1.345(1.3); 1.339(0.6); 1.305(5.5); 1.296(13.6); 1.290(13.3); 1.280(4.6); 1.247(0.4); 0.000(2.2)

Example V-5: 1H-NMR(300.2 MHz, CDCl3):

δ = 7.756(0.3); 7.733(0.4); 7.728(0.3); 7.712(0.4); 7.689(0.4); 7.684(0.3); 7.475(0.4); 7.465(0.4); 7.451(0.4); 7.441(0.4); 7.262(14.8); 7.163(0.5); 7.124(16.2); 4.204(16.0); 1.741(2.5); 1.724(6.3); 1.712(7.3); 1.697(3.4); 1.641(0.7); 1.553(11.7); 1.534(0.6); 1.479(3.4); 1.464(7.1); 1.452(6.2); 1.434(2.5); 0.069(0.5); 0.011(0.5); 0.000(12.5); −0.011(0.5)

Example V-13: 1H-NMR(499.9 MHz, CDCl3):

δ = 8.762(4.4); 8.758(4.2); 8.109(2.7); 8.092(2.9); 7.998(3.7); 7.995(3.6); 7.798(2.5); 7.782(2.8); 7.715(1.6); 7.712(1.5); 7.701(2.1); 7.698(2.9); 7.695(1.5); 7.684(1.8); 7.558(2.0); 7.556(1.8); 7.542(3.1); 7.528(1.5); 7.526(1.3); 7.258(44.3); 4.394(16.0); 1.731(2.8); 1.720(8.3); 1.713(8.4); 1.704(3.4); 1.671(0.3); 1.561(23.3); 1.471(0.4); 1.437(3.3); 1.428(8.3); 1.421(8.3); 1.411(2.8); 1.256(0.8); 0.069(1.7); 0.006(1.2); 0.000(29.0); −0.007(1.1)

Example V-15: 1H-NMR(400.0 MHz, CD3CN):

δ = 8.320(2.0); 8.315(2.0); 8.308(2.0); 8.303(2.0); 7.641(2.0); 7.637(2.0); 7.623(2.3); 7.618(2.2); 7.338(2.4); 7.326(2.4); 7.319(2.2); 7.307(2.1); 5.447(1.9); 4.899(16.0); 4.783(16.0); 4.178(13.9); 2.143(19.3); 1.972(0.5); 1.964(0.8); 1.958(1.3); 1.952(5.6); 1.946(9.9); 1.940(12.9); 1.934(8.8); 1.927(4.6); 0.008(0.3); 0.000(8.7); −0.008(0.4)

Example V-16: 1H-NMR(400.0 MHz, DMSO):

δ = .148(2.0); 8.145(1.6); 8.137(2.0); 7.868(1.1); 7.863(1.2); 7.850(1.3); 7.844(2.0); 7.839(1.2); 7.825(1.3); 7.820(1.2); 7.340(1.5); 7.335(1.6); 7.328(1.5); 7.322(2.7); 7.317(1.5); 7.310(1.5); 7.304(1.4); 4.186(16.0); 3.319(14.7); 2.675(0.5); 2.671(0.7); 2.666(0.5); 2.524(1.5); 2.510(37.7); 2.506(77.7); 2.501(103.0); 2.497(73.5); 2.492(34.9); 2.333(0.5); 2.328(0.7); 2.324(0.5); 2.231(0.4); 1.764(2.8); 1.751(7.0); 1.742(6.9); 1.730(3.7); 1.688(0.4); 1.596(0.5); 1.554(3.8); 1.541(6.8); 1.533(6.9); 1.519(2.8); 0.146(0.3); 0.008(2.9); 0.000(81.4); −0.009(2.6); −0.150(0.4)

Example V-17: 1H-NMR(400.1 MHz, DMSO):

δ = 7.902(4.6); 7.882(5.1); 7.593(5.7); 7.573(5.0); 4.296(16.0); 3.308(3.3); 2.517(4.9); 2.512(9.7); 2.508(13.1); 2.503(9.2); 2.499(4.3); 1.774(2.4); 1.760(5.8); 1.752(5.9); 1.739(3.2); 1.698(0.4); 1.619(0.4); 1.577(3.2); 1.564(5.8); 1.556(5.8); 1.542(2.3)

Example V-18: 1H-NMR(400.1 MHz, DMSO):

δ = 8.345(0.5); 8.332(6.2); 7.818(1.8); 7.798(2.2); 7.681(1.6); 7.663(2.2); 7.573(2.4); 7.553(2.5); 7.535(1.5); 4.421(11.1); 4.156(1.7); 4.141(3.2); 4.126(1.4); 3.693(1.4); 3.677(3.3); 3.671(0.5); 3.661(1.7); 3.319(12.6); 3.290(0.6); 2.714(0.4); 2.667(16.0); 2.531(0.4); 2.517(8.3); 2.513(17.0); 2.508(23.1); 2.504(16.6); 2.499(7.9); 1.995(0.4); 1.817(1.8); 1.803(4.8); 1.795(4.8); 1.783(3.0); 1.775(1.0); 1.765(1.2); 1.763(1.2); 1.759(0.8); 1.752(1.1); 1.741(1.4); 1.729(0.9); 1.723(1.0); 1.720(0.7); 1.714(0.7); 1.707(0.6); 1.624(1.0); 1.610(2.3); 1.606(3.0); 1.603(2.9); 1.593(4.7); 1.585(4.6); 1.571(1.7); 1.456(1.4); 1.443(2.3); 1.435(2.1); 1.421(1.0)

Example V-19: 1H-NMR(400.1 MHz, DMSO):

δ = 8.462(2.4); 8.459(2.5); 8.450(2.5); 8.447(2.5); 8.403(3.6); 8.399(3.6); 7.627(1.3); 7.623(2.1); 7.618(1.3); 7.608(1.5); 7.603(2.4); 7.599(1.5); 7.360(2.1); 7.348(2.1); 7.340(1.9); 7.328(1.8); 4.141(16.0); 3.336(1.3); 2.512(9.7); 2.508(12.9); 2.504(9.4); 1.775(2.4); 1.761(6.7); 1.753(6.7); 1.741(3.2); 1.699(0.4); 1.572(0.4); 1.530(3.1); 1.517(6.4); 1.509(6.7); 1.495(2.4)

Example V-20: 1H-NMR(400.1 MHz, DMSO):

δ = 8.351(4.5); 8.337(4.6); 7.665(4.7); 7.652(4.5); 4.415(16.0); 3.318(11.9); 2.517(4.5); 2.513(8.8); 2.508(11.8); 2.504(8.4); 2.499(4.0); 1.808(2.1); 1.794(5.3); 1.786(5.5); 1.773(2.9); 1.732(0.4); 1.661(0.3); 1.619(2.9); 1.607(5.4); 1.599(5.3); 1.585(2.0)

Example V-21: 1H-NMR(400.1 MHz, DMSO):

δ = 8.449(4.4); 8.443(4.5); 8.034(4.9); 8.027(4.7); 5.221(0.5); 4.298(16.0); 3.317(21.6); 3.028(0.4); 2.531(0.3); 2.517(7.7); 2.513(15.5); 2.508(20.9); 2.504(15.1); 2.500(7.3); 1.774(2.2); 1.760(5.8); 1.752(6.1); 1.740(3.2); 1.698(0.6); 1.626(0.4); 1.585(3.1); 1.572(5.9); 1.564(5.8); 1.550(2.2)

1H-NMR Data for Compounds in Table 3 Written in Classical Form

| Ex-no | NMR |
|---|---|
| XII-2 | 1H-NMR (400 MHz, d3-CD3CN): δ = 8.26 (d, 1H), 7.67-7.64 (dd, 1H), 7.34-7.32 (d, 1H), 3.37 (d, 1H), 3.13 (d, 1H), 2.72 (d, 1H), 2.56 (d, 1H), 0.95-0.90 (m, 1H), 0.80-0.70 (m, 2H), 0.70-0.60 (m, 1H) ppm |
| XII-3 | 1H-NMR (400 MHz, d3-CD3CN): δ = 8.52 (s, 1H), 8.37 (d, 1H), 7.29 (d, 1H), 3.54 (d, 1H), 3.42 (d, 1H), 2.69 (d, 1H), 2.41 (d, 1H), 1.05-0.85 (m, 4H) ppm |
| XII-5 | 1H-NMR (400 MHz, d3-CD3CN): δ = 8.32-8.30 (dd, 1H), 7.79-7.74 (dd, 1H), 7.38-7.36 (dd, 1H), 3.50 (d, 1H), 3.35 (d, 1H), 2.73 (d, 1H), 2.33 (d, 1H), 1.10-1.00 (m, 2H), 0.95-0.85 (m, 2H) ppm |

NMR-Peak Lists for Compounds in Table 3

Example XII-1: $^1$H-NMR(400.1 MHz, DMSO):

δ = 8.298(9.1); 8.277(9.6); 8.009(0.5); 7.996(6.5); 7.975(8.1); 7.966(6.6); 7.964(6.8); 7.946(6.9); 7.943(7.1); 7.764(4.0); 7.760(4.1); 7.746(5.3); 7.743(7.7); 7.739(4.1); 7.725(4.4); 7.722(4.2); 7.599(4.8); 7.596(4.9); 7.582(4.9); 7.579(7.9); 7.576(5.2); 7.561(3.8); 7.559(3.7); 7.542(0.7); 7.521(0.6); 7.493(13.5); 7.472(13.0); 7.140(0.3); 3.616(4.9); 3.581(15.5); 3.551(16.0); 3.516(5.2); 3.319(6.6); 3.210(0.4); 3.178(0.4); 2.799(9.1); 2.787(12.4); 2.725(13.1); 2.713(10.2); 2.686(0.4); 2.682(0.5); 2.677(0.6); 2.673(0.4); 2.663(0.7); 2.530(1.5); 2.517(19.4); 2.512(39.4); 2.508(53.8); 2.503(39.6); 2.499(20.3); 2.463(1.4); 2.339(0.3); 2.335(0.4); 2.330(0.3); 1.290(1.8); 0.968(1.2); 0.954(2.5); 0.947(1.9); 0.941(2.1); 0.934(3.1); 0.928(4.6); 0.923(6.2); 0.911(5.2); 0.906(5.3); 0.897(4.9); 0.880(6.7); 0.871(9.1); 0.869(9.2); 0.861(6.7); 0.846(4.5); 0.841(2.6); 0.835(4.9); 0.828(5.7); 0.818(6.3); 0.811(5.2); 0.804(3.6); 0.798(2.8); 0.794(2.5); 0.785(3.1); 0.772(1.6)

Example XII-20: $^1$H-NMR(400.1 MHz, DMSO):

δ = 8.321(16.0); 7.256(12.5); 7.251(12.6); 3.584(8.9); 3.549(14.0); 3.435(12.5); 3.400(7.9); 3.315(43.4); 2.764(11.3); 2.754(12.3); 2.678(0.4); 2.673(0.3); 2.531(1.1); 2.517(24.9); 2.513(51.7); 2.509(71.0); 2.504(52.4); 2.491(14.7); 2.480(13.1); 2.463(0.5); 2.340(0.4); 2.335(0.5); 2.331(0.3); 1.106(0.6); 1.091(3.9); 1.081(5.0); 1.066(8.3); 1.063(8.4); 1.056(7.1); 1.043(7.6); 1.038(8.5); 1.024(2.3); 0.968(3.5); 0.955(6.5); 0.937(11.2); 0.930(5.8); 0.924(4.4); 0.913(8.6); 0.902(2.2); 0.898(2.7); 0.891(4.1); 0.877(1.5)

Example XII-23: $^1$H-NMR(400.0 MHz, CD3CN):

δ = 8.284(7.1); 8.279(7.4); 8.272(7.3); 8.267(7.3); 7.729(7.4); 7.724(7.3); 7.710(8.1); 7.705(7.8); 7.293(9.2); 7.281(9.1); 7.274(8.5); 7.262(8.2); 3.467(7.7); 3.430(15.2); 3.359(16.0); 3.322(8.1); 2.686(13.0); 2.675(14.1); 2.470(9.0); 2.465(9.3); 2.459(8.3); 2.454(8.2); 2.152(6.8); 1.965(0.7); 1.959(1.8); 1.953(9.7); 1.947(17.4); 1.941(23.3); 1.935(15.9); 1.928(8.1); 1.207(0.3); 1.054(1.3); 1.039(1.4); 1.036(1.5); 1.030(0.9); 1.022(2.8); 1.010(3.3); 1.006(4.4); 0.994(4.0); 0.988(1.6); 0.980(1.5); 0.976(4.4); 0.973(3.0); 0.965(4.6); 0.962(7.2); 0.958(3.7); 0.950(3.8); 0.945(3.9); 0.935(1.8); 0.932(2.1); 0.927(4.1); 0.916(4.5); 0.912(4.3); 0.901(3.1); 0.895(1.4); 0.886(1.6); 0.883(2.0); 0.869(2.4); 0.753(2.4); 0.738(2.1); 0.735(2.0); 0.728(2.7); 0.725(3.5); 0.714(2.6); 0.710(5.0); 0.707(4.4); 0.701(3.2); 0.695(4.6); 0.686(4.2); 0.683(4.2); 0.671(7.8); 0.659(3.9); 0.655(4.0); 0.648(4.9); 0.641(3.2); 0.636(4.0); 0.631(5.1); 0.626(2.7); 0.617(2.6); 0.612(2.0); 0.608(2.0); 0.604(1.8); 0.590(1.8); 0.008(2.0); 0.000(49.3); −0.009(1.7)

Example XII-24: $^1$H-NMR(400.1 MHz, CDCl3):

δ = 7.315(0.8); 7.296(49.5); 7.265(9.5); 7.250(0.8); 7.236(0.6); 7.232(0.6); 7.093(0.4); 5.581(0.4); 5.377(0.4); 4.037(12.0); 4.008(16.0); 3.849(16.0); 3.820(12.0); 3.740(0.4); 3.732(0.4); 3.723(0.4); 3.720(0.4); 3.708(0.3); 3.195(8.3); 3.161(13.7); 3.109(0.7); 3.064(12.4); 3.030(7.5); 2.924(0.4); 2.366(13.5); 2.349(1.0); 1.788(0.3); 1.697(0.5); 1.688(0.5); 1.607(2.1); 1.520(0.5); 1.518(0.6); 1.512(0.5); 1.431(0.5); 1.210(0.7); 1.208(0.7); 1.204(0.5); 1.147(2.7); 1.141(0.5); 1.131(3.4); 1.124(6.1); 1.111(3.6); 1.106(4.4); 1.101(3.8); 1.093(0.6); 1.086(4.0); 0.977(3.0); 0.962(2.6); 0.955(6.4); 0.941(3.2); 0.938(4.0); 0.932(4.5); 0.924(0.6); 0.917(3.7); 0.751(12.5); 0.745(1.9); 0.729(15.5); 0.727(14.8); 0.711(1.6); 0.705(7.8); 0.071(1.4); 0.000(5.6)

Example XII-25: $^1$H-NMR(400.0 MHz, DMSO):

δ = 9.110(10.8); 9.106(10.5); 8.719(12.2); 8.706(12.4); 8.693(0.3); 7.481(7.8); 7.477(7.7); 7.468(7.6); 7.464(7.3); 3.411(5.8); 3.377(14.3); 3.332(15.9); 3.322(14.4); 3.297(6.3); 2.801(8.6); 2.789(13.5); 2.753(14.8); 2.741(9.4); 2.672(0.4); 2.525(0.8); 2.512(21.0); 2.507(42.5); 2.503(55.5); 2.498(39.1); 2.494(18.1); 2.330(0.4); 2.288(1.0); 1.909(0.5); 1.292(0.5); 1.235(0.4); 0.989(0.3); 0.984(0.3); 0.966(1.6); 0.953(3.3); 0.939(3.5); 0.934(3.3); 0.926(4.6); 0.921(4.0); 0.917(2.5); 0.906(3.2); 0.902(3.8); 0.889(5.2);

0.879(4.5); 0.875(4.4); 0.863(8.8); 0.859(16.0); 0.843(4.4); 0.840(4.5); 0.830(4.5); 0.827(1.2); 0.814(2.7); 0.803(3.7); 0.787(3.0); 0.784(4.9); 0.778(5.0); 0.771(4.1); 0.766(4.1); 0.752(4.3); 0.739(2.0); 0.000(1.1)

Example XII-29: $^1$H-NMR(400.0 MHz, DMSO):

δ = 8.885(8.7); 8.851(1.1); 5.458(0.3); 4.910(16.0); 4.558(2.7); 3.943(1.2); 3.913(1.6); 3.742(1.4); 3.711(1.1); 3.321(18.2); 3.287(2.3); 3.286(2.2); 3.271(6.1); 3.255(5.0); 3.181(0.5); 3.174(4.8); 3.158(5.7); 3.142(2.2); 2.622(6.3); 2.525(0.4); 2.520(0.7); 2.512(12.6); 2.507(26.1); 2.503(34.7); 2.498(24.9); 2.494(11.8); 1.890(0.3); 1.884(0.4); 1.877(0.4); 1.873(0.4); 1.863(0.4); 1.851(0.4); 1.744(1.8); 1.730(4.0); 1.721(3.8); 1.709(2.4); 1.702(0.5); 1.689(0.6); 1.685(0.4); 1.678(3.0); 1.664(5.0); 1.656(6.8); 1.644(3.7); 1.638(0.6); 1.630(0.6); 1.617(0.4); 1.602(0.5); 1.578(0.5); 1.574(0.7); 1.566(0.5); 1.556(0.4); 1.554(0.4); 1.545(0.4); 1.541(0.4); 1.532(2.4); 1.525(0.7); 1.519(3.9); 1.511(4.0); 1.497(1.6); 1.484(3.7); 1.472(6.5); 1.463(6.4); 1.450(2.7); 1.322(0.3); 1.303(0.4); 1.294(0.5); 1.291(0.4); 1.275(0.4); 1.233(0.5); 1.229(0.6); 1.216(0.4); 1.208(0.5); 1.192(0.4); 1.113(0.7); 1.105(0.7); 1.094(0.6); 1.089(0.7); 1.084(0.7); 1.078(0.5); 1.069(0.5); 1.057(0.4); 0.008(0.6); 0.000(21.0); −0.009(0.7)

Example XII-30: $^1$H-NMR(300.2 MHz, CDCl3):

δ = 7.746(0.5); 7.719(0.5); 7.588(9.2); 7.562(10.6); 7.288(0.4); 7.265(12.4); 7.226(11.3); 7.200(9.8); 3.576(7.0); 3.527(11.8); 3.387(9.7); 3.338(5.8); 3.013(0.3); 2.997(0.4); 2.713(8.5); 2.698(9.3); 2.383(9.5); 2.368(8.8); 1.575(12.9); 1.485(0.5); 1.462(0.6); 1.453(0.8); 1.430(0.7); 1.176(1.3); 1.152(1.3); 1.113(1.1); 1.105(3.5); 1.082(3.5); 1.070(4.5); 1.065(3.7); 1.038(1.6); 1.002(0.6); 0.993(0.9); 0.973(1.7); 0.961(2.0); 0.949(4.6); 0.941(4.8); 0.931(12.5); 0.926(16.0); 0.918(5.2); 0.914(6.7); 0.901(8.3); 0.897(10.1); 0.886(2.9); 0.880(2.1); 0.862(4.6); 0.851(2.8); 0.824(0.5); 0.816(0.4); 0.796(0.4); 0.070(2.8); 0.000(7.4)

Example XII-31: $^1$H-NMR(400.0 MHz, DMSO):

δ = 8.316(0.3); 8.142(5.6); 8.139(4.7); 8.134(4.6); 8.130(5.5); 8.127(4.2); 7.881(3.4); 7.877(3.3); 7.863(3.9); 7.857(5.7); 7.852(3.4); 7.838(3.6); 7.833(3.3); 7.318(4.4); 7.313(4.5); 7.307(4.0); 7.301(7.0); 7.295(4.2); 7.288(3.9); 7.283(3.8); 3.485(0.5); 3.324(113.3); 3.281(19.8); 3.274(18.7); 3.237(1.8); 2.755(12.6); 2.744(13.6); 2.676(0.7); 2.671(0.9); 2.667(0.7); 2.558(1.0); 2.541(13.8); 2.530(13.0); 2.511(46.9); 2.507(91.6); 2.502(118.9); 2.498(84.8); 2.493(40.0); 2.333(0.6); 2.329(0.8); 2.324(0.6); 2.320(0.4); 1.260(0.3); 1.249(0.3); 1.234(0.7); 1.213(0.3); 1.206(0.3); 1.200(0.3); 1.189(0.3); 1.180(0.3); 1.169(0.4); 1.161(0.4); 1.152(0.4); 1.143(0.4); 1.025(0.5); 1.006(2.0); 0.997(3.0); 0.983(5.5); 0.979(4.3); 0.976(4.0); 0.966(4.7); 0.957(1.5); 0.946(2.8); 0.904(2.4); 0.896(3.5); 0.887(5.4); 0.880(10.3); 0.876(9.2); 0.863(16.0); 0.859(8.8); 0.854(6.8); 0.844(5.1); 0.837(7.5); 0.825(2.1); 0.817(6.9); 0.808(5.0); 0.799(5.9); 0.784(3.0); 0.775(1.7); 0.758(0.3); 0.008(2.0); 0.000(47.5); −0.009(1.6)

Example XII-35: $^1$H-NMR(400.0 MHz, DMSO):

δ = 8.604(15.7); 8.562(3.1); 8.507(4.3); 8.422(2.1); 8.409(2.5); 8.355(2.0); 8.342(2.1); 8.321(4.7); 8.316(3.8); 8.296(8.5); 8.283(8.4); 7.961(4.3); 7.850(1.0); 7.813(0.8); 7.743(2.3); 7.725(2.7); 7.645(2.1); 7.633(2.0); 7.625(1.0); 7.540(0.7); 7.443(13.0); 7.421(0.8); 7.388(0.7); 7.376(1.5); 7.356(7.4); 7.337(12.7); 7.317(7.9); 7.304(1.3); 7.286(1.5); 7.266(1.0); 7.240(0.9); 7.225(4.5); 7.207(5.9); 7.188(2.2); 7.145(8.9); 7.133(16.0); 7.116(9.3); 7.092(1.8); 7.079(1.7); 7.059(8.7); 7.037(0.8); 7.015(0.7); 5.390(3.0); 5.376(6.7); 5.362(3.0); 5.051(3.4); 4.790(0.8); 4.475(1.2); 4.441(1.6); 4.188(7.9); 4.183(8.3); 4.174(8.1); 4.169(7.5); 3.932(1.7); 3.897(1.6); 3.717(4.1); 3.702(0.8); 3.597(0.7); 3.495(0.9); 3.466(1.1); 3.455(1.2); 3.418(1.4); 3.403(1.8); 3.385(2.9); 3.364(6.2); 3.334(3090.6); 3.311(10.1); 3.301(3.1); 3.293(2.9); 3.271(1.4); 3.261(1.3); 3.237(1.0); 3.193(0.8); 3.184(0.9); 3.076(1.6); 3.037(5.0); 2.711(2.0); 2.671(9.4); 2.667(7.0); 2.620(0.8); 2.581(2.2); 2.571(2.4); 2.559(3.8); 2.542(460.9); 2.511(584.8); 2.507(1170.5); 2.502(1524.3); 2.498(1095.2); 2.367(2.2); 2.350(0.8); 2.333(7.0); 2.329(9.6); 2.325(6.6); 2.291(0.9); 1.463(0.8); 1.298(1.2); 1.259(1.8); 1.235(5.5); 1.218(0.7); 1.143(4.1); 1.131(11.4); 1.127(11.5); 1.115(4.1); 0.848(4.4); 0.837(11.3); 0.831(11.4); 0.820(3.7); 0.517(0.9); 0.507(0.8); 0.391(0.9); 0.383(0.8); 0.358(0.7); 0.340(0.8); 0.334(0.9); 0.146(1.0); 0.008(6.7); 0.000(197.0); −0.008(6.9); −0.150(1.0); −3.238(0.8)

Example XII-38: $^1$H-NMR(499.9 MHz, CDCl3):

δ = 8.859(14.7); 8.672(9.2); 8.662(9.3); 7.315(8.3); 7.305(8.3); 7.261(14.5); 6.564(0.5); 3.739(6.2); 3.709(7.3); 3.383(7.2); 3.353(6.1); 2.655(9.9); 2.646(10.4); 2.209(10.2); 2.200(10.1); 2.056(0.4); 2.049(0.5); 1.658(0.6); 1.650(1.2); 1.642(1.7); 1.624(4.7); 1.510(0.4); 1.498(0.6); 1.494(0.6); 1.483(0.4); 1.382(0.3); 1.353(0.5); 1.351(0.4); 1.349(0.4); 1.161(1.2); 1.146(0.5); 1.123(2.2); 1.117(3.4); 1.115(3.6); 1.109(3.2); 1.094(4.8); 1.069(1.2); 1.018(1.4); 1.015(1.7); 1.009(0.6); 0.997(6.2); 0.991(13.7); 0.988(16.0); 0.984(10.2); 0.970(0.8); 0.963(2.4); 0.961(2.2); 0.947(1.9); 0.923(5.1); 0.918(4.4); 0.917(4.0); 0.907(3.2); 0.901(3.4); 0.897(3.3); 0.892(2.4); 0.006(0.4); 0.000(10.0)

Example XII-39: $^1$H-NMR(400.1 MHz, DMSO):

δ = 8.656(0.7); 8.342(0.5); 8.318(6.8); 8.205(0.5); 7.826(1.8); 7.807(2.0); 7.676(0.3); 7.674(0.3); 7.658(1.4); 7.655(1.7); 7.653(1.2); 7.641(1.8); 7.638(2.3); 7.548(2.7); 7.530(2.5); 7.528(2.6); 7.510(1.7); 7.360(1.5); 4.305(0.4); 4.151(2.9); 4.136(5.6); 4.120(2.5); 3.716(2.8); 3.696(0.4); 3.687(2.3); 3.679(4.1); 3.672(6.2); 3.656(3.1); 3.517(3.1); 3.481(2.2); 3.311(14.9); 3.286(0.5); 2.750(3.1); 2.740(3.2); 2.677(1.6); 2.654(16.0); 2.512(1.9); 2.507(4.0); 2.503(5.5); 2.498(3.9); 2.494(2.1); 2.373(3.7); 2.362(3.6); 1.798(0.7); 1.796(0.7); 1.792(0.9); 1.786(0.8); 1.779(1.1); 1.776(1.6); 1.770(1.4); 1.760(1.9); 1.758(1.8); 1.753(1.1); 1.747(1.7); 1.740(1.2); 1.736(1.8); 1.734(2.0); 1.724(1.7); 1.718(1.9); 1.715(1.5); 1.709(1.0); 1.702(1.4); 1.695(0.7); 1.685(1.9); 1.619(1.9); 1.605(3.6); 1.597(3.9); 1.585(2.7); 1.543(0.5); 1.539(0.5); 1.532(0.5); 1.519(0.4); 1.511(0.9); 1.494(1.0); 1.482(0.5); 1.475(0.4); 1.450(2.7); 1.438(4.0); 1.429(3.7); 1.419(0.5); 1.416(1.9); 1.402(0.3); 1.128(0.6); 1.121(1.8); 1.117(1.5); 1.107(0.5); 1.096(4.2); 1.089(0.9); 1.074(3.0); 0.982(0.6); 0.968(2.1); 0.964(2.5); 0.949(2.4); 0.946(2.1); 0.940(2.1); 0.938(1.8); 0.931(0.6); 0.925(1.5); 0.917(1.3); 0.000(4.3)

Example XII-40: $^1$H-NMR(400.1 MHz, DMSO):

δ = 8.351(1.4); 8.338(1.5); 8.303(15.5); 8.290(15.9); 7.666(1.4); 7.653(1.4); 7.607(15.9); 7.594(15.0); 4.415(4.9); 3.814(11.7); 3.777(16.0); 3.590(11.5); 3.554(8.3); 3.368(0.6); 3.318(87.1); 3.267(0.3); 2.732(10.6); 2.723(11.0); 2.682(0.3); 2.677(0.4); 2.558(0.4); 2.554(0.3); 2.530(1.3); 2.517(24.5); 2.513(48.6); 2.508(64.9); 2.504(46.3); 2.500(21.9); 2.335(0.4); 2.199(13.7); 2.189(13.4); 1.809(0.6);

-continued 1.795(1.6); 1.786(1.7); 1.774(0.9); 1.620(0.9); 1.607(1.7); 1.599(1.6); 1.585(0.6); 1.209(0.7); 1.194(4.6); 1.185(5.7); 1.169(9.4); 1.166(9.3); 1.161(8.0); 1.146(8.2); 1.142(8.4); 1.127(2.0); 1.033(3.0); 1.019(6.8); 1.016(3.8); 1.007(7.4); 1.001(7.5); 0.994(7.2); 0.984(7.0); 0.982(7.4); 0.976(5.0); 0.971(2.4); 0.967(2.9); 0.960(4.5); 0.946(1.4)

Example XII-41: $^1$H-NMR(300.2 MHz, CDCl3):

δ = 8.315(0.4); 8.306(0.9); 8.301(1.0); 8.295(1.3); 8.284(1.6); 8.272(9.5); 8.264(9.8); 7.859(0.4); 7.823(0.5); 7.814(0.5); 7.616(9.6); 7.608(9.6); 7.582(0.7); 7.574(0.7); 7.539(0.8); 7.530(0.8); 7.503(1.2); 7.494(1.2); 7.264(16.9); 5.077(0.7); 5.053(0.7); 4.329(2.9); 4.045(0.5); 3.590(7.3); 3.541(11.2); 3.376(9.1); 3.327(5.8); 3.265(0.3); 3.251(0.4); 3.247(0.4); 3.233(0.4); 3.058(0.4); 3.042(0.5); 2.836(0.4); 2.725(8.1); 2.710(9.0); 2.683(0.5); 2.675(0.5); 2.665(0.5); 2.656(0.4); 2.390(9.2); 2.375(8.6); 1.763(0.4); 1.745(1.2); 1.733(1.5); 1.718(1.3); 1.702(0.9); 1.691(0.7); 1.683(2.4); 1.655(0.4); 1.645(0.5); 1.576(15.3); 1.496(0.3); 1.483(3.7); 1.471(1.6); 1.459(4.7); 1.441(0.7); 1.429(0.9); 1.417(1.1); 1.410(1.2); 1.396(0.9); 1.389(0.4); 1.377(0.5); 1.199(0.7); 1.175(0.7); 1.127(0.8); 1.118(3.0); 1.112(1.9); 1.094(2.4); 1.078(4.8); 1.050(1.4); 1.014(0.5); 1.009(0.8); 0.987(1.4); 0.980(1.3); 0.969(1.3); 0.963(4.2); 0.957(4.4); 0.946(10.0); 0.941(16.0); 0.930(7.4); 0.912(7.2); 0.908(8.4); 0.901(2.9); 0.891(1.9); 0.873(4.2); 0.862(2.6); 0.827(0.4); 0.011(0.5); 0.000(12.9); −0.011(0.7)

Example XII-42: $^1$H-NMR(400.1 MHz, DMSO):

δ = 8.486(15.6); 8.469(0.7); 7.617(0.4); 7.556(16.0); 3.554(6.0); 3.519(9.6); 3.413(8.0); 3.377(5.0); 3.315(28.9); 2.762(7.3); 2.752(7.9); 2.531(1.2); 2.526(1.6); 2.518(14.2); 2.513(29.0); 2.509(39.4); 2.504(28.5); 2.499(14.2); 2.470(9.6); 2.459(9.1); 2.336(0.3); 1.101(0.4); 1.087(2.7); 1.078(3.5); 1.062(5.8); 1.060(5.9); 1.053(5.7); 1.039(6.3); 1.036(6.3); 1.021(1.6); 0.964(2.3); 0.950(4.5); 0.947(2.6); 0.936(5.0); 0.932(5.1); 0.926(4.2); 0.922(3.4); 0.912(6.0); 0.907(3.3); 0.900(1.8); 0.897(2.2); 0.889(3.1); 0.875(2.0); 0.858(0.7)

Use Examples

Example A: In Vivo Preventive Test on *Botrytis cinerea* (Grey Mould)

The tested active ingredients are prepared by homogenization in a mixture of acetone/Dimethyl sulfoxide/Tween®, and then diluted with water to obtain the desired active material concentration.

The young plants of gherkin are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-2 | 94 |
| I-3 | 100 |
| I-4 | 100 |
| I-5 | 100 |
| I-29 | 94 |
| I-39 | 99 |
| I-40 | 97 |
| I-49 | 99 |
| I-50 | 100 |
| I-51 | 100 |
| I-53 | 100 |
| I-54 | 100 |
| I-58 | 98 |
| I-60 | 100 |
| I-61 | 99 |
| I-62 | 100 |
| I-65 | 100 |
| I-67 | 99 |
| I-71 | 100 |
| I-76 | 100 |
| I-77 | 100 |
| I-79 | 99 |
| I-81 | 99 |
| I-82 | 100 |
| I-83 | 100 |
| I-89 | 100 |
| I-90 | 100 |
| I-91 | 95 |

In this test the following compounds according to the invention showed efficacy of at least 70% at a concentration of 100 ppm of active ingredient.

| Ex_no. | Eff. % |
|---|---|
| I-6 | 76 |
| I-7 | 100 |
| I-8 | 87 |
| I-16 | 87 |
| I-18 | 100 |
| I-19 | 100 |
| I-25 | 99 |
| I-27 | 98 |
| I-33 | 94 |

Example B: In Vivo Preventive Test on *Puccinia recondita* (Brown Rust on Wheat)

The tested active ingredients are prepared by homogenization in a mixture of acetone/Dimethyl sulfoxide/Tween®, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-2 | 94 |
| I-3 | 98 |
| I-4 | 100 |
| I-5 | 100 |
| I-29 | 97 |
| I-33 | 93 |
| I-36 | 97 |
| I-39 | 97 |
| I-40 | 97 |
| I-49 | 100 |
| I-50 | 94 |
| I-51 | 98 |
| I-53 | 94 |
| I-54 | 97 |
| I-55 | 79 |
| I-56 | 86 |
| I-57 | 86 |
| I-58 | 97 |
| I-59 | 98 |
| I-60 | 98 |
| I-61 | 98 |
| I-62 | 98 |
| I-64 | 83 |
| I-65 | 98 |
| I-67 | 98 |
| I-68 | 94 |
| I-69 | 98 |
| I-70 | 94 |
| I-71 | 94 |
| I-75 | 81 |
| I-76 | 100 |
| I-77 | 98 |
| I-79 | 98 |
| I-80 | 88 |
| I-81 | 100 |
| I-82 | 98 |
| I-83 | 100 |
| I-84 | 88 |
| I-87 | 89 |
| I-88 | 89 |
| I-89 | 100 |
| I-91 | 89 |

In this test the following compounds according to the invention showed efficacy of at least 70% at a concentration of 100 ppm of active ingredient.

| Ex_no. | Eff. % |
|---|---|
| I-6 | 81 |
| I-7 | 94 |
| I-8 | 94 |
| I-16 | 75 |
| I-18 | 94 |
| I-19 | 88 |
| I-21 | 98 |
| I-25 | 100 |
| I-31 | 83 |
| I-32 | 75 |
| I-45 | 97 |
| I-46 | 88 |

Example C: In Vivo Preventive Test on *Pyrenophora teres* (Net Blotch on Barley)

The tested active ingredients are prepared by homogenization in a mixture of acetone/Dimethyl sulfoxide/Tween®, and then diluted with water to obtain the desired active material concentration.

The young plants of barley are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-3 | 100 |
| I-29 | 95 |
| I-33 | 75 |
| I-36 | 88 |
| I-39 | 100 |
| I-40 | 100 |
| I-49 | 93 |
| I-50 | 79 |
| I-51 | 100 |
| I-53 | 86 |
| I-56 | 88 |
| I-57 | 88 |
| I-58 | 95 |
| I-60 | 100 |
| I-61 | 93 |
| I-62 | 100 |
| I-65 | 100 |
| I-67 | 86 |
| I-68 | 71 |
| I-69 | 93 |
| I-71 | 79 |
| I-76 | 79 |
| I-77 | 86 |
| I-81 | 97 |
| I-82 | 97 |
| I-83 | 88 |
| I-89 | 100 |

In this test the following compounds according to the invention showed efficacy of at least 70% at a concentration of 100 ppm of active ingredient.

| Ex_no. | Eff. % |
|---|---|
| I-1 | 83 |
| I-7 | 92 |
| I-18 | 83 |
| I-19 | 75 |
| I-25 | 97 |

Example D: In Vivo Preventive Test on *Septoria tritici* (Leaf Spot on Wheat)

The tested active ingredients are prepared by homogenization in a mixture of acetone/Dimethyl sulfoxide/Tween®, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-2 | 100 |
| I-3 | 100 |
| I-4 | 96 |
| I-5 | 100 |
| I-29 | 100 |
| I-33 | 100 |
| I-36 | 100 |
| I-39 | 100 |
| I-40 | 100 |
| I-49 | 100 |
| I-50 | 100 |
| I-51 | 100 |
| I-53 | 100 |
| I-54 | 100 |
| I-55 | 100 |
| I-56 | 92 |
| I-57 | 92 |
| I-58 | 100 |
| I-59 | 100 |
| I-60 | 97 |
| I-61 | 100 |
| I-62 | 100 |
| I-64 | 97 |
| I-65 | 100 |
| I-66 | 92 |
| I-67 | 100 |
| I-68 | 100 |
| I-69 | 100 |
| I-70 | 100 |
| I-71 | 100 |
| I-72 | 80 |
| I-73 | 100 |
| I-74 | 100 |
| I-75 | 100 |
| I-76 | 100 |
| I-77 | 100 |
| I-79 | 100 |
| I-80 | 100 |
| I-81 | 100 |
| I-82 | 100 |
| I-83 | 100 |
| I-85 | 78 |
| I-86 | 72 |
| I-87 | 83 |
| I-88 | 100 |
| I-89 | 100 |
| I-90 | 78 |
| I-91 | 100 |

In this test the following compounds according to the invention showed efficacy of at least 70% at a concentration of 100 ppm of active ingredient.

| Ex_no. | Eff. % |
|---|---|
| I-6 | 100 |
| I-7 | 98 |
| I-8 | 94 |
| I-12 | 88 |
| I-15 | 94 |
| I-16 | 98 |
| I-17 | 97 |
| I-18 | 98 |
| I-19 | 75 |
| I-21 | 100 |
| I-22 | 88 |
| I-25 | 100 |
| I-26 | 97 |
| I-31 | 100 |
| I-45 | 100 |
| I-46 | 100 |
| I-84 | 81 |

Example E: In Vivo Preventive Test on *Sphaerotheca fuliginea* (Powdery Mildew on Cucurbits)

The tested active ingredients are prepared by homogenization in a mixture of acetone/Dimethyl sulfoxide/Tween®, and then diluted with water to obtain the desired active material concentration.

The young plants of gherkin are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-2 | 95 |
| I-4 | 100 |
| I-5 | 100 |
| I-29 | 100 |
| I-33 | 100 |
| I-36 | 100 |
| I-39 | 100 |
| I-40 | 100 |
| I-48 | 83 |
| I-49 | 100 |
| I-50 | 100 |
| I-51 | 100 |
| I-53 | 100 |
| I-54 | 100 |
| I-55 | 100 |
| I-56 | 100 |
| I-57 | 95 |
| I-58 | 100 |

-continued

| Ex_no. | Eff. % |
|---|---|
| I-59 | 100 |
| I-60 | 100 |
| I-61 | 100 |
| I-62 | 100 |
| I-64 | 100 |
| I-65 | 100 |
| I-66 | 80 |
| I-67 | 98 |
| I-68 | 100 |
| I-69 | 100 |
| I-70 | 100 |
| I-71 | 100 |
| I-72 | 98 |
| I-73 | 100 |
| I-74 | 100 |
| I-75 | 100 |
| I-76 | 100 |
| I-77 | 100 |
| I-79 | 100 |
| I-80 | 100 |
| I-81 | 100 |
| I-82 | 100 |
| I-83 | 100 |
| I-85 | 89 |
| I-87 | 72 |
| I-88 | 98 |
| I-89 | 100 |
| I-90 | 100 |
| I-91 | 98 |

In this test the following compounds according to the invention showed efficacy of at least 70% at a concentration of 100 ppm of active ingredient.

| Ex_no. | Eff. % |
|---|---|
| I-3 | 100 |
| I-6 | 100 |
| I-7 | 100 |
| I-8 | 100 |
| I-9 | 94 |
| I-10 | 75 |
| I-11 | 79 |
| I-12 | 100 |
| I-13 | 94 |
| I-14 | 100 |
| I-15 | 98 |
| I-16 | 100 |
| I-17 | 100 |
| I-18 | 100 |
| I-19 | 100 |
| I-21 | 100 |
| I-23 | 88 |
| I-24 | 94 |
| I-25 | 100 |
| I-26 | 100 |
| I-27 | 100 |
| I-30 | 94 |
| I-31 | 90 |
| I-34 | 100 |
| I-35 | 78 |
| I-38 | 100 |
| I-41 | 100 |
| I-42 | 98 |
| I-43 | 100 |
| I-44 | 100 |
| I-45 | 100 |
| I-46 | 100 |

Example F: In Vivo Preventive Test on *Uromyces appendiculatus* (Bean Rust)

The tested active ingredients are prepared by homogenization in a mixture of acetone/Dimethyl sulfoxide/Tween®, and then diluted with water to obtain the desired active material concentration.

The young plants of bean are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Ex_no. | Eff. % |
|---|---|
| I-2 | 100 |
| I-3 | 100 |
| I-4 | 97 |
| I-5 | 98 |
| I-29 | 100 |
| I-33 | 100 |
| I-36 | 100 |
| I-39 | 100 |
| I-40 | 100 |
| I-48 | 81 |
| I-49 | 81 |
| I-50 | 100 |
| I-51 | 86 |
| I-53 | 98 |
| I-54 | 100 |
| I-55 | 98 |
| I-56 | 96 |
| I-57 | 96 |
| I-58 | 100 |
| I-59 | 100 |
| I-60 | 100 |
| I-61 | 100 |
| I-62 | 100 |
| I-64 | 94 |
| I-65 | 100 |
| I-67 | 100 |
| I-68 | 100 |
| I-69 | 100 |
| I-70 | 99 |
| I-71 | 99 |
| I-72 | 100 |
| I-76 | 100 |
| I-77 | 100 |
| I-79 | 100 |
| I-80 | 99 |
| I-81 | 100 |
| I-82 | 100 |
| I-83 | 100 |
| I-84 | 100 |
| I-87 | 78 |
| I-89 | 100 |
| I-91 | 97 |

In this test the following compounds according to the invention showed efficacy of at least 70% at a concentration of 100 ppm of active ingredient.

| Ex_no. | Eff. % |
|---|---|
| I-1 | 80 |
| I-6 | 100 |
| I-7 | 100 |
| I-8 | 100 |
| I-11 | 75 |
| I-13 | 95 |
| I-14 | 87 |
| I-16 | 91 |
| I-17 | 94 |
| I-18 | 97 |
| I-19 | 98 |
| I-21 | 100 |
| I-23 | 92 |
| I-24 | 92 |
| I-25 | 100 |
| I-27 | 98 |
| I-30 | 100 |
| I-31 | 94 |
| I-41 | 94 |
| I-44 | 94 |
| I-45 | 100 |

Example G: *Blumeria* Test (Barley)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of *Blumeria graminis* f. sp. *hordei*.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
|---|---|
| I-3 | 100 |
| I-4 | 100 |
| I-5 | 100 |
| I-6 | 100 |
| I-7 | 100 |
| I-8 | 100 |
| I-18 | 100 |
| I-19 | 100 |
| I-21 | 100 |
| I-25 | 100 |
| I-27 | 100 |
| I-29 | 100 |
| I-31 | 100 |
| I-33 | 100 |
| I-36 | 100 |
| I-39 | 100 |
| I-40 | 100 |
| I-45 | 100 |
| I-49 | 100 |
| I-51 | 100 |
| I-53 | 100 |
| I-54 | 100 |
| I-57 | 100 |
| I-58 | 100 |
| I-60 | 100 |
| I-61 | 100 |
| I-62 | 100 |
| I-65 | 100 |
| I-69 | 100 |
| I-70 | 100 |
| I-71 | 100 |
| I-76 | 100 |
| I-77 | 100 |
| I-81 | 100 |
| I-82 | 100 |
| I-94 | 100 |
| I-95 | 100 |

Example H: *Fusarium culmorum*-Test (Wheat)/Curative

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are slightly injured by using a sandblast and afterwards they are sprayed with a conidia suspension of *Fusarium culmorum* and placed for 24 hours in a greenhouse under a translucent incubation cabinet at a temperature of approximately 22° C. and a relative atmospheric humidity of approximately 100% and are subsequently sprayed with the preparation of active compound at the stated rate of application.

After the spray coating has been dried, the plants remain in the greenhouse under translucent incubation cloches at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
|---|---|
| I-3 | 100 |
| I-4 | 92 |
| I-5 | 100 |
| I-6 | 100 |
| I-7 | 100 |
| I-8 | 100 |
| I-18 | 100 |
| I-19 | 100 |
| I-21 | 100 |
| I-25 | 100 |
| I-29 | 100 |
| I-39 | 100 |
| I-45 | 100 |
| I-49 | 100 |
| I-51 | 100 |
| I-53 | 90 |

| Ex_no. | Eff. % |
| --- | --- |
| I-60 | 83 |
| I-61 | 100 |
| I-62 | 83 |
| I-65 | 100 |

Example I: *Fusarium graminearum*-Test (Barley)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium graminearum*.

The plants are placed in the greenhouse under a translucent incubation cabinet at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
| --- | --- |
| I-3 | 100 |
| I-5 | 100 |
| I-6 | 100 |
| I-7 | 100 |
| I-8 | 100 |
| I-18 | 100 |
| I-19 | 100 |
| I-21 | 100 |
| I-25 | 100 |
| I-27 | 100 |
| I-29 | 100 |
| I-33 | 100 |
| I-36 | 94 |
| I-39 | 100 |
| I-40 | 100 |
| I-45 | 100 |
| I-46 | 92 |
| I-49 | 100 |
| I-51 | 100 |
| I-53 | 100 |
| I-54 | 100 |
| I-58 | 100 |
| I-60 | 100 |
| I-61 | 100 |
| I-62 | 100 |
| I-65 | 100 |
| I-69 | 71 |
| I-71 | 100 |
| I-76 | 86 |
| I-77 | 86 |
| I-81 | 100 |
| I-82 | 100 |
| I-95 | 100 |

Example J: *Fusarium nivale* (var. *majus*)-Test (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
| --- | --- |
| I-3 | 100 |
| I-4 | 71 |
| I-5 | 100 |
| I-6 | 100 |
| I-7 | 100 |
| I-8 | 100 |
| I-18 | 100 |
| I-19 | 100 |
| I-21 | 100 |
| I-25 | 100 |
| I-27 | 93 |
| I-29 | 100 |
| I-31 | 75 |
| I-33 | 93 |
| I-39 | 100 |
| I-40 | 86 |
| I-45 | 100 |
| I-46 | 100 |
| I-49 | 100 |
| I-51 | 100 |
| I-53 | 100 |
| I-54 | 100 |
| I-57 | 71 |
| I-58 | 100 |
| I-60 | 100 |
| I-61 | 100 |
| I-62 | 100 |
| I-65 | 100 |
| I-70 | 88 |
| I-71 | 94 |
| I-76 | 100 |
| I-77 | 83 |
| I-81 | 100 |

-continued

| Ex_no. | Eff. % |
|---|---|
| I-82 | 100 |
| I-94 | 100 |
| I-95 | 100 |

Example K: *Leptosphaeria nodorum* Test (Wheat)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Leptosphaeria nodorum*. The plants remain for 48 hours in an incubation cabinet at approximately 20° C. and a relative atmospheric humidity of approximately 100%.

The plants are placed in the greenhouse at a temperature of approximately 22° C. and a relative atmospheric humidity of approximately 80%.

The test is evaluated 8 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
|---|---|
| I-3 | 100 |
| I-4 | 80 |
| I-5 | 90 |
| I-6 | 100 |
| I-7 | 100 |
| I-8 | 92 |
| I-18 | 100 |
| I-19 | 100 |
| I-21 | 94 |
| I-25 | 100 |
| I-29 | 100 |
| I-31 | 88 |
| I-33 | 86 |
| I-39 | 100 |
| I-40 | 100 |
| I-45 | 88 |
| I-46 | 83 |
| I-49 | 100 |
| I-51 | 100 |
| I-53 | 100 |
| I-58 | 93 |
| I-60 | 100 |
| I-61 | 75 |
| I-62 | 100 |
| I-65 | 100 |
| I-69 | 89 |
| I-70 | 89 |
| I-81 | 100 |
| I-82 | 100 |
| I-94 | 71 |
| I-95 | 100 |

Example L: *Phakopsora* Test (Soybeans)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex_no. | Eff. % |
|---|---|
| I-3 | 100 |
| I-4 | 95 |
| I-5 | 100 |
| I-6 | 95 |
| I-7 | 94 |
| I-8 | 95 |
| I-18 | 95 |
| I-25 | 99 |
| I-49 | 96 |
| I-51 | 100 |
| I-53 | 93 |
| I-54 | 99 |
| I-60 | 100 |
| I-62 | 99 |
| I-65 | 100 |
| I-69 | 91 |
| I-76 | 100 |
| I-77 | 100 |
| I-82 | 100 |

In this test the following compounds according to the invention showed efficacy of 70% or even higher at a concentration of 10 ppm of active ingredient.

| Ex_no. | Eff. % |
|---|---|
| I-19 | 96 |
| I-21 | 93 |
| I-30 | 75 |
| I-39 | 88 |
| I-40 | 73 |
| I-45 | 93 |
| I-58 | 89 |
| I-61 | 80 |
| I-81 | 85 |

Example M: *Podosphaera* Test (Apples)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex_no. | Eff. % |
|--------|--------|
| I-3    | 100    |
| I-5    | 100    |
| I-18   | 97     |

Example N: Pyricularia *Oryzae*-Test (Rice)/Preventive

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Pyricularia oryzae*. The plants remain for 25 hours in an incubation cabinet at approximately 25° C. and a relative atmospheric humidity of approximately 100%.

The plants are placed in the greenhouse under a translucent incubations cabinet at a temperature of approximately 25° C. and a relative atmospheric humidity of approximately 100%.

The test is evaluated 8 days after the inoculation. 0% means an efficacy which corresponds to that of the control, while an efficacy of 100% means that no disease is observed.

In this test the following compounds according to the invention showed an efficacy of 70% or even higher at a concentration of 500 ppm of active ingredient.

| Ex_no. | Eff. % |
|--------|--------|
| I-3    | 100    |
| I-5    | 75     |
| I-6    | 83     |
| I-7    | 100    |
| I-8    | 100    |
| I-19   | 100    |
| I-27   | 89     |
| I-29   | 70     |
| I-39   | 80     |
| I-46   | 78     |
| I-51   | 80     |
| I-53   | 80     |
| I-54   | 78     |
| I-58   | 100    |
| I-65   | 86     |
| I-71   | 80     |
| I-76   | 71     |
| I-77   | 86     |
| I-81   | 100    |
| I-82   | 100    |
| I-94   | 70     |
| I-95   | 100    |

Example O: *Venturia* Test (Apples)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex_no. | Eff. % |
|--------|--------|
| I-3    | 98     |
| I-5    | 100    |
| I-6    | 100    |
| I-7    | 98     |
| I-8    | 100    |
| I-18   | 100    |
| I-25   | 89     |
| I-49   | 100    |
| I-51   | 94     |
| I-53   | 97     |
| I-54   | 89     |
| I-60   | 100    |
| I-62   | 100    |
| I-65   | 100    |
| I-69   | 100    |
| I-76   | 74     |
| I-82   | 95     |

The invention claimed is:

1. Triazole derivative of formula (I)

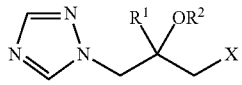

wherein
R$^1$ represents C$_1$-C$_8$-haloalkyl; C$_2$-C$_8$-halooalkenyl; C$_2$-C$_8$-haloalkynyl; C$_3$-C$_7$-halocycloalkyl-C$_1$-C$_4$-alkyl; C$_3$-C$_7$-halocycloalkyl-C$_1$-C$_4$-haloalkyl; C$_3$-C$_7$-cycloalkyl-C$_1$-C$_4$-haloalkyl; substituted or non-substituted C$_3$-C$_7$-cycloalkyl; substituted or non-substituted C$_3$-C$_7$-cycloalkenyl; substituted or non-substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; or substituted or non-substituted heterocycloalkyl-C$_1$-C$_8$-alkyl;

R$^2$ represents H, C$_1$-C$_8$-alkyl, —Si(R$^{3a}$)(R$^{3b}$)(R$^{3c}$), —P(O)(OH)$_2$, —CH$_2$—O—P(O)(OH)$_2$, substituted or non-substituted —C(O)—C$_1$-C$_8$-alkyl or substituted, non-substituted —C(O)—C$_3$-C$_7$-cycloalkyl, substituted or non-substituted —C(O)NH—C$_1$-C$_8$-alkyl; substituted or non-substituted —C(O)N-di-C$_1$-C$_8$-alkyl; or substituted or non-substituted —C(O)O—C$_1$-C$_8$-alkyl;

R$^{3a}$, R$^{3b}$, R$^{3c}$ independent from each other represent a substituted or non-substituted C$_1$-C$_8$-alkyl;

and

X represents a substituted or non-substituted unsaturated 6-membered heterocycle containing 1 or 2 nitrogen atom(s) as heteroatom(s) or a benzannulated derivative thereof;

and/or a salt and/or N-oxide thereof.

2. Triazole derivative of formula (I) and/or salt and/or N-oxide according to claim 1, wherein
R$^1$ represents C$_1$-C$_8$-haloalkyl; C$_2$-C$_5$-halooalkenyl; C$_2$-C$_8$-haloalkynyl; C$_3$-C$_7$-halocycloalkyl-C$_1$-C$_4$-alkyl; C$_3$-C$_7$-halocycloalkyl-C$_1$-C$_4$-haloalkyl; C$_3$-C$_7$-cycloalkyl-C$_1$-C$_4$-haloalkyl; substituted or non-substituted C$_3$-C$_7$-cycloalkyl; substituted or non-substituted C$_3$-C$_7$-cycloalkenyl; substituted or non-substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; or substituted or non-substituted heterocycloalkyl-C$_1$-C$_8$-alkyl;

R$^2$ represents H, C$_1$-C$_8$-alkyl, —Si(R$^{3a}$)(R$^{3b}$)(R$^{3c}$), —P(O)(OH)$_2$, —CH$_2$—O—P(O)(OH)$_2$, substituted or non-substituted —C(O)—C$_1$-C$_8$-alkyl or substituted, non-substituted —C(O)—C$_3$-C$_7$-cycloalkyl, substituted or non-substituted —C(O)NH—C$_1$-C$_5$-alkyl; substituted or non-substituted —C(O)N-di-C$_1$-C$_8$-alkyl; or substituted or non-substituted —C(O)O—C$_1$-C$_8$-alkyl;

R$^{3a}$, R$^{3b}$, R$^{3c}$ independent from each other represent a substituted or non-substituted C$_1$-C$_8$-alkyl;

and

X represents a substituted or non-substituted unsaturated 6 membered heterocycle containing 1 or 2 nitrogen atom(s) as heteroatom(s) or a benzannulated derivative thereof, with the provisio that X does not represent 2-pyridinyl.

3. Triazole derivative of formula (I) and/or salt and/or N-oxide according to claim 1, wherein
R$^1$ represents C$_1$-C$_5$-haloalkyl or substituted or non-substituted C$_3$-C$_7$-cycloalkyl;

R$^2$ represents H, C$_1$-C$_8$-alkyl or substituted or non-substituted —C(O)—C$_1$-C$_8$-alkyl;

and

X represents a substituted or non-substituted 3-pyridinyl, 4-pyridinyl, 4-pyrimidinyl, 5-pyrimidinyl, pyrazin-2-yl, pyridazin-3-yl, pyridazin-4-yl, quinoline-2-yl or quinoline-3-yl.

4. Method for controlling one or more harmful microorganisms, comprising applying a compound of formula (I) and/or salt and/or N-oxide according to claim 1, to the harmful microorganisms and/or a habitat thereof.

5. Method for controlling phytopathogenic harmful fungi, comprising applying a compound of formula (I) and/or salt and/or N-oxide according to claim 1, to the phytopathogenic harmful fungi and/or a habitat thereof.

6. The method according to claim 5, comprising treatment of one or more transgenic plants.

7. Composition for controlling harmful microorganisms, comprising a content of at least one compound of formula (I) and/or salt and/or N-oxide according to claim 1, in addition to one or more extenders and/or surfactants.

8. Composition according to claim 7 comprising at least one further active ingredient selected from the group of the insecticides, attractants, sterilants, bactericides, acaricides, nematicides, fungicides, growth regulators, herbicides, fertilizers, safeners and semiochemicals.

9. The composition according to claim 7, for control of phytopathogenic harmful fungi.

10. Process for producing a composition for controlling harmful microorganisms, optionally for controlling phytopathogenic harmful fungi, comprising mixing a compound of formula (I) and/or salt and/or N-oxide according to claim 1, with one or more extenders and/or surfactants.

11. Seed treated with a compound of formula (I) and/or salt and/or N-oxide according to claim 1.

12. Compound of formula (V)

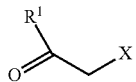

wherein
X represents a substituted or non-substituted unsaturated 6-membered heterocycle containing 1 or 2 nitrogen atom(s) as heteroatom(s) or a benzannulated derivative thereof;

and

R$^1$ represents a substituted or non-substituted 1-halogen-cyclopropyl, 1-halogen-2-methylpropan-2-yl or 2-halogen-propan-2-yl;

and/or salt and/or N-oxide thereof.

13. Epoxide of formula (XII)

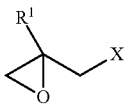
(XII)

wherein

X represents a substituted or non-substituted unsaturated 6-membered heterocycle containing 1 or 2 nitrogen atom(s) as heteroatom(s) or a benzannulated derivative thereof;

and $R^1$ represents $C_1$-$C_8$-haloalkyl; $C_2$-$C_5$-halooalkenyl; $C_2$-$C_8$-haloalkynyl; $C_3$-$C_7$-halocycloalkyl-$C_1$-$C_4$-alkyl; $C_3$-$C_7$-halocycloalkyl-$C_1$-$C_4$-haloalkyl; $C_3$-$C_7$-cycloalkyl-$C_1$-$C_4$-haloalkyl; substituted or non-substituted $C_3$-$C_7$-cycloalkyl; substituted or non-substituted $C_3$-$C_7$-cycloalkenyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; or substituted or non-substituted heterocycloalkyl and/or salt and/or N-oxide of the epoxide of formula (XII).

14. Compound of formula (V)

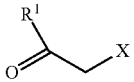
(V)

wherein

X represents a substituted or non-substituted 3-pyridinyl or 4-pyridinyl or a benzannulated derivative thereof;

and $R^1$ represents a substituted or non-substituted 1-$C_1$-$C_8$-alkylcyclopropyl, 2-$C_1$-$C_8$-alkylcyclopropyl, $C_1$-$C_8$-haloalkyl, 1-$C_1$-$C_8$-alkylcyclohexyl, 1-arylcyclopropyl or 2-arylcyclopropyl;

and/or salt and/or N-oxide of the compound of formula (V).

15. Alcohol of formula (XV)

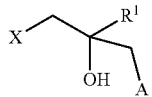
(XV)

wherein

X represents a substituted or non-substituted unsaturated 6-membered heterocycle containing 1 or 2 nitrogen atom(s) as heteroatom(s) or a benzannulated derivative thereof, and $R^1$ represents $C_1$-$C_8$-haloalkyl; $C_2$-$C_5$-halooalkenyl; $C_2$-$C_8$-haloalkynyl; $C_3$-$C_7$-halocycloalkyl-$C_1$-$C_4$-alkyl; $C_3$-$C_7$-halocycloalkyl-$C_1$-$C_4$-haloalkyl; $C_3$-$C_7$-cycloalkyl-$C_1$-$C_4$-haloalkyl; substituted or non-substituted $C_3$-$C_7$-cycloalkyl; substituted or non-substituted $C_3$-$C_7$-cycloalkenyl; substituted or non-substituted arylalkyl; substituted or non-substituted arylalkenyl; substituted or non-substituted arylalkynyl; substituted or non-substituted phenoxyalkyl; substituted or non-substituted phenylcycloalkyl; substituted or non-substituted hetaryl; substituted hetarylalkyl; substituted or non-substituted heterocycloalkyl; or substituted or non-substituted heterocycloalkyl-$C_1$-$C_8$-alkyl;

and

A represents chloro, bromo, iodo, O—$SO_2$—$C_1$-$C_8$-alkyl or O—$SO_2$-aryl;

and/or salt and/or N-oxide thereof.

* * * * *